United States Patent
Storer et al.

(10) Patent No.: US 7,598,373 B2
(45) Date of Patent: Oct. 6, 2009

(54) PROCESS FOR THE PRODUCTION OF 2-C-METHYL-D-RIBONOLACTONE

(75) Inventors: Richard Storer, Folkestone (GB); Adel M. Moussa, Burlington, MA (US); Narayan Chaudhuri, Acton, MA (US); Frank Waligora, Haverhill, MA (US)

(73) Assignee: Idenix Pharmaceuticals, Inc., Cambridge, MA (US)

( * ) Notice: Subject to any disclaimer, the term of this patent is extended or adjusted under 35 U.S.C. 154(b) by 89 days.

(21) Appl. No.: 10/735,408

(22) Filed: Dec. 12, 2003

(65) Prior Publication Data

US 2005/0020825 A1 Jan. 27, 2005

Related U.S. Application Data

(60) Provisional application No. 60/432,766, filed on Dec. 12, 2002, provisional application No. 60/466,194, filed on Apr. 28, 2003.

(51) Int. Cl.
C07H 1/00 (2006.01)
C07H 3/10 (2006.01)
(52) U.S. Cl. .................................. 536/124; 536/1.11
(58) Field of Classification Search ............ 536/1.11, 536/124
See application file for complete search history.

(56) References Cited

U.S. PATENT DOCUMENTS

| | | | |
|---|---|---|---|
| 3,074,929 A | 1/1963 | Hitchings et al. |
| 3,116,282 A | 12/1963 | Hunter |
| 3,480,613 A | 11/1969 | Walton |
| 3,798,209 A | 3/1974 | Wilkowski, et al. |
| 3,891,623 A | 6/1975 | Vorbruggen et al. |
| 4,022,889 A | 5/1977 | Bannister et al. |
| 4,058,602 A | 11/1977 | Beisler et al. |
| RE29,835 E | 11/1978 | Witkowski et al. |
| 4,209,613 A | 6/1980 | Vorbruggen |
| 4,239,753 A | 12/1980 | Skulnick et al. |
| 4,294,766 A | 10/1981 | Schmidt et al. |
| 4,522,811 A | 6/1985 | Eppstein et al. |
| 4,605,659 A | 8/1986 | Verheyden et al. |
| 4,689,404 A | 8/1987 | Kawada et al. |
| 4,754,026 A | 6/1988 | Kawada et al. |
| 4,814,477 A | 3/1989 | Wijnberg et al. |
| 4,837,311 A * | 6/1989 | Tam et al. ............ 536/27.14 |
| 4,880,784 A | 11/1989 | Robins et al. |
| 4,952,740 A | 8/1990 | Juge et al. |
| 4,957,924 A | 9/1990 | Beauchamp |
| 5,034,394 A | 7/1991 | Daluge |
| 5,122,517 A | 6/1992 | Vince et al. |
| 5,149,794 A | 9/1992 | Yatvin et al. |
| 5,157,027 A | 10/1992 | Biller et al. |
| 5,194,654 A | 3/1993 | Hostetler et al. |
| 5,200,514 A | 4/1993 | Chu |
| 5,223,263 A | 6/1993 | Hostetler et al. |
| 5,246,924 A | 9/1993 | Fox et al. |
| 5,256,641 A | 10/1993 | Yatvin et al. |
| 5,256,797 A | 10/1993 | Chou et al. |
| 5,322,955 A | 6/1994 | Matsumoto et al. |
| 5,371,210 A | 12/1994 | Chou et al. |
| 5,372,808 A | 12/1994 | Blatt et al. |
| 5,391,769 A | 2/1995 | Matsumoto et al. |
| 5,401,861 A | 3/1995 | Chou |
| 5,411,947 A | 5/1995 | Hostetler et al. |
| 5,463,092 A | 10/1995 | Hostetler et al. |
| 5,539,116 A | 7/1996 | Liotta et al. |
| 5,543,389 A | 8/1996 | Yatvin et al. |
| 5,543,390 A | 8/1996 | Yatvin et al. |
| 5,543,391 A | 8/1996 | Yatvin et al. |
| 5,554,728 A | 9/1996 | Basava et al. |
| 5,565,438 A | 10/1996 | Chu et al. |
| 5,567,688 A | 10/1996 | Chu et al. |
| 5,587,362 A | 12/1996 | Chu et al. |
| 5,606,048 A | 2/1997 | Chou et al. |
| 5,676,942 A | 10/1997 | Testa et al. |
| 5,696,277 A | 12/1997 | Hostetler et al. |
| 5,738,845 A | 4/1998 | Imakawa |
| 5,744,600 A | 4/1998 | Mansuri et al. |
| 5,750,676 A | 5/1998 | Vorbruggen et al. |
| 5,763,418 A | 6/1998 | Matsuda et al. |
| 5,780,617 A | 7/1998 | Van den Bosch et al. |
| 5,789,608 A | 8/1998 | Glazier |
| 5,821,357 A | 10/1998 | Chou et al. |
| 5,830,455 A | 11/1998 | Valtuena et al. |
| 5,849,696 A | 12/1998 | Chretien et al. |
| 5,908,621 A | 6/1999 | Glue et al. |

(Continued)

FOREIGN PATENT DOCUMENTS

CA 2252144 4/2000

(Continued)

OTHER PUBLICATIONS

BeMiller et al, Methods in Carbohydrate Chemistry, 1963, 2, 484-485.*

(Continued)

Primary Examiner—Shaojia Anna Jiang
Assistant Examiner—Ganapathy Krishnan
(74) Attorney, Agent, or Firm—Jones Day

(57) ABSTRACT

The present invention provides an improved process for preparing 2-C-methyl-D-ribonolactone.

30 Claims, 6 Drawing Sheets

U.S. PATENT DOCUMENTS

| | | |
|---|---|---|
| 5,928,636 A | 7/1999 | Alber et al. |
| 5,942,223 A | 8/1999 | Bazer et al. |
| 5,977,061 A | 11/1999 | Holy et al. |
| 5,977,325 A | 11/1999 | McCarthy et al. |
| 5,980,884 A | 11/1999 | Blatt et al. |
| 6,002,029 A | 12/1999 | Hostetler et al. |
| 6,063,628 A | 5/2000 | Loeb et al. |
| 6,140,310 A | 10/2000 | Glazier |
| 6,153,594 A | 11/2000 | Børretzen et al. |
| 6,156,501 A | 12/2000 | McGall et al. |
| 6,172,046 B1 | 1/2001 | Albrecht |
| 6,248,878 B1 | 6/2001 | Matulic-Adamic et al. |
| 6,252,060 B1 | 6/2001 | Hostetler |
| 6,271,212 B1 | 8/2001 | Chu et al. |
| 6,277,830 B1 | 8/2001 | Ganguly et al. |
| 6,312,662 B1 | 11/2001 | Erion et al. |
| 6,340,690 B1 | 1/2002 | Bachand et al. |
| 6,348,587 B1 | 2/2002 | Schinazi et al. |
| 6,369,040 B1 | 4/2002 | Acevedo et al. |
| 6,395,716 B1 | 5/2002 | Gosselin et al. |
| 6,436,437 B1 | 8/2002 | Yatvin et al. |
| 6,444,652 B1 | 9/2002 | Gosselin et al. |
| 6,448,392 B1 | 9/2002 | Hostetler et al. |
| 6,455,508 B1 | 9/2002 | Ramasamy et al. |
| 6,458,772 B1 | 10/2002 | Zhou et al. |
| 6,458,773 B1 | 10/2002 | Gosselin et al. |
| 6,472,373 B1 | 10/2002 | Albrecht |
| 6,495,677 B1 | 12/2002 | Ramasamy et al. |
| 6,566,344 B1 | 5/2003 | Gosselin et al. |
| 6,566,365 B1 | 5/2003 | Storer |
| 6,569,837 B1 | 5/2003 | Gosselin et al. |
| 6,573,248 B2 | 6/2003 | Ramasamy et al. |
| 6,596,700 B2 | 7/2003 | Sommadossi et al. |
| 6,599,887 B2 | 7/2003 | Hostetler et al. |
| 6,605,614 B2 | 8/2003 | Bachand et al. |
| 6,642,206 B2 | 11/2003 | Ramasamy et al. |
| 6,660,721 B2 | 12/2003 | Devos et al. |
| 6,748,161 B2 | 6/2004 | Ko et al. |
| 6,752,981 B1 | 6/2004 | Erion et al. |
| 6,777,395 B2 | 8/2004 | Bhat et al. |
| 6,784,161 B2 | 8/2004 | Ismaili et al. |
| 6,784,166 B2 | 8/2004 | Devos et al. |
| 6,787,526 B1 | 9/2004 | Bryant et al. |
| 6,812,219 B2 | 11/2004 | LaColla et al. |
| 6,815,542 B2 | 11/2004 | Hong et al. |
| 6,831,069 B2 | 12/2004 | Tam et al. |
| 6,833,361 B2 | 12/2004 | Hong et al. |
| 6,846,810 B2 | 1/2005 | Martin et al. |
| 6,875,751 B2 | 4/2005 | Imbach et al. |
| 6,891,036 B2 | 5/2005 | Tamerlani et al. |
| 6,908,924 B2 | 6/2005 | Watanabe et al. |
| 6,911,424 B2 | 6/2005 | Schinazi et al. |
| 6,914,054 B2 | 7/2005 | Sommadossi et al. |
| 6,927,291 B2 | 8/2005 | Jin et al. |
| 6,946,115 B2 | 9/2005 | Erion et al. |
| 6,946,450 B2 | 9/2005 | Gosselin et al. |
| 6,949,522 B2 | 9/2005 | Otto et al. |
| 6,965,033 B2 | 11/2005 | Jiang et al. |
| 6,965,066 B1 | 11/2005 | Jiang et al. |
| 7,056,895 B2 | 6/2006 | Ramasamy et al. |
| 7,094,770 B2 | 8/2006 | Watanabe et al. |
| 7,101,861 B2 | 9/2006 | Sommadossi et al. |
| 7,105,493 B2 | 9/2006 | Sommadossi et al. |
| 7,105,499 B2 | 9/2006 | Carroll et al. |
| 7,125,855 B2 | 10/2006 | Bhat et al. |
| 7,144,868 B2 | 12/2006 | Roberts et al. |
| 7,148,206 B2 | 12/2006 | Sommadossi et al. |
| 7,151,089 B2 | 12/2006 | Roberts et al. |
| 7,157,434 B2 | 1/2007 | Keicher et al. |
| 7,157,441 B2 | 1/2007 | Sommadossi et al. |
| 7,163,929 B2 | 1/2007 | Sommadossi et al. |
| 7,169,766 B2 | 1/2007 | Sommadossi et al. |
| 7,202,224 B2 | 4/2007 | Eldrup et al. |
| 2002/0019363 A1 | 2/2002 | Ismaili et al. |
| 2002/0035085 A1 | 3/2002 | Sommadossi et al. |
| 2002/0052345 A1 | 5/2002 | Erion et al. |
| 2002/0055473 A1 | 5/2002 | Ganguly et al. |
| 2002/0055483 A1 | 5/2002 | Watanabe et al. |
| 2002/0095033 A1 | 7/2002 | Ramasamy et al. |
| 2002/0099072 A1 | 7/2002 | Bachand et al. |
| 2002/0127203 A1 | 9/2002 | Albrecht |
| 2002/0147160 A1 | 10/2002 | Bhat et al. |
| 2002/0156030 A1 | 10/2002 | Ramasamy et al. |
| 2002/0173490 A1 | 11/2002 | Jiang et al. |
| 2002/0198171 A1 | 12/2002 | Schinazi et al. |
| 2003/0008841 A1 | 1/2003 | Devos et al. |
| 2003/0028013 A1 | 2/2003 | Hong et al. |
| 2003/0039630 A1 | 2/2003 | Albrecht |
| 2003/0050229 A1 | 3/2003 | Sommadossi et al. |
| 2003/0053986 A1 | 3/2003 | Zahm |
| 2003/0055013 A1 | 3/2003 | Brass |
| 2003/0060400 A1 | 3/2003 | LaColla et al. |
| 2003/0083306 A1 | 5/2003 | Imbach et al. |
| 2003/0083307 A1 | 5/2003 | Devos et al. |
| 2003/0087873 A1 | 5/2003 | Stuyver et al. |
| 2003/0124512 A1 | 7/2003 | Stuyver |
| 2003/0220290 A1 | 11/2003 | Gosselin et al. |
| 2003/0225028 A1 | 12/2003 | Gosselin et al. |
| 2003/0225029 A1 | 12/2003 | Stuyver |
| 2003/0225037 A1 | 12/2003 | Storer et al. |
| 2003/0236216 A1 | 12/2003 | Devos et al. |
| 2004/0002476 A1 | 1/2004 | Stuyver et al. |
| 2004/0002596 A1 | 1/2004 | Hong et al. |
| 2004/0006002 A1 | 1/2004 | Sommadossi et al. |
| 2004/0023921 A1 | 2/2004 | Hong et al. |
| 2004/0059104 A1 | 3/2004 | Cook et al. |
| 2004/0063622 A1 | 4/2004 | Sommadossi et al. |
| 2004/0063658 A1 | 4/2004 | Roberts et al. |
| 2004/0067901 A1 | 4/2004 | Bhat et al. |
| 2004/0072788 A1 | 4/2004 | Bhat et al. |
| 2004/0077587 A1 | 4/2004 | Sommadossi et al. |
| 2004/0097461 A1 | 5/2004 | Sommadossi et al. |
| 2004/0097462 A1 | 5/2004 | Sommadossi et al. |
| 2004/0101535 A1 | 5/2004 | Sommadossi et al. |
| 2004/0102414 A1 | 5/2004 | Sommadossi et al. |
| 2004/0110717 A1 | 6/2004 | Carroll et al. |
| 2004/0110718 A1 | 6/2004 | Devos et al. |
| 2004/0121980 A1 | 6/2004 | Martin et al. |
| 2004/0147464 A1 | 7/2004 | Roberts et al. |
| 2004/0229839 A1 | 11/2004 | Babu et al. |
| 2004/0248844 A1 | 12/2004 | Ismaili et al. |
| 2004/0259934 A1 | 12/2004 | Olsen et al. |
| 2004/0266722 A1 | 12/2004 | Devos et al. |
| 2004/0266723 A1 | 12/2004 | Otto et al. |
| 2004/0266996 A1 | 12/2004 | Rabi |
| 2005/0009737 A1 | 1/2005 | Clark et al. |
| 2005/0020825 A1 | 1/2005 | Storer et al. |
| 2005/0031588 A1 | 2/2005 | Sommadossi et al. |
| 2005/0038240 A1 | 2/2005 | Connolly et al. |
| 2005/0090463 A1 | 4/2005 | Roberts et al. |
| 2005/0101550 A1 | 5/2005 | Roberts et al. |
| 2005/0107312 A1 | 5/2005 | Keicher et al. |
| 2005/0113330 A1 | 5/2005 | Imbach et al. |
| 2005/0119200 A1 | 6/2005 | Roberts et al. |
| 2005/0124532 A1 | 6/2005 | Sommadossi et al. |
| 2005/0137141 A1 | 6/2005 | Hilfinger et al. |
| 2005/0137161 A1 | 6/2005 | Sommadossi et al. |
| 2005/0215511 A1 | 9/2005 | Roberts et al. |
| 2006/0040890 A1 | 2/2006 | Martin et al. |
| 2006/0111311 A1 | 5/2006 | Keicher et al. |
| 2006/0166865 A1 | 7/2006 | Sommadossi et al. |
| 2006/0194835 A1 | 8/2006 | Dugourd et al. |
| 2006/0199783 A1 | 9/2006 | Wang et al. |
| 2006/0241064 A1 | 10/2006 | Roberts et al. |

| | | | | | | |
|---|---|---|---|---|---|---|
| 2007/0015905 | A1 | 1/2007 | LaColla et al. | WO | WO 01/90121 A3 | 11/2000 |
| 2007/0060503 | A1 | 3/2007 | Gosselin et al. | WO | WO 01/18013 A1 | 3/2001 |
| 2007/0060504 | A1 | 3/2007 | Gosselin et al. | WO | WO 01/92282 A2 | 6/2001 |
| 2007/0203334 | A1 | 8/2007 | Mayes et al. | WO | WO 01/92282 A3 | 6/2001 |

FOREIGN PATENT DOCUMENTS

| | | |
|---|---|---|
| DE | 1 919 307 | 1/1971 |
| DE | 2 122 991 | 11/1972 |
| DE | 2 508 312 | 9/1976 |
| DE | 140254 | 2/1980 |
| DE | 3512781 A1 | 10/1985 |
| DE | 4 224 737 | 2/1994 |
| DE | 102005012681 | 9/2006 |
| EP | 0 288 847 | 4/1988 |
| EP | 0180276 B1 | 12/1988 |
| EP | 0 352 248 | 1/1990 |
| EP | 0350287 A2 | 1/1990 |
| EP | 0 494 119 | 1/1992 |
| EP | 0526655 A1 | 2/1993 |
| EP | 0553358 A1 | 8/1993 |
| EP | 0 587 364 | 3/1994 |
| EP | 0650371 B1 | 5/1995 |
| EP | 0 742 287 | 11/1996 |
| EP | 0 747 389 | 12/1996 |
| FR | 1 521 076 | 4/1968 |
| FR | 1 581 628 | 9/1969 |
| FR | 2 662 165 | 11/1991 |
| GB | 924246 | 4/1963 |
| GB | 984877 | 3/1965 |
| GB | 1187824 | 5/1966 |
| GB | 1163102 | 9/1969 |
| GB | GB 1 163 102 | 9/1969 |
| GB | 1209654 | 10/1970 |
| GB | 1542442 | 3/1979 |
| JP | 71021872 | 3/1968 |
| JP | 48048495 | 9/1971 |
| JP | 61-212592 A2 | 9/1986 |
| JP | 61263995 | 11/1986 |
| JP | 61263996 | 11/1986 |
| JP | 63215694 | 9/1988 |
| JP | 2091022 | 3/1990 |
| JP | 06135988 | 5/1994 |
| JP | 06211890 | 8/1994 |
| JP | 06228186 | 8/1994 |
| JP | 06293645 | 10/1994 |
| JP | 09059292 | 3/1997 |
| WO | WO 89/02733 A1 | 4/1989 |
| WO | WO 90/00555 A1 | 1/1990 |
| WO | WO 91/16920 A1 | 11/1991 |
| WO | WO 91/18914 A1 | 12/1991 |
| WO | WO 91/19721 A1 | 12/1991 |
| WO | WO 92/15308 | 9/1992 |
| WO | WO 92/18517 | 10/1992 |
| WO | WO 93/00910 A1 | 1/1993 |
| WO | WO 94/01117 | 1/1994 |
| WO | WO 94/26273 A1 | 11/1994 |
| WO | WO 96/15132 A1 | 5/1996 |
| WO | WO 98/16184 | 4/1998 |
| WO | WO 99/15194 A1 | 4/1999 |
| WO | WO 99/23104 | 5/1999 |
| WO | WO 99/43691 A1 | 9/1999 |
| WO | WO 99/45016 A2 | 9/1999 |
| WO | WO 99/52514 | 10/1999 |
| WO | WO 99/59621 A1 | 11/1999 |
| WO | WO 99/64016 A1 | 12/1999 |
| WO | WO 00/09531 | 2/2000 |
| WO | WO 00/25799 A1 | 5/2000 |
| WO | WO 00/37110 A2 | 6/2000 |
| WO | WO 00/52015 A2 | 9/2000 |
| WO | WO 00/52015 A3 | 9/2000 |
| WO | WO 01/81359 A1 | 11/2000 |
| WO | WO 01/90121 A2 | 11/2000 |
| WO | WO 01/47935 A2 | 7/2001 |
| WO | WO 01/49700 | 7/2001 |
| WO | WO 01/60315 A2 | 8/2001 |
| WO | WO 01/68663 | 9/2001 |
| WO | WO 01/32153 A2 | 10/2001 |
| WO | WO 01/79246 A2 | 10/2001 |
| WO | WO 01/79246 A3 | 10/2001 |
| WO | WO 01/91737 | 12/2001 |
| WO | WO 01/96353 A2 | 12/2001 |
| WO | WO 02/03997 | 1/2002 |
| WO | WO 02/18404 A2 | 3/2002 |
| WO | WO 02/32414 A2 | 4/2002 |
| WO | WO 02/32920 A2 | 4/2002 |
| WO | WO 02/48165 A2 | 6/2002 |
| WO | WO 02/057287 A2 | 7/2002 |
| WO | WO 02/057425 A2 | 7/2002 |
| WO | WO 02/070533 | 9/2002 |
| WO | WO 02/094289 | 11/2002 |
| WO | WO 02/100415 | 12/2002 |
| WO | WO 03/024461 A1 | 3/2003 |
| WO | WO 03/026589 | 4/2003 |
| WO | WO 03/026675 | 4/2003 |
| WO | WO 03/039523 | 5/2003 |
| WO | WO 03/051899 | 6/2003 |
| WO | WO 03/081899 | 6/2003 |
| WO | WO 03/061385 | 7/2003 |
| WO | WO 03/061576 | 7/2003 |
| WO | WO 03/062255 | 7/2003 |
| WO | WO 03/062256 | 7/2003 |
| WO | WO 03/062257 | 7/2003 |
| WO | WO 03/063771 | 8/2003 |
| WO | WO 03/068162 | 8/2003 |
| WO | WO 03/068164 | 8/2003 |
| WO | WO 03/068244 | 8/2003 |
| WO | WO 03/072757 | 9/2003 |
| WO | WO 03/093290 | 11/2003 |
| WO | WO 03/099840 | 12/2003 |
| WO | WO 03/100017 | 12/2003 |
| WO | WO 03/105770 | 12/2003 |
| WO | WO 03/106577 | 12/2003 |
| WO | WO 2004/000858 | 12/2003 |
| WO | WO 2004/002422 | 1/2004 |
| WO | WO 2004/002999 | 1/2004 |
| WO | WO 2004/003000 | 1/2004 |
| WO | WO 2004/003138 A2 | 1/2004 |
| WO | WO 2004/007512 | 1/2004 |
| WO | WO 2004/009020 A2 | 1/2004 |
| WO | WO 2004/023921 | 3/2004 |
| WO | WO 2004/028481 | 4/2004 |
| WO | WO 2004/041203 | 5/2004 |
| WO | WO 2004/043977 | 5/2004 |
| WO | WO 2004/043978 | 5/2004 |
| WO | WO 2004/044132 | 5/2004 |
| WO | WO 2004/046159 | 6/2004 |
| WO | WO 2004/046331 | 6/2004 |
| WO | WO 2004/052899 | 6/2004 |
| WO | WO 2004/058792 | 7/2004 |
| WO | WO 2004/065398 | 8/2004 |
| WO | WO 2004/072090 | 8/2004 |
| WO | WO 2004/080466 | 9/2004 |
| WO | WO 2004/084796 | 10/2004 |
| WO | WO 2004/096149 | 11/2004 |
| WO | WO 2004/106356 | 12/2004 |
| WO | WO 2005/003147 | 1/2005 |
| WO | WO 2005/012327 | 2/2005 |
| WO | WO 2005/020884 | 3/2005 |
| WO | WO 2005/020885 | 3/2005 |
| WO | WO 2005/021568 | 3/2005 |
| WO | WO 2005/030258 | 4/2005 |

| | | |
|---|---|---|
| WO | WO 2005/042556 | 5/2005 |
| WO | WO 2005/123087 | 12/2005 |
| WO | WO 2006/002231 | 1/2006 |
| WO | WO 2006/012078 | 2/2006 |
| WO | WO 2006/012440 | 2/2006 |
| WO | WO 2006/016930 | 2/2006 |
| WO | WO 2006/037028 | 4/2006 |
| WO | WO 2006/037227 | 4/2006 |
| WO | WO 2006/063717 | 6/2006 |
| WO | WO 2006/065335 | 6/2006 |
| WO | WO 2006/097323 | 9/2006 |
| WO | WO 2006/100087 | 9/2006 |
| WO | WO 2006/121820 | 11/2006 |
| WO | WO 2006/130532 | 12/2006 |
| WO | WO 2007/011777 | 1/2007 |
| WO | WO 2007/025304 | 1/2007 |

OTHER PUBLICATIONS

The Merck Index, (12th edition, 1996, p. 275.*
Sundberg et al, Advanced Organic Chemistry, Part B, 1990, pp. 232 and 236.*
McFarlin et al, J. Am. Chem. Soc. 1958, 80, 5372-76.*
Piccirilli et al , J. Org. Chem. 1999, 64, 747-54; IDS document # HH.*
BeMiller et al Methods in Carbohydrate Chemistry, 1963, 2, 484-485.*
The Merck Index 12th edition, 1996, pp. 274-275.*
Ault , Techniques and Experiments for Organic Chemistry, 5th Edn., 1987, 105-113.*
Sundberg et al Advanced Organic Chemistry, Part B, 1990, pp. 232 and 235-236.*
McFarlin J. Am. Chem. Soc. 1958, 80, 5372-76.*
Piccirilli et al J. Org. Chem. 1999, 64, 747-54.*
Chen et al Heterocycles, 1989, 28(2), 593-601.*
Zemlicka Nucleic Acid Chem., 1991, 4, 183-188.*
Sundberg et al Advanced Organic Chemistry, Part B, Third Edition, p. 146-147.*
Žemlička, J., et al., "Substrate specificity of ribosomal peptidyltransferase. Effect of modification in the heterocyclic, carbohydrate and amino acid moiety of 2'(3')-O-L-phenyladenosine," Biochemistry, 14(24):5239-5249 (Dec. 2, 1975).
Žemlička, J., et al., "Aminoacyl derivatives of nucleosides, nucleotides, and polynucleotides. VIII. The preparation of 2'(3')-O-L-phenylalanyluridine, -cytidine, -adenosine, -inosine, -guanosine and 2'-deoxy-3'-O-L-phenylalanyladenosine," Collection Czechoslov., Chem. Commun., 43(13):3755-3767 (1969).
Baginski, S. G, et al., "Mechanism of action of a pestivirus antiviral compound," PNAS USA, 97(14) : 7981-7986(2000).
Battaglia, A.M. et al., "Combination Therapy with Interferon and Ribavirin in the Treatment of Chronic Hepatitis C Infection", Ann. Pharmacother, 34:487-494 (2000).
Beigelman, L.N., et al., "Functionally complete analogues of nucleosides. The use of D-glucose for the synthesis of 2-C-methyl-D-ribose derivatives and related nucleosides," Bioorg, Khim., 12(10):1359-1365 (1986). Abstract in English at p. 1365.
Beigelman, L.N., et al., "New synthesis of 2'-C-methylnucleosides starting from D-glucose and D-ribose," Carbohydrate Research, 166:219-232 (1987).
Benzaria, S., et al., "Synthesis of potential prodrugs of β-L-dC, a potent and selective anti-HBV agent," Antiviral Res., 50:A79 (2001).
Berenguer, M. et al, "Hepatitis C virus in the transplant setting", Antivir. Ther., 3 (Suppl 3):125-136 (1998).
Berman, E, et al., "Synergistic cytotoxic effect of azidothymidine and recombinant interferon alpha on normal human bone marrow progenitor cells ," Blood, 74(4):1281-1286 (1989).
Bhat et al. (Oral Session V, Hepatitis C Virus, Flaviviridae, 2003 (Oral Session V, Hepatitis C Virus, Flaviviridae; 16$^{th}$ International Conference on Antiviral Research (Apr. 27, 2003, Savannah, Ga.); p. A75).
Browne, M.J., et al., "2',3'-didehydro-3'-deoxythymidine (d4T) in patients with AIDS or AIDS-Related Complex: A Phase I trial," J. Infect. Dis., 167(1):21-29 (1993).

Bryant, M.L., et al., "Antiviral L-nucleosides specific for hepatitis B virus infection," Antimicrobial Agents and Chemotherapy, 45(1):229-235 (Jan. 2001).
Cavelier, F., et al., "Studies of selective Boc removal in the presence of silyl ethers," Tetrahedron Letters, 37:5131-5134 (1996).
Colacino, J. M., "Review article: Mechanisms for the anti-hepatitis B virus activity and mitochondrial toxicity of fialurdine (FIAU)," Antiviral Res., 29(2-3): I25-39 (1996).
Cretton-Scott, E., et al., "Pharmacokintetics of β-L-2'-deoxycytidine prodrugs in monkeys," Antiviral Res., 50:A44 (2001).
Cui, L., et al., "Cellular and molecular events leading to mitochondrial toxicity of 1-(2-deoxy-2-fluoro-1-β-D-arabinofuranosyl)-5-iodouracil in human liver cells," J. Clin. Invest., 95:555-563 (1995).
Davis, G.L., "Current therapy for chronic Hepatitis C," Gastroenterology118:S104-S114 (2000).
De Francesco, R., et al., "Approaching a new era for hepatitis C virus therapy: inhibitors of the NS3-4A serine protease and the NS5B RNA-dependent RNA polymerase," Antiviral Research, 58: 1-16 (2003).
De Lombaert, S., et al., "N-Phosphonomethyl dipeptides and their phosphonate prodrugs, a new generation of neutral endopeptidase (NEP, EC 3.4.24.11) inhibitors," J. Med. Chem., 37:498-511 (1994).
Dornsife, R.E., et al, "In vitro potency of inhibition by antiviral drugs of hematopoietic progenitor colony formation correlates with exposure at hemotoxic levels in Human Immuno-deficiency Virus-positive humans," Antimicrob. Agents Chemother., 40(2):514-519 (1996).
Dymock, B.W., et al., "Review: Novel approaches to the treatment of hepatitis C virus infection," Antiviral Chemistry & Chemotherapy, 11(2):79-95 (2000).
Eldrup et al. (Oral Session V, Hepatitis C Virus, Flaviviridae; 16$^{th}$ International Conference on Antiviral Research (Apr. 27, 2003, Savannah, Ga.).
Farkas, J., et al., "Nucleic acid components and their analogues. XCIV. Synthesis of 6-amino-9-(1-deoxy-β-D-psicofuranosyl)purine", Collect. Czech. Chem. Commun. 32:2663-2667 (1967).
Farkas, J., et al., "Nucleic acid components and their analogues. LXXIX. Synthesis of methyl 1-deoxy-D-psicofuranosides substituted at $C_{(1)}$ with halo atoms or a mercapto group," Collect. Czech. Chem. Commun., 31:1535-1543 (1996).
Farquhar, D., et al., "Synthesis and biological evaluation of neutral derivatives of 3-fluoro-2'-deoxyuridine 5'-phosphate," J. Med Chem. 26: 1153 (1983);.
Farquhar, D., et al., "Synthesis and biological evaluation of 9-[5'-(2-oxo-1,3,2-oxazaphosphorinan-2-yl)-β-D-arabinosyl]adenine and 9-[5'-(2-oxo-1,3,2-dioxazaphosphorinan-2-yl)-β-D-arabinosyl]adenine: Potential neutral precursors of 9-[β-D-arabinofuranosyl]adenine 5'-monophosphate," J. Med. Chem. 28:1358-1381 (1985).
Feast, A.A.J., et al., "Studies on the D-glucosaccharinic acids," Acta Chemica Scandinavica 19(5):1127-1134 (1965).
Ferrari R., et al., "Characterization of soluble hepatitis C virus RNA-dependent RNA polymerase expressed in Escherichia coli ," Journal of Virology, 73(2), 1649-1654 (1999).
Fischl, M.A., et al., "Zalcitabine compared with zidovudine in patients with advanced HIV-1 infection who received previous zidovudine therapy," Ann. Intern. Med., 18(10):762-769 (1993).
Freed, J.J., et al., "Evidence for acyloxymethyl esters of pyrimidine 5'-deoxyribonucleo-tides as extracellular sources of ative 5'-deoxyribonucleotides in cultured cells," Biochemical Pharmacology. 38:3193-3198 (1989).
Gunic, E., et al., "Synthesis and cytotoxicity of 4'-C-and 5'-C-substituted Toyocamycins," Bioorg. Med. Chem., 9:163-170(2001).
Harry-O'Kuru, R.E. , J.M. Smith, and M.S. Wolfe, "A short, flexible route toward 2'-C-branched ribonucleosides", J.Org. Chem. 62, 1754-1759 (1997). (Scheme 11).
Hostetler, K.Y., et al., "Synthesis and antiretroviral activity of phospholipids analogs of azidothymidine and other antiviral nucleosides," J. Biol. Chem., 265:6112-6117 (Apr. 15, 1990).
Hostetler, K.Y., et al., "Greatly enhanced inhibition of Human Immunodeficiency Virus Type I replication in CEM and HT4-6C cells by 3'-deoxythymidine diphosphate dimyristoylglycerol, a lipid prodrug of 3'-deoxythymidine," *Antimicrob. Agents Chemother.*, 36:2025.2029 (Sep. 1992).

Hunston, R.N., et al., "Synthesis and biological properties of some cyclic phosphotriesters drived from 2'-deoxy-5-fluorouridine," *J. Med. Chem.* 27:440-444 (1984).

Jones, G. H., and Moffatt,, J. G., "[55] Oxidation of carbohydrates by the sulfoxide-carbodiimide and related methods: Oxidation with dicyclohexylcarbodiimide-DMSO, diisopropylcarbodiimide-DMSO, acetic anhydride-DMSO, and phosphorus pentaoxide-DMSO," *Methods in Carbohydrate Chemistry*; Whisler; R. L. and Moffatt, J. L. Eds; Academic Press: New York, 1972; 315-322.

Jones, G. H., et al., "4'-substituted nucleosides. 5. Hydroxymethylation of nucleoside 5'-aldehydes," *J. Org. Chem.*, 44:1309-1317 (1979).

Kempe, T., et al., "Selective 2'-benzoylation at the cis 2',3'-diols of protected ribonucleosides. New solid phase synthesis of RNA and DNA-RNA mixtures," *Nucleic Acids Res.*, 10(21):6695-6714 (Nov. 11, 1982).

Kerr, S.G., et al., "$N^4$-(dialkylamino)methylene derivatives of 2'-deoxycytidine and arabinocytidine: physicochemical studies for potential prodrug applications," *J. Pharm. Sci.*, 83(4):582-586 (Apr. 1994).

Khamnei, S., "Neighboring group catalysis in the design of nucleotide prodrugs," *J. Med. Chem.*, 39:4109-4115 (1996).

Kiliani, H., "Ueber Saccharin und Saccharinsäure," *Chemische Berichte*, 15:2953 (1882). In German. Partial translation in English at pp. 43-44 of the SOWDEN reference.

Kohn, P., et al., "A new method for the synthesis of furanose derivatives of aldohexoses," *J. Am. Chem. Soc.*, 87(23):5475-5480 (Dec. 5, 1965).

Kucera, L.S., et al., "Novel membrane-interactive ether lipid analogs that inhibit infectious HIV-1 production and induce defective virus formation," *AIDS Res. Hum. Retro Viruses*, 6:491-501 (1990).

Kurtzberg J., et al., "Differential toxicity of carbovir and AZT to human bone marrow hematopoietic progenitor cells in vitro," *Exp. Hematol.*, 18(10):1094-1096 (1990).

Leonard, N. J., et al., "5-Amino-5-deoxyribose derivatives. Synthesis and use in the preparation of "reversed" nucleosides" *J. Heterocycl. Chem.*, 3:485-489 (Dec. 1966).

Lerza, R, et al., "In vitro synergistic inhibition of human bone marrow hemopoietic progenitor growth by a 3'-azido-3'-deoxy-thymidine, 2',3'-dideoxycytidine combination," *Exp. Hernatol.*, 25(3):252-255 (1997).

Lewis, W., et al., "Zidovudine induces molecular, biochemical, and ultrastructural changes in rat skeletal muscle mitochondria," *J. Clin. Invest.*, 89(4):1354-1360 (1992).

Lewis, L. D., et al., "Ultrastructural changes associated with reduced mitochondrial DNA and impaired mitochondrial function in the presence of 2'3'-dideoxycytidine," *Antimicrob. Agents Chemother.*, 36(9):2061-2065 (1992).

Lewis, W., et al., "Fialuridine an dits metabolites inhibit DNA polymerase γ at sites of ultiple adjacent analog incorporation, decrease mtDNA abundance, and cause mitochondrial structural defects in cultured hepatoblasts," *Proceedings of the National Academy of Sciences, USA*, 93(8): 3592-7 (1996).

Li, N.-S., et al., "2'-C-branched ribonucleosides. 2. Synthesis of 2'-C-β-trifluoromethyl pyrimidine ribonucleosides," *Organic Letters*,3(7):1025-1028 (2001).

Lohmann V., et al., "Biochemical and kinetic analyses of NS5B RNA-dependent RNA polymerase of the Hepatitis C virus," *Virology*, 249, 108-118 (1998).

Lopez-Herrera, F.J., et al., "A new synthesis of 2-C-methyl-D-ribono-1,4-lactone and the C-(/C-13 frament of methynolide," *J. Carbohydrate Chemistry*, 13(5):767-775 (1994).

Lopez Aparicio, F.J., et al., "Synthesis of saccharinic acid derivatives," *Carbohydrate Res.*, 129:99(1984).

Luh, T.-Y., at al., "A convenient method for the selective esterification of amino-alcohols," *Synthetic Communications*, 8(5):327-333 (1978).

McCormick, J., et al., "Structure and total synthesis of HF-7, a neuroactive glyconucleoside disulfate from he funnel-web spide *Hololena curta*," *J. Am. Chem. Soc.*, 121(24), 5661-5664 (1999).

McKenzie, R., at al., "Hepatic failure and lactic acidosis due to fialuridine (FIAU), an investigational nucleoside analogue for chronic hepatitis B", *N. Engl. J. Med.*, 333(17):1099-1105 (1995).

Medina, D. J., at al., "Comparison of mitochondrial morphology, mitochondrial DNA content, and cell viability in cultured cells treated with three anti-Human Immunodeficiency Virus dideoxynucleosides," *Antimicrob. Agents Chemother.*, 38(8):1824-8 (1994).

Meier, C., et al., "Cyclic saligenyl phosphotriesters of 2',3'-dideoxy-2',3'-didehydrothymidine (d4T)—A new pro-nucleic approach." *Bioorganic & Med. Chem. Letters* 7(2):99-104 (1997).

Meyer, R.B., Jr., et al., "2'-O-Acyl-6-thioinosine cyclic 3',5'-phosphates as prodrugs of thioinosinic acid," *J. Med. Chem.* 22: 811-815 (1979).

Neidlein, R., et al., "Mild preparationof 1-benzyuloxyiminoalkylphosphonic dichlorides: Application to the synthesis of cyclic phosphonic diesters and cyclic monoester amides," *Heterocycles* 35:1185-1203 (1993).

Novák, J.J.K. & Sorm, F., "Nucleic acid components and their analogues. CXX. 2-C-methyl-D-ribose and tis derivatives," *Collection Czechoslov. Chem. Commun.*, 34:857-866 (1969).

Novák, J.J.K., "Chiroptical properties of 2-methyl-1,4-lactones; revised absolute configuration of 2-deoxy-2-C-methyl-*erythro*-D-pentono-1,4-lactones," *Collection Czechoslov. Chem. Commun.*, 39:869-882 (1974).

Nutt, R.F., et al., "Branched-chain sugar nucleosides. III. 3'-C-methyladenine", *J.Org. Chem.*, 33:1789-1795 (1968).

Olsen, et al. (Oral Session V. Hepatitis C Virus, Flaviviridae; 16th International Conference on Antiviral Research (Apr. 27, 2003, Savannah, Ga.) p. A76).

Pan-Zhou, X-R, et al.,"Differential effects of antiretroviral nucleoside analogs on mitochondrial function in HepG2 cells," *Antimicrob. Agents Chemother.* 44:496-503 (2000).

Piantadosi, C., et al., "Synthesis and evaluation of novel ether lipid nucleoside conjugates for anti-HIV-1 activity," *J. Med. Chem.* 34:1408-1414 (1991).

Pierra, C., et al., "Comparative studies of selected potential prodrugs of β-L-dC, a potent and selective anti-HBV agent," *Antiviral Res.*, 50:A79 (2001), Abstract No. 138.

Richman, D.D., et al., "The toxicity of azidothymidine (AZT) in the treatment of patients with AIDS and AIDS-Related Complex," *N. Engl. J. Med.*, 317(4):192-197 (1987).

Scheibler, C., "Ueber das Saccharin und die Saccharinsäure," *Chemische Berichte*, 13:2212-2217 (1880). In German.

Sommadossi J-P, et al., "Comparison of cytotoxicity of the (−)- and (+)- enantiomer of 2',3'-dideoxy-3'-thiacytidine in normal human bone marrow progenitor cells," *Biochemical Pharmacology* 44(10):1921-1925 (1992).

Sommadossi J.-P., et al., "Toxicity of 3'-azido-3'-deoxythymidine and 9-(1,3-dihydroxy-2-propoxymethyl)guanine for normal human hematopoietic progenitor cells in vitro," *Antimicrobial Agents and Chemotherapy*, 31:452-454 (1987).

Sowden, J., "The Saccharinic Acids," *Adv. Carbohydrate Chem.*, 12:43-46(1957).

Standring, D.N., et al., "Antiviral beta-L-nucleosides specific for hepatitis B virus infection," *Antiviral Chem. & Chemother.*, 12 (Suppl. 1):119-129 (2001).

Starrett, J.E.Jr., et al., "Synthesis, oral bioavailability determination, and in vitro evaluation of prodrugs of the antiviral agents 9-(2-(phosphonomethoxy)ethyl]adenine (PMEA)," *J. Med. Chem.* 37: 1857-1864 (1994).

Tang, X.-Q., et al, "2'-C-branched ribonucleosides: Synthesis of the phophoramidite derivatives of 2'-C-β-methylcytidine and their incorporation into oligonucleotides," *J. Org. Chem.*, 64(3):747-754 (1999).

Walton, E., et al., "Branched-chain sugar nucleosides. A new type of biologically active nucleoside," *J. Am. Chem. Soc.*, 88(19):4524-4525 (Oct. 5, 1966).

Weinberg, R.S., et al., "Effect of antiviral drugs and hematopoietic growth factors on in vitro erythropoiesis," *Mt. Sinai J. Med.* 1998;65(1):5-13.

Whistler, R.L., and BeMiller, J.N., "[118] 'α'-D-Glucosaccharino-1,4-lactone," *Methods in Carbohydrate Chemistry*, 2:484-485 (1963).

Yarchoan, R., et al. "Long-term toxicity / activity profile of 2',3'-dideoxyinosine in AIDS or AIDS-related complex," *The Lancet*, 336(8714):526-529 (1990).

Yoshida Y, et al., "Reversal of azidothymidine-induced bone marrow suppression by 2',3'-dideoxythymidine as studied by hemopoietic clonal culture," *AIDS Res. Hum. Retroviruses*, 6(7):929-932 (1990).

ZON, G., "Cyclophosphamide Analogues," Chapter 4 in *Progress in Medicinal Chemistry*, vol. 19, G.P. Ellis and G.B. West, Eds., pp. 205-246 (1982).

U.S. Appl. No. 10/845,976, filed May 14, 2004, Storer, et al.

U.S. Appl. No. 11/005,443, filed Dec. 6, 2004, Gosselin, et al.

U.S. Appl. No. 11/516,928, filed Sep. 6, 2006, Sommadossi, et al.

Alt, et al., "Core Specific Antisense Phosphorothioate Oligodeoxynucleotides as Ptent and Specific Inhibitors of Hepatitis C Viral Translation." Arch. Virol. (1997) 142: 589-599.

Alt, et al., "Specific inhibition of hepatitis C viral gene expression by antisense phosphorothioate oligodeoxynucleotides," Hepatology, 22:707-717 (1995).

Altmann, et al., "The Synthesis of 1'-Methyl Carbocyclic Thymidine and Its Effect on Nucleic Acid Duplex Stability," Synlett, Thieme Verlag. Stuttgart, De, 10:853-855 (1994).

Awano, et al., "Nucleosides and Nucleotides, Part 144 Synthesis and Antiviral Activity of 5-Substituted (2's)-2'-Deoxy-2'—C-Methylycytidines and—Urdines," Archiv Der Pharmazie, VCH Verlagsgesellschaft Mbh, Weinheim, DE, vol. 329, Feb. 1, 1996, pp. 66-72.

Beigelman, et al., "A general method for synthesis of 3'—alkylnucleosides," Nucleic Acids Symp. Ser., vol. 9, 1981, pp. 115-118.

Beigelman, et al., *Carbohydrate Res.*, 1987, 166: 219-232.

Beigelman, et al., "Epimerization During the Acetolysis of: 3-O-Acetyl-5-O-Benzoyl-1,2-o-Isopropylidene-3-C-Methyl-a, D-Ribofuranose. Synthesis of 3'-C-Methylnucleosides with the B-D-ribo-and a-D-arabino Configurations," Carbohydrate Research, 181:77-88 (1988).

Berenguer, M., et al., "Hepatitis B and C viruses: Molecular identification and targeted antiviral therapies," Proccedings of the Association of American Physicians, 110(2), 98-112 (1998).

Bhopale, Girish Mahadeorao, et al., "Emerging drugs for chronic hepatitis C," Hepatology Research (2005), 32(3), 146-153.

Bianco, et al., "Sythesis of a New Carbocyclic Nucleoside Analog." *Tetrahedron Letters*, 38(36): 6433-6436.

Billich, et al., "Nucleoside Phosphotransferase from Malt Sprouts." Biol. Chem. Hoppe-Seyler, vol. 367, pp. 267-278. Apr. 1986.

Bio, et al., "Practical Synthesis of a Potent Hepatitis C Virus RNA Replication Inhibitor." Journal of Organic Chemistry (2004), 69(19), 6257-6266.

Bloch, A., et al., "The Role of the 5'-Hydroxyl Group of Adenosine in Determining Substrate Specificity for Adenosine Deaminase," J. Med. Chem., 10(5):908-12 (Sep. 1967).

Boryski, et al., "Synthesis and Antiviral Activity of 3-Substituted Derivatives of 3,9-Dihydro-9-0xo-5H-Imidazo[1,2-a]Purines, Tricyclic Analogues of Acyclovir and Ganciclovir." *J. Med. Chem.*, 34, 2380-2383.

Brown & McFarlin, et al., J. Am. Chem. Soc. 1958, 80, 5372-76.

Cappellacci, et al. "Ribose-modified nucleosides as ligands for adenosine receptors: Synthesis, conformational analysis, and biological evaluation of 1'—C-methyl denosine analogues," J. Med. Chem., vol. 45, 2002, pp. 1196-1202.

Cappellacci, et al. "Synthesis, Biological Evaluation, and Molecular Modeling of Ribose-Modified Adenosine Analogues as Adenosine Receptor Agonists." Journal of Medicinal Chemistry (2005), 48(5), 1550-1562.

Carroll, S.S., et al., "Inhibition of hepatitis C virus RNA replication by 2'-modified nucleoside analogs," *J. Biol. Chem.*, 278(14): 11979-11984 (2003).

Carroll, S.S., "Nucleoside analog inhibitors of hepatitis C virus replication," Infectious Disorders: Drug Targets (2006), 6(1), 17-29.

Chand, Pooran; et al., "Synthesis of (2S,3S,4R,5R)-2-(4- amino-5H-pyrrolo[3,2-d]pyrimidin-7-yl)-5- (hydroxymethyl)-3-methylpyrrolidine-3,4-diol, an analog of potent HCV inhibitor." Collection Symposium Series (2005), 7(Chemistry of Nucleic Acid Components), 329-332.

Chang, et al., *J. Biol. Chem.*, 1992, 267(20): 13938-42.

Chiacchio, et al., "Stereoselective synthesis of 2'-amino-2',3'dideoxynucleosides by nitrone 1,3-dipolar cycloaddition: A new efficient entry toward d4T and its 2-methyl analougue," J. Org. Chem., vol. 64, 1999, pp. 28-36.

Chiaramonte, et al., "Inhibition of CMP-Sialic Acid Transport into Golgi Vesicles by Nucleoside Monophates." Biochemistry 2001, 40, 14260-14267.

Clark, et al., "Design, Synthesis, and Antiviral Activity of 2'-Deoxy-2'-fluoro-2'-C-methylcytidine, a Potent Inhibitor of Hepatitis C Virus Replication." Journal of Medicinal Chemistry (2005), 48(17), 5504-5508.

Coelmont, Lotte, "Ribavirin antagonizes the in vitro anti-hepatitis C virus activity of 2'-C-methycytidine, the active component of valopicitabine," Antimicrobial Agents and Chemotherapy (2006), 50(10), 3444-3446.

Cook, G.S., "Improving the treatment of hepatitis C infection in the UK," Expert Opinion on Pharmacotherapy, (2007) vol. 8, No. 2, pp. 183-191.

Cornberg, M., et al., "Present and future therapy for hepatitis C virus," Expert review of Anti-Infective Therapy, (2006) vol. 4, No. 5, pp. 781-793.

Czernecki, S., et al., "Synthesis of 2'-deoxy-2'-spirocyclopropyl cytidine as potential inhibitor of ribonucleotide diphosphate reductase," Can. J. Chem., vol. 71, 1993, pp. 413-416.

Czernecki, S., et al., "Synthesis of various 3'-branched 2', 3'-unsaturated pyrimidine nucleosides as potential anti-HIV agents," J. Org. Chem., 57: 7325-7328 (1992).

Dalpiaz, et al., "Temperature dependence of the affinity enhancement of selective adenosine A1 receptor agonism: a thermodynamic analysis." European Journal of Pharmacology (2002), 448(2-3), 123-131.

Davis, G.L., "New Therapies: Oral Inhibitors and Immune Modulators," Clinics in Liver Disease, (2006) vol. 10, No. 4, pp. 867-880.

Davisson, V.J., et al., "Synthesis of Nucleotide 5'-Diphosphates from 5'-O-Tosyl Nucleosides," J. Org. Chem., 52(9):1794-1801 (1987).

Ding, et al., "Synthesis of 2'-β-C-methyl toyocamycin and sangivamycin analogs as potential HCV inhibitors." Bioorganic & Medicinal Chemistry Letters (2005), 15(3), 725-727.

Ding, et al., "Synthesis of 9-(2-β-C-methyl-β-D-ribofuranosyl)-6-substituted purine derivatives as inhibitors of HCV RNA replication." Bioorganic & Medicinal Chemistry Letters (2005), 15(3), 709-713.

Dutartre, H., et al., "General catalytic deficiency of hepatitis C virus RNA polymerase with an S282T mutation and mutually exclusive resistance towards 2'-modified nucleotide analogues," Antimicrobial Agents and Chemotherapy, (2006) vol. 50, No. 12, pp. 4161-4169.

Eldrup, et al., "Structure-Activity Relationship of Heterobase-Modified 2'-C-Methyl Ribonucleosides as Inhibitors of Hepatitis C Virus RNA Replication." Department of Medicinal Chemistry, Isis Pharmaceuticals, Carlsbad, CA, USA. Journal of Medicinal Chemistry (2004), 47(21), 5284-5297.

Eldrup, et al., "Structure-Activity Relationship of Purine Ribonucleosides for Inhibition of Hepatitis C Virus RNA-Dependent RNA Polymerase.", Department of Medicinal Chemistry, Isis Pharmaceuticals, Carlsbad, CA, USA. Journal of Medicinal Chemistry (2004), 47(9), 2283-2295.

Fahrquhar, et al., *J. Pharm. Sci.*, 1983, 72(3): 324.

Faivre-Buet, et al., "Synthesis of 1'-Deoxypsicofuanosyl-Dexoynucleosides as Potential Anti-HIV Agents." Nucleosides & Nucleotides, vol. 11, No. 7, 1992, pp. 1411-1424.

Fedorov, et al., "3'—C-Branched 2'—deoxy-5-methyluridines: Synthesis, enzyme inhibition, and antiviral properties," J. Med. Chem., vol. 35, 1992, pp. 4567-4575.

Fox, J. J., et al., "Thiolation of nucleosides. II. Synthesis of 5-methyl-2'-deoxycytidine and related pyrimidine nucleosides," J. Am. Chem. Soc., 81: 178-187 (Jan. 5, 1959).

Franchetti, et al., "2'—C-Methyl analogues of selective adenosine receptor agonists: Synthesis and binding studies," J. Med. Chem., vol. 41, 1998, pp. 1708-1715.

Franchetti, et al., "Antitumor Activity of C-Methyl-β-D-ribofuranosyladenine Nucleoside Ribonucleotide Reductase Inhibitors." Journal of Medicinal Chemistry (2005), 48(15), 4983-4989.

Fujimori, et al., "A Convenient and Stereoselective Synthesis of 2'-Deoxy-[beta]-L-nucleosides," Nucleosides & Nucleotides, 11(2-4), 341-349 (1992); only CAPLUS abstract supplied.

Furukawa, Y., et al. "A novel method for synthesis of purine nucleosides using Friedel-Crafts catalysts," Chem. Pharm. Bull., 16(6):1076-1080 (Jun. 1968).

Galderisi, U., et al., "Antisense oligonucleoties as therapeutic agents," Journal of Cellular Physiology, 181(2):251-257 (Nov. 1999).

Gallo, et al., "2'-C-Methyluridine Phosphoramidite: A New Building Block for the Preparation of RNA Analogues Carrying the 2'-hydroxyl Group." Tetrahedron, 57 (2001), 5707-5713.

Girardet, et al., "Synthesis and Cytotoxicity of 4-Amino-5-oxopyrido[2,3-d]pyrimidine Nucleosides." Journal of Medicinal Chemistry (2000), 43(20), 3704-3713.

Gretch, D.R., "Use and interpretation of HCV diagonostic tests in the clinical setting." Clinics in Live Disease, Nov. 1997, vol. 1, No. 3, pp. 547-557.

Grouiller, et al., "Novel-p-toluensesulfaonylation and Thionocarbonylation of Unprotected Thymine Nucleosides," *Synlett*, 1993: 221-222 (1993).

Grouiller, et al., "Structural studies on a psicofuranosyl nucleoside, a potential antiviral agent." J. Pharm. Belg., 47(4), 381-3 (1992).

Grunnagel, et al., "Preparation of D-Tagatose." Justus Liebigs Annalen der Chemie (1969), 721: 234-5.

Haraguchi, et al., "Preparation and Reactions of 2'-and 3'—Vinyl Bromides of Uracil Nucleosides: Versatile Synthons for Anti-HIV Agents," *Tetrahedron Letters*, 32(28): 3391-94 (1991).

Haraguchi, et al., "Stereoselective Synthesis of 1'-C-Branched Uracil Nucleosides from Uridine," *Nucleotides & Nucleosides*, 14(3-5): 417-420 (1995).

Harry-O'Kuru, et al., "2'-C-alkylribonucleosides: Design, Synthesis and Conformation," *Nucleosides & Nucleotides*, vol. 16: 1457-60 (1997).

Hassan, et al., "Nucleosides and Nucleotides 151: Conversion of (Z)-2'-(Cyanomethylene)-2'-Deoxyuridines into their (E)-Isomers via Addition of Thiophenol to the Cyanomethylene Moiety Followed by Oxidative Syn-elimination Reactions." J. Org. Chem., vol. 61, 1996, pp. 6261-6267.

Hassan, et al., "Nucleosides and Nucleotides 156: Chelation-Controlled and Nonchelation-Controlled Diastereofacial Selective Thiophernol Addition Reactions at the 2'-Position of 2'-[(Alkoxycarbonyl)methaylene]-2'-deoxyuridines: Conversion of (Z0-2'[(Alkoxycarbonyl)methylene]-2'-Deoxyuridines into their (E)-Isomers" J. Org. Chem., vol. 62, 1997, pp. 11-17.

Hattori, H., et al., "Nucleosides and Nucleotides 175. Structural requirements of the sugar moiety for the antitumor activities of new nucleoside antimetabolites, 1-(3-C-ethynyl-b-D-ribopentofuranosyl)cytosine and—uracil," *J. Med. Chem.*, 41: 2892-2902 (1998).

Hayakawa, et al., "Reaction of organometallic reagents with 2'- and 3'-ketouridine derivatives: synthesis of uracil nucleosides branched at the 2'- and 3'-positions." Chemical & Pharmaceutical Bulletin (1987), 35(6), 2605-8.

Hoard, D.E., et al., "Conversion of Mono- and Oligodeoxyribonucleotides to 5'-Triphosphates," J. Am Chem. Soc., 87(8):1785-1788 (Apr. 20, 1965).

Hodge, et al., "Amadori Rearrangement Products." Methods in Carbohydrate Chemistry (1963), 2: 99-107.

Holy, A., "Nucleic Acid Components and Their Analogs. CLIII. Preparation of 2'-deoxy-L-Ribonucleosides fo the Pyrimidine Series," Collect. Czech. Chem. Commun., 37(12): 4072-4087 (1972).

Hossain, et al., "Synthesis of 2'- and 3'-Spiro-isoxazolidine Derivatives of Thymidine & Their Conversions to 2',3'-dideoxy-2', 3'-didehydro-3'-C-substituted nucleosides by Radical Promoted Fragmentation," Tetrahedron vol. 49, No. 44, pp. 10133-10156, (1993).

Hrebabecky, et al., "Nucleic Acid Components and their Analogs: CXLIX: Synthesis of Pyrimidine Nucleosides Derived from 1-Deoxy-D-Psicose," *Coll Czech Chem Com.* 37: 2059-2064 (1974).

Hrebecky, et al., "Synthesis of 7- and 9b-D-Psicofuranosylguanine and Their 1'-Deoxy Derivatives." Collection Czechoslov. Chem. Commun., vol. 39, 1974, pp. 2115-2123.

Iglesias, et al., "Complete and Regioselective Deacetylation of Peracetylated Uridines Using a Lipase." Biotechnology Letters 22: 361-365, 2000.

Iimori, et al., "2'-C-, 3'-C-, and 5'-C-Methylsangivamycins: conformational lock with the methyl group." Tetrahedron Letters (1991), 32(49), 7273-6.

Iimori, et al., "A study on conformationally restricted sangivamycins and their inhibitory abilities of protein kinases." Nucleic Acids Symposium Series (1992), 27(Nineteenth Symposium on Nucleic Acids Chemistry, 1992), 169-70.

Iino, T., et al., "Nucleosides and nucleotides 139. Stereoselective synthesis of (2'S)-2'-C-alkyl-2'-deoxyuridines," Nucleosides & Nucleotides, 15(1-3): 169-181 (1996).

Ikegashira, K., et al., "Discovery of conformationally constrained tetracylic compounds as potent hepatitis C virus NS5B RNA polymerase inhibitors," Journal of Medicinal Chemistry, (Nov. 30, 2006) vol. 449, No. 24, pp. 6950-6953.

Imai, K., et al., "Studies on Phosphorylation. IV. Selective Phosphorylation of the Primary Hydroxyl Group in Nucleosides." J. Org. Chem., 34(6): 1547-1550 (Jun. 1969).

Itoh, et al., "Divergent and Sterocontrolled Approach to the Synthesis of Uracil Nucleosides Branched at the Anomeric Position," J Org Chem, 60(3): 656-662 (1995).

Johnson, C.R., et al., "3'—C-Trifluoromethyl ribonucleosides," Nucleosides & Nucleotides, vol. 14, 1995, pp. 185-194.

Kakefuda, et al., "Nucleosides and nucleotides. 120. Stereoselective radical deoxygenation of tert-alcohols in the sugar moiety of nucleosides: synthesis of 2',3'-dideoxy-2'-C-methyl- and -C-ethynyl-β-D-threo-pentofuranosyl pyrimidines and adenine as potential antiviral and antitumor agents." Tetrahedron (1993), 49(38), 8513-28.

Kamaike, K., et al., "An efficient method for the synthesis of [4-15N]cytidine, 2'-deoxy[4-15N]cytidine, [6-15N]adenosine, and 2'-deoxy[6-15N]adenosine derivatives," Nucleosodies and Nucleotides, 15(1-3$_{13}$ : 749-769 (1996).

Kaneko, M., et al., "A convenient synthesis of cytosine nucleosides," Chem. Pharm. Bull., 20:1050-1053 (1972).

Kawana, et al, "The Deoxygenatio of Tosylated Adenosine Derivatives with Grignard Reagents," Nucleic Acids Symp Ser, 17:37-40 (1986).

Kim, et al., "A Novel Nucleoside Prodrug-Activating Enzyme: Substrate Specificity of Biphenyl Hydrolase-like Protein," Molecular Pharmaceutics (2004), 1(2), 117-127.

Klumpp, et al., "The Novel Nucleoside Analog R1479 (4'-Azidocytidine) is a Potent Inhibitor of NS5B-dpendent RNA Synthesis and Hepatits C Virus Replication in Cell Culture." The Journal of Biological Chemistry, vol. 281, No. 7, pp. 3793-3799, Feb. 17, 2006.

Kohn, et al., *J. Am. Chem. Soc.*, 1965, 87(23): 5475-80.

Kotra, L., et al., "Structure-Activity Relationships of 2'-Deoxy-2',2'-difluoro-L-erythro-pentofuranosyl Nucleosdes." J. Med. Chem. 1997, 40, 3635-3644.

Kuhn, R., et al., "Uber eine molekulare Umlagerung von N-Glucosiden." Jahrg. 69, 1936, p. 1745-1754.

Lai, V.C.H., et al., "Mutational analysis of bovine viral diarrhea virus RNA-dependant RNA polymerase," J. Virol., 73(12):10129-101136(Dec. 1999).

Landowski, "Nucleoside ester prodrug substrate specificity of liver carboxylesterase," Journal of Pharmacology and Experimental Therapeutics (2006), 316(2), 572-580.

Lavaire, S., et al., "3'-deoxy-3'-C-trifluoromethyl nucleosides: Synthesis and antiviral evaluation," *Nucleosides & Nucleotides*, 17(12): 2267-2280 (1998).

Le Pogam, et al., "In Vitro Selected Conl Subgenomic Replicons Resistant to 2'-C-Methyl-Cytidine or to R1479 Show Lack of Cross Resistance." Virology 351 (2006), 349-359.

Le Pogam, et al., "Selection and Characterization of Replicon Variants Dually Resistant to Thumb- and Palm-Binding Nonnucleoside Polymeras Inhibitors of the Hepatitis C Virus." Journal of Virology, vol. 80, No. 12, Jun. 2006, p. 6146-6154.

Leyssen, P., et al., "Perspectives for the treatment of infections with Flaviviridae," *Clinical Microbiology Reviews* (Washington D.C.) 13(1): 67-82 (Jan. 2000).

Lin, T.S., et al., "Synthesis of Several Pyrimidine L-Nucleoside Analogues as Potential Antiviral Agents," Tethrahedron Letters, 51(4): 1055-1068 (1995).

Luh, et al. *Synthetic Communications*, 1978, 8(5): 327-33.

Maga, Giovanni, et al., Lack of stereospecificity of suid pseudorabies virus thymidine kinase, Biochem. J., 294(2): 381-385 (1993).

Mahmoudian, M., et al., "A Versatile Procedure for the Generation of Nucleoside 5'-Carboxylic Acids Using Nucleoside Oxidase," Tetrahedron, Elsevier Science Publishers Amsterday, NL, vol. 54, No. 28, Jul. 9, 1998.

Mansour, T.S., et al., "Editorial," Anti-Ineffective Agents in Medicinal Chemistry, (2007) vol. 6, No. 1, pp. 1.

Markland W., et al., "Broad-spectrum antiviral activity of the IMP dehydrogenase inhibitor VX-497: a comparison with ribavirin and demonstration of antiviral additivity with alpha interferon," Antimicrobial Agents and Chemotherapy, Apr. 2000, vol. 44, No. 4, pp. 859-866.

Martin, J., et al., Synthesis and Antiviral Activity of Monofluoro and Difluoro Analogues of Pyrimidine Deoxyribonucleosides Against Human Immnodeficiency Virus (HIV-1). J. Med. Chem. 1990, 33, 2137-2145.

Martin, X., et al., "Intramolecular hydrogen bonding in primary hydroxyl of thymine 1-(1-deoxy-β-D-piscofuranosyl)nucleoside," *Tetrahedron*, 50(22): 6689-6694 (1994).

Matsuda, et al., "Alkyl Addition Reaction of Pyrimidine 2'-Ketaonucleosides: Synthesis of 2'-Branched-Chain Sugar Pyrimidne Nucleosides (Nucleosides and Nucleotides. LXXXI)" Chem Pharm Bull, vol. 36(3):945-53 (1988).

Matsuda, et al., "Nucleosides and Nucleotides 94. Radical deoxygenation of tert-alcohols in 1-(2-C-alkylpentafuranosyl) pyrimidines: Synthesis of (2'S)-2-deoxy-2'-C-methylcytidine, and antileukemic nucleoside," Journal of Medicinal Chemistry, American Chemical Society Washington, US, vol. 34, 1991, pp. 234-239.

Matsuda, et al., "Nucleosides and Nucleotides 104. Radical and Palladium-Catalyzed Deoxygenation of the Allylic Alcohol Systems in the Sugar Moiety of Pyrimidine Nucleosides," *Nucleosides & Nucleotides*, Dekker, New York, NY, U.S., vol. 11, No. 2/4, 1992, pp. 197-226.

Matsuda, et al., "Radical deoxygenation of tert-alcohols in 2'—branched-chain sugar pyrimidine nucleosides: synthesis and antileukemic activity of 2'—deoxy-2' (S)-methylcytidine," Chem. Pharm. Bull., vol. 35, 1987, pp. 3967-3970.

Mikhailov, S.N., et al., "Hydrolysis of 2'-and 3'-C-methyluridine 2',3'-monophosphates and Interconversion and dephosphorylation of the resulting 2'-and 3'-monophosphates: Comparison with the reactions of Uridine monophosphates," *J. Org. Chem.*, vol. 57: 4122-26 (1992).

Mikhailov, S.N., et al., "Substrate properties of C'-methylnucleoside and C'-methyl-2'-deoxynucleoside 5'-triphosphates in RNA and DNA synthesis reactions catalysed by RNA and DNA polymerases," *Nucleosides & Nucleotides*, 10(1-3): 339-343 (1991).

Mikhailov, S. N., et al., "Synthesis and properties of 3'—C-methylnucleosides and their phosphoric esters," Carbohydrate Research, vol. 124, 1983, pp. 75-96.

Miles, et al., "Circular Dichroism of Nucleoside Derivatives. IX. Vicinal Effects on the Circular Dichrosim of Pyrimidine Nucleosides," J. Am. Chem. Soc. 92(13): 3872-3881 (1970).

Moore, et al., "Synthesis of Nucleotide Analogues That Potently and Selectively Inhibit Human DNA Primase." Biochemistry (2002), 41(47), 14066-14075.

Moiseyev, et al., "Determination of the nucleotide conformation in the productive enzyme-substrate complexes of RNA-depolymerases." FEBS Letters (1997), 404(2,3), 169-172.

Murai, et al., "A synthesis and an x-ray analysis of 2'-C-,3'-C- and 5'-C-methylsangivamycins," Heterocycles (1992), 33(1), 391-404.

Nishiguchi, S., et al., "Methods to Detect Substitutions in the Interferon-Sensitivity-Determining Region of Hepatitis C virus 1b for Prediction of Response to Interferon Therapy," Hepatology. Jan. 2001, vol. 33, No. 1, pp. 241-247.

Nishimura, T. et al. "Studies on Sythetic Nuclesides. Trimethylsilyl Derivatives of Pyrmidine and Purines," Chemical & Pharmaceutical Bulletin (1964), vol. 12, pp. 352-356.

Oivanen, M., et al., "Additional evidence for the exceptional mechanism of the acid-catalyzed hydrolysis of 4-oxopyrimidine nucleosides: Hydrolysis of 1-(1-alkoxyalkyl)uracils, seconucleosides, 3'-C-alkyl nucleosides and nucleoside 3', 5'-cyclic monophosphates," *J. Chem. Soc. Perkin Trans. 2*, 1994: 309-314 (1994).

Ong, S.P., et al., "Synthesis of 3'—C-methyladenosine and 3'—C-methyluridine diphosphates and their interaction with the ribonucleoside diphosphate reductase from *Corynebacterium nephridii*," Biochemistry, vol. 31, 1992, pp. 11210-11215.

Pagliaro, L., et al., "[Hepatology: Old, recent and (maybe) future stories. A narrative review]. EPATOLOGIA: IERI, OGGI E (FORSE) DOMANI," Recenti Progressi in Medicina, (2006), vol. 97, No. 12, pp. 741-750.

Pierra, C., et al., "NM 283, and efficient prodrug of the potent Anti-HCV agent 2'-C-methylcytidine," Nucleosides, Nucleotides and Nucleic Acids (2005), 24(5-7), 767-770.

Pierra, C., et al., "Synthesis and Pharmacokinetics of Valopicitabine (NM283), and Efficient Prodrug of the Potent Anti-HCV Agent 2'-C-Methylcytidine," Journal of Medicinal Chemistry (2006), 49(22), 6614-6620.

Reist, et al., "Potential anticancer agents. LXXVII. Synthesis of nucleosides of purine-6-thiol(6-mercaptopurine) containing "fraudulent" sugars." Journal of Organic Chemistry (1962), 27 3279-83.

Robins, et al., "Purine Nucleosides. XXIX. The Synthesis of 2'-Deoxy-L-adenosine and 2'-Deoxy-L-guanosine and Their [alpha]Anomers," Journal of Organic Chemistry, 35(3), 636-639 (Mar. 1970).

Rong, et al., "The Synthesis and Conformation of 2'-and 3'-Hypermodified Tricyclic Nucleosides and Their Use in the Synthesis of Novel 2'-or 3'-Isomeric 4(7)-Substituted Isoxazolidine-nucleosides," Tetrahedron vol. 50, No. 16, pp. 4921-4936, (1994).

Roque-Afonso, AM, et al., "Performance of TRUGENE hepatitis C virus5' noncoding genotyping kit, a new CLIP sequencing-based assay for hepatitis C virus genotype determination," Journal of Viral Hepatitis. Sep. 2002, vol. 9, Issue 5, pp. 385-389.

Rosenthal, et al., "Branched-chain sugar nucleosides. Synthesis of 3'—C-ethyl (and 3'—C-butyl) uridine," Carbohydrate Research, vol. 79, 1980, pp. 235-242.

Sakthivel, et al., "Direct SNAr amination of fluorinated imidazo[4,5-c]pyridine nucleosides: efficient syntheses of 3-fluoro-3deazaadenosine analogs." Tetrahedron Letters (2005), 46(22), 3883-3887.

Sakthivel, et al. "Electrophilic fluorination of 5-(cyanomethyl)imidazole-4-carboxylate nucleosides: Facile entry to 3-fluoro-3-deazaguanosine analogues." Synlett (2005), (10), 1586-1590.

Saladino, R., et al., "A new and efficient synthesis of cytidine and adenosine derivatives by dimethyldioxirane oxidation of thiopyrimidine and thiopurine nucleosides," J. chem. Soc., Perkin Trans. I., 21: 3053-3054 (1994).

Samano, et al., "Nucleic Acid Related Compounds. 77. 2',3'-Didehydro-2',3'-Dideoxy-2'(and 3')-Methylnucleosides Via [3,3]-Sigmatropic Rearrangements of 2'(and 3')-Methylene-3'(and 2')-O-Thiocarbonyl Derivatives and Radical Reuction of a 2'-Chloro-3'Methylene Analogue," Can. J. Chem., 71: 186-191 (1993).

Samano, et al., "Synthesis and Radical-Induced Ring-Opening Reactions of 2'-Deoxyadenosine-2'-Spirocyclopropane and its Uridine analogue. Mechanistic Probe for Ribonucleotide Reductases," J Am Chem Soc, 114: 4007-08 (1992).

Sandhu, et al., "Evaluation of microdosing strategies for studies in preclinical drug development: Demonstration of linear pharmacokinetics in dogs of a nucleoside analog over a 50-fold dose range." Drug Metabolism and Disposition (2004), 32(11), 1254-1259.

Sato, et al., "C-Nucleoside synthesis. 10. Synthesis of 2'-methylated pyrimidine C-nucleosides." Tetrahedron Letters (1980), 21(20), 1971-4.

Sato, et al., "C-Nucleoside synthesis. 19. Stereocontrolled general synthesis of pyrimidine C-nucleosides having branched-chain sugar moieties." Bulletin of the Chemical Society of Japan (1983), 56(9), 2680-99.

Savochkina, et al., "Substrate properties of c—methylnucleoside triphosphates in RNA syntheses catalyzed by *E. coli* RNA—polymeruse" Molecular Biology, 1989, v. 23, No. 6.

Schiff, E.R., "Emerging strategies for pegylated interferon combination therapy," Nature Clinical Practice Gastoenterology and Hepatology, (2007) vol. 4, No. Suppl. 1, pp. S17-S21.

Schmit, C., et al., "Synthesis of 2'-Deoxy-2'—Alpha-Monofluoromethyl and Trifluoromethylnucleosides," Synlett, Thieme Verlag, Stuttgart, DE, No. 4, 1994, pp. 241-242.

Schmit, C., et al., "The effects of 2'- and 3'-alkyl substituents on oligonucleotide hybridization and stability," *Bioorg. & Med. Chem. Lett.*, 4(16): 1969-1974 (1994).

Serafinowski, P.J., et al., "New method for the preparation of some 2'- and 3'-trifluoromethyl-2',3'-dideoxyuridine derivatives," *Tetrahedron*, 56(2):333-339 (1999).

Shalaby, et al., "Conformations and Structure Studies of Sugar Lactones in the Solid State. Part II. The Molecular Structure of a-D-Glucosaccharino-Y-Lactone: 2-C-Mehtyl-D-Ribo-Pentono-1,4-lactone." Carbohydrate Research (1994), 264(2), 191-8.

Sharma, et al., "Synthesis of 3'—Trifluoromethyl Nucleosides as Potential Antiviral Agents," Nucleosides, Nucleotides and Nucleic Acids, Marcel Dekker, Ann Harbor, MI, US, vol. 19, No. 4, 2000, pp. 757-774.

Shim, Jae H., "Recent patents on nucleoside and nucleotide inhibitors for HCV," Recetn Patents on Anti-Infective Drug Discovery (2006), 1(3), 323-331.

Sinkula, et al., *J. Pharm. Sci.*, 1975, 64: 181-210.

Smith, et al., "Synthesis of new 2'-β-C-methyl related triciribine analogues as anti-HCV agents." Valeant Pharmaceuticals International, Costa Mesa, CA, USA. Bioorganic & Medicinal Chemistry Letters (2004), 14(13), 3517-3520.

Song, et al., Amino Acid Ester Prodrugs of the Anticancer Agent Gemcitabine: Synthesis, Bioconversion, Metabolic Bioevasion, and hPEPT 1-Medicated Transport, Moleculare Pharmaceutics (2005), 2(2), 157-167.

Sorbera, L.A., et al., "Valopicitabine: anti-hepatitis C virus drug RNA —directed RNA polymerase (NS5B) inhibitor," Drugs of the Future (2006), 31 (4), 320-324.

Spardari, et al., "L-Thmidine is Phosphorylated by Herpes Simplex Virus Type 1 Thymidine Kinase and Inhibits Viral Growth," Journal of Medicinal Chemistry, 35(22), 4214-4220(1992).

Stuyver, et al., "Ribonucleoside Analogue That Block Replication of Bovine Viral Diarrhea and Hepatits C Viruses in Culture." Antimicrobial Agents and Chemotherapy, vol. 47, No. 1, Jan. 2003, pp. 244-254.

Takenuki, et al., "Nucleosides and nucleotides. XLIII. On the stereoselectivity of alkyl addition reaction of pyrimidine 2'-ketonucleosides." Chemical & Pharmaceutical Bulletin (1990), 38(11), 2947-52.

Tritsch, D., et al., "3'-β-ethynyl and 2'-deoxy-3 '-β-ethynyl adenosines: First 3'-β-branched adenosine substrates of adenosine deaminase," *Bioorg. & Med. Chem. Lett.*, 10: 139-141 (2000).

Tronchet, et al. "72. Synthese et desamination enzymatique des C-hydroxymethyl-3'-et C-methyl-3'—beta-D-xylofurannosyl-9-adenin es," Helv. Chim. Acta, vol. 62, 1979, pp. 689-695.

Tunitskaya, V.L., et al., "Substrate properties of C'-methyl UTP derivatives in T7 RNA polymerase reactions. Evidence for N-type NTP conformation," *FEBS Letters*, 400: 263-266 (1997).

Tyrsted, G., et al., "Inhibition of the synthesis of 5-phosphoribosyl-1-pyrophosphate by 3'-deoxyadenosine and structurally related nucleoside analogs," Biochem. Biophys. Acta., 155(2): 619-622 (Feb. 26, 1968).

Usui, H., et al., "Synthesis of 2'-deoxy-8,2'-ethanoadenosine and 3'-deoxy-8,3'-ethanoadenosine (Nucleotides & Nucleosides. LXIV)," Chem. Pharm. Bull., 34(1):15-23 (1986).

Vassilev, V., et al., "Bovine Viral Diarrhea Virus Induced Apoptosis Correlates with Increased Intracellular Viral RNA Accumulation." *Virus Research*, 69: 95-107 (2000).

Velazquez, et al., "Synthesis of '1-'3',5'-bis-0-(tert-butyldimethylsily)-beta-D-arabino-and beta-D-ribofuransoyl!cytosine!-2'—spiro-5"-(4"-amino-1",2'-oxathiole-2", 2"-dioxide). Analogues of the highly specific anti-HIV-1 agent TSAO-T," Tetrahedron, vol. 50, 1994, pp. 11013-11022.

Verri, A., et al., "Lack of enantiospecificity of human 2'-deoxycytidine kinase: relevance for the activetion of B-L-deoxyctidine analogs as antineolastic and antiviral agents," Molecular Pharmacology, 51(1): 132-138 (Jan. 1997).

Verri, a., et al., "Relaxed Enantioselectivity of Human Mitochondrial Thymidine Knase and Chemotherapeutic Uses of L-Nucleoside Analogues," Biochem. J., 328(1): 317-320 (Nov. 15, 1997).

Von Buren, et al., "Branched oligodeoxynucleotides: automated synthesis and triple helical hybridization studies." Tetrahedron (1995), 51(31), 8491-506.

Von Janta-Lipiniski, M., et al., "Newly Synthesized L-Enantiomers of 3'-Fluoro-Modified B-2'-Deoxyribonucleoside 5'-Triphosphates Inhibit Hepatitis B DNA Polymerase but not the Five Cellular SNA Polymerases a, B, y, d and E Nor HIV-1 Reverse Transcriptase," J. Medicinal Chemistry, 41(12): 2040-2046 (May 21, 1998).

Wagner, D., et al., "Preparation and Synthetic Utility of Some Organotin Derivatives of Nucleosides," J. Org. Chem., 39(1):24-30 (1974).

Walczak, K., et al., "Synthesis of 1-(3-alkyl-2,3-dideoxy-D-pentofuranosyl)uracils with potential anti-HIV activity," *Acta Chemica Scand.*, 45: 930-934 (1991).

Walton, et al., "Branched-Chain Sugar Nucleosides: V. Synthesis and Antiviral Properties of Several Branched-Chain Sugar Nucleosides," *Antiviral Nucleosides*, vol. 12: 306-309 (1969).

Wohnsland, A., et al., "Viral determinants of resistance to treatment in patients with hepatitis C," Clinical Microbiology reviews, (2007) vol. 20, No. 1, pp. 23-38.

Wolf, et al., "New 2'—C-Branched-Chain Sugar Nucleoside Analogs With Potential Antiviral or Antitumor Activity," Synthesis, Georg Thieme Verlag. Stuttgart, DE, No. 8, Aug. 1992, pp. 773-778.

Wolfe, et al., Tetrahedron Letters, vol. 36(42): 7611-14 (1995).

Wu, et al., "A New Stereospecific Synthesis of [3.1.0] Cicyclic Cyclopropano Analog of 2', 3'-Dideoxyuridine." *Tetrahedron*, vol. 46, 1990, pp. 2587-2592.

Zedeck, et al., *Mol. Phys.*, 1967, 3(4):386-95.

Zinichenko, et al., "Substrate Specificity of Uridine and Purine Nucleoside Phosphorylases of the Whole Cells of *Escherichia coli*." Nucleic Acids Research, Symposium Series No. 18., 1987, pp. 137-140.

Zinchenko, et al., "Substrate specificity of uridine and purine nucleoside phosporlases in whole cells of *E. coli*" Bioplymers & a cell, 1988, v. 4, No. 6.

U.S. Appl. No. 11/644,304, filed Dec. 22, 2006, Mayes et al.

Afdhal, et al., Enhanced antiviral efficacy for valopicitabine pluc PEG-interferon in hepatitis C patients with HCV genotype-1 infection. Journal of Hepatology 2005, vol. 42, Supplement 2, pp. 39-40.

Altmann, et al., The Effects of 2'-and 3'-Alkyl Substituents on Oligonucleotide Hybridization and Stability, Biorganic & Medicinal Chemistry Letter. 1994. 4. No. 16. 1969-74.

Clark, et al., Synthesis and antiviral activity . . . , Bioorganic & Medicinal Chemistry Letters, 16, 2006, 1712-1715.

Daniels et al., "Tautomerism of Uracil and Thymine in Aqueous Solution: Spectroscopic Evidence", Proc. Nat. Acad. Sci. USA, vol. 69, No. 9, pp. 2488-2491, 1972.

Eldrup, et al., "Structure-Activity Relationship of Hetcrobase-Modified 2'-C-Methyl Ribonucleosides as Inhibitors of Hepatitis C Virus RNA Replication." Department of Medicinal Chemistry, Isis Pharmaceuticals, Carlsbad, CA, USA. Journal of Medicinal Chemistry (2004), 47(21), 5284-5297.

Francesco, et al. Antiviral Research 58 (2003) 1-16.

Gerotto, et al., Effect of retreatment with interferon alone or interferon plus ribavirin on hepatitis C virus quasispecies diversification in nonresponder pateinets with chronic hepatitis C. Journal of Virology, Sep. 1999, vol. 73, No. 9, pp. 7241-7247.

Hattori, H. et al., "Nucleosides and Nucleotides 158" *Journal of Medicinal Chemistry, American Chemical Society*, vol. 39, 1996, pp. 5005- 5001.

Hu, et al., Viral, host and interferon-related factors modulating the effect of interferon therapy for hepaptitis C virus infection. Journal of Viral Hepatitis, 2001, vol. 8, pp. 1-18.

Shi, et al., Synthesis and in vitro Anti-HCV Activity of β-d- and 1-2'-Deoxy-2'-Fluororibonucleosides, Nucleosides, Nucleotides & Nucleic Acids 2005, vol. 23, No. 5-7, pp. 875-879.

Sinko, et al., Carrier-Mediated Intestinal Absorption of Valacyclovir, the L-Valyl Ester Prodrug of Acyclovir. Biopharmaceutics & Drug Disposition 1998, vol. 19, pp. 209-217.

Wu, et al., Targeting NS5B RNA-dependent RNA polymerase for anti-HCV chemotherapy. Current Drug Targets—Infectious Disorders 2003, vol. 3, p. 207-219.

Zhou, et al., Pharmacokinetics and pharmacodynamics of valopicitabine. Journal of Hepatology 2005, vol. 42 (Suppl. 2), p. 229.

Office Action dated Oct. 1, 2003 from U.S. Appl. No. 09/863,816.
Notice of Allowance dated Jun. 23, 2004 from U.S. Appl. No. 09/863,816.
Office Action dated Aug. 27, 2003 from U.S. Appl. No. 09/864,078.
Notice of Allowance dated Feb. 19, 2004 from U.S. Appl. No. 09/864,078.
Notice of Allowance dated May 17, 2005 from U.S. Appl. No. 10/602,135.
Office Action dated Apr. 5, 2005 from U.S. Appl. No. 10/602,135.
Notice of Allowance dated Mar. 9, 2006 from U.S. Appl. No. 10/602,136.
Office Action dated Jul. 28, 2006 from U.S. Appl. No. 10/602,142.
Office Action dated Sep. 20, 2007 from U.S. Appl. No. 10/602,142.
Office Action dated Dec. 10, 2008 from U.S. Appl. No. 10/602,142.
Office Action dated Nov. 15, 2005 from U.S. Appl. No. 10/602,142.
Office Action dated Mar. 29, 2007 from U.S. Appl. No. 10/602,142.
Office Action dated Feb. 26, 2008 from U.S. Appl. No. 10/602,142.
Office Action dated May 30, 2006 from U.S. Appl. No. 10/602,691.
Office Action dated Aug. 22, 2007 from U.S. Appl. No. 10/602,691.
Office Action dated Oct. 7, 2008 from U.S. Appl. No. 10/602,691.
Office Action dated Dec. 29, 2006 from U.S. Appl. No. 10/602,691.
Office Action dated Nov. 7, 2005 from U.S. Appl. No. 10/602,691.
Office Action dated Feb. 26, 2008 from U.S. Appl. No. 10/602,691.
Notice of Allowance dated Dec. 28, 2005 from U.S. Appl. No. 10/602,692.
Office Action dated Apr. 5, 2005 from U.S. Appl. No. 10/602,692.
Notice of Allowance dated Dec. 27, 2005 from U.S. Appl. No. 10/602,693.
Office Action dated Apr. 6, 2005 from U.S. Appl. No. 10/602,693.
Notice of Allowance dated Dec. 27, 2005 from U.S. Appl. No. 10/602,694.
Office Action dated Apr. 6, 2005 from U.S. Appl. No. 10/602,694.
Office Action dated Sep. 10, 2004 from U.S. Appl. No. 10/602,976.
Office Action dated May 19, 2005 from U.S. Appl. No. 10/602,976.
Notice of Allowance dated Oct. 13, 2005 from U.S. Appl. No. 10/602,976.
Office Action dated Aug. 15, 2006 from U.S. Appl. No. 10/608,907.
Office Action dated May 31, 2007 from U.S. Appl. No. 10/608,907.
Office Action dated Jan. 28, 2008 from U.S. Appl. No. 10/608,907.
Office Action dated Nov. 26, 2008 from U.S. Appl. No. 10/608,907.
Office Action dated Aug. 2, 2006 from U.S. Appl. No. 10/609,298.
Office Action dated Jul. 10, 2008 from U.S. Appl. No. 10/609,298.
Office Action dated Oct. 5, 2005 from U.S. Appl. No. 11/005,440.
Office Action dated Dec. 5, 2006 from U.S. Appl. No. 11/005,440.
Office Action dated Jun. 13, 2007 from U.S. Appl. No. 11/005,440.
Office Action dated Oct. 16, 2007 from U.S. Appl. No. 11/005,440.
Office Action dated Aug. 21, 2006 from U.S. Appl. No. 11/005,441.
Notice of Allowance dated Jun. 22, 2007 from U.S. Appl. No. 11/005,441.
Notice of Allowance dated Jan. 8, 2008 from U.S. Appl. No. 11/005,441.
Office Action dated Aug. 7, 2006 from U.S. Appl. No. 11/005,442.
Office Action dated May 16, 2007 from U.S. Appl. No. 11/005,442.
Office Action dated Nov. 28, 2007 from U.S. Appl. No. 11/005,442.

* cited by examiner

Taken from Harry-O'kuru et al., J. Org. Chem., 1997, 62(6):1754-59.

PROCESS FOR THE PRODUCTION OF 2-C-METHYL-D-RIBONOLACTONE

CROSS-REFERENCE

This application claims priority to U.S. Provisional Application No. 60/432,766, filed on Dec. 12, 2002, and U.S. Provisional Application No. 60/466,194, filed on Apr. 28, 2003.

FIELD OF THE INVENTION

This invention is a process for preparing sugar analogue compounds that have protected oxygen substituent groups, and in particular, 2,3,5-(independently optionally protected hydroxyl)-2-C-methyl-β-D-ribofuranose and 2,3,5-(independently optionally protected hydroxyl)-2-C-methyl-D-ribonic-γ-lactone. This invention further includes a process for preparing nucleosides, and in particular, 3',5'-(independently optionally protected hydroxyl)-2'-C-methyl-β-D-cytidine, optionally using the sugar prepared using the processes set forth herein, and specifically, the synthesis of prodrugs of pharmaceutical compounds. More particularly, it describes the synthesis of compounds that serve as prodrugs for the delivery of antiviral nucleosides and nucleoside analogue derivative compounds, and in particular, the 3'-O-valinyl ester of 2'-C-methyl-β-D-cytidine.

BACKGROUND OF THE INVENTION

A key intermediate in the preparation of sugar analogues used in the synthesis of nucleosides and vitamins is 2-C-methyl-D-ribono-lactone. As early as 1880, Scheibler described a process for preparing the lactone (John Sowden, "The Saccharinic Acids" in *Adv. Carbohydrate Chem.* 12:43-46 (1957), citing C. Scheibler, *Berichte* 13:2212 (1880)). Unfortunately, product yields were only approximately 10% (Id.). At about the same time, H. Kiliani synthesized 2-methyl-D-ribonolactone by treating D-fructose with calcium hydroxide (H. Kiliani, *Berichte*, 15:2953 (1882), as cited in F. J. Lopez-Herrera et al., *J. Carbohydrate Chemistry*, 13(5): 767-775 (1994)). However, the process required months to run to completion and product yield was only 10% (d. at 768). Kiliani's process, however, enabled him to establish the positions of important functional groups on the compound (John Sowden, "The Saccharinic Acids" in *Adv. Carbohydrate Chem.* 12:43-46 (1957), citing H. Kiliani, *Ann.*, 213:361 (1883)).

In the early 1960s, Whistler and BeMiller attempted to improve upon Kiliani's synthesis (Roy L. Whistler and J. N. BeMiller, "α-D-Glucosaccharino-1,4-lactone" in *Methods in Carbohydrate Chemistry*, 2:484-485 (1963)). Whistler and BeMiller added boiling water and calcium hydroxide to D-fructose, flushed the system with nitrogen gas, and repeated the same process. After 2 weeks; the mixture then was maintained for 6-8 weeks, after which it was treated with $CO_2$ and oxalic acid dihydrate, and filtered under pressure. The residue was washed repeatedly to a syrup-like consistency, and filtrates combined; solvent evaporated under reduced pressure and the resultant product allowed to crystallize under refrigeration (Id.). The final product yield was still only about 10% (Id. at 485).

In an attempt to improve product yields, Lopez-Aparicio et al. reported the synthesis of 2-C-methyl-D-ribono-1,4-lactone from 2,3-O-isopropylidene-D-glyceraldehyde as an alternative to the Kiliani synthesis (Lopez-Aparicio et al., *Carbohydrate Res.*, 129:99 (1984), as cited in F. J. Lopez-Herrera et al., *J. Carbohydrate Chemistry*, 13(5):767-775 (1994) at 768-769). The process of Lopez-Aparicio included condensing 2,3-O-isopropylidene-D-glyceraldehyde with (1-methoxy-carbonyl-ethylidene)triphenylphosphorane to produce methyl E-(S)-4,5-dihydroxy-4,5-O-isopropylidene-2-methyl-2-pentenoate; hydrolyzing (in HCl) and photochemically isomerizing the pentenoate; lactonizing the pentenoate product to produce a butenolide; tritylating the butenolide at C-5 by reaction with trityl-chloride and pyridine, followed by cis-hydroxylation with potassium permanganate and methylene chloride in the presence of a crown ether. Final removal of the trityl (triphenylmethyl) group was achieved by reaction with TFA (trifluoroacetic acid) (Id. at 768). Lopez-Aparicio et al. reported product yields of ribonolactone at about 80%, but others were not able to reproduce this figure based on the gram mass amounts of materials provided in the experimental section of their publication. Instead, calculations indicated a percent yield of about 36% ribonolactone. In addition, the process of Lopez-Aparicio et al. was far more complex than the Kiliani synthesis, required the use of toxic reagents such as potassium permanganate and specialized equipment for irradiation to attain photochemical isomerization, and had a minimum of 60 hours reaction time (Id. at 768, 770-772).

Walton et al. described the synthesis of 2'-C-methyladenosine from 2-C-methyl-D-ribono-lactone (Walton et al., *J. Am. Chem. Soc.*, 88(19):4524-5 (1966)). In this case, the lactone was converted into its 2,3,5-tri-O-benzoyl derivative, and then reduced with bis(3-methyl-2-butyl)borane to provide an anomeric mixture of 2,3,5-tri-O-benzoyl-2-C-methyl-D-ribofuranose (Id.). Attempts at separating the anomeric mixture both on acid-washed alumina and on silica gel resulted in rearrangement to 1,3,5-tetra-O-benzoyl-2-C-methyl-α-D-ribofuranose (Id.). In order to avoid rearrangement, the additional steps of treating the mixed anomers with benzoyl chloride in pyridine to obtain 1,2,3,5-tetra-O-benzoyl-2-C-methyl-(α)/(β)-D-ribofuranose, and of isolating the final product by chromatography were needed (Id.). Later Walton et al. described the synthesis of 2'-C-methyl-5-fluorocytidine, 2'-C-methyl-5-fluorouridine, and 2'- and 3'-C-methylcytidine via the Hilbert-Johnson reaction (Walton et al., *Antiviral Nucleosides* 12:306-309 (1969)). However, unexpectedly large amounts of O-glycoside formed when 2'-C-methylcytidine was synthesized from N-acetylcytosine-mercury, and mercury itself is a toxic reagent whose avoidance is desirable (Id.). In both synthetic procedures described by Walton et al., the final product yield was only about 11%.

In 1997 Harry-O'Kuru et al. described a synthetic route for preparing 2'-C-branched ribonucleosides (Harry-O'Kuru et al., *J. Org. Chem.*, 62:1754-9 (1997)). Commercially available 1,3,5-tri-O-benzoyl-α-D-ribofuranose was used as the starting material, which was prepared from D-ribose or D-arabinose (D-arabinopyranose). The 1,3,5-tri-O-benzoyl-α-D-ribofuranose was oxidized at the free 2-OH with Dess-Martin periodinane reagent, and produced 1,3,5-tri-O-benzoyl-2-keto-ribofuranose as well as its corresponding hydrate. The desired product and hydrate were stirred with excess $MgSO_4$ and permitted to stand overnight. The mixture was then filtered and concentrated in order to produce a substantially pure ketone product. The resultant 2-ketosugar was treated with $MeMgBr/TiCl_4$ (or alternatively with $MeTiCl_3$, $CH_2=CHMgBr/CeCl_3$, or $TMSC\equiv CLi/CeCl_3$), which produced an anomeric mixture of the desired 1,3,5-tri-O-benzoyl-2-substituted alkyl-, alkenyl- or alkynyl-ribofuranoside and its transesterified isomers, α- and β-2,3,5-tri-O-benzoyl-2-substituted alkyl, alkenyl or alkynyl ribofuranoside in a nearly 5:3 ratio of desired product to isomeric forms (Id. at 1755). The 2-alkylated ribofuranosides then were converted to a single, desired product, 1,2,3,5-tetrabenzoyl-2-alkylribofuranoside, by treatment with benzoyl chloride, DMAP and triethylamine in approximately a 70% yield with a β/α ratio of 4:1 (Id.).

Beigelman et al. described the syntheses of 2'-C-methyl-nucleosides from D-glucose and D-ribose (Beigelman et al., *Carbohydrate Research*, 166:219-232 (1987)). Using D-glucose as a starting material, 1,2:5,6-di-O-isopropylidene-3-C-methyl-α-D-allofuranose was prepared and converted by selective incorporation of a p-methylbenzoyl group via a 5,6-O-dibutylstannylidene derivative (Id.). This was followed by treatment with aqueous 90% trifluoroacetic acid and periodate oxidation, elimination of the formyl group on the compound, and acetylation (Id.). Final product yield was about 77% (Id.). With D-ribose as a starting material, a 2,3-dimethyl-isopropylidene derivative with a protected 5-position was subjected to aldol condensation with formaldehyde, then treated with excess toluene-p-sulfonyl chloride in pyridine (Id.). The compounds were subsequently used to form a variety of products using conditions known in the art, including, for example, Kuhn methylation, reduction with LiAlH$_4$ in THF, acid-catalyzed hydrolysis, and acetylation by boiling in excess Ac$_2$O in pyridine (Id.). Average product yield was approximately 75-80%, but required costly materials and reagents (Id.).

Novak and Sorm detailed the preparation of crystalline 2-C-methyl-D-ribose and derivative compounds from 2-C-methyl-D-ribonolactone via sodium borohydride reduction (J. J. K. Novak & F. Sorm, *Collection Czechoslov. Chem. Commun.*, 34: 857-866 (1969)). They characterized the nature of the hydroxyl group at the 2-position of the 2-C-methyl-ribofuranoside, particularly in comparison with the similarly situated hydroxyl group on the corresponding lactone (Id). While the hydroxy group on the lactone was easily acetylated under conditions known to those skilled in the art to afford 2,3,5-tri-O-acetyl and 2,3,5-tri-O-benzoyl-2-C-methyl-D-ribonolactone, analogous conditions produced only 3,5-di-O-acetyl- and 3,5-di-O-benzoyl-2-C-methyl-D-ribofuranosides from 2-C-methyl-ribofuranosides (Id).

Later, Novak described chiro-optical properties of 2-C-methyl-1,4-lactones, which were prepared from D-lyxose and D-xylose via hypoiodite oxidation, and which had p-toluoyl protecting groups at C3 and C5 on the lactone (J. J. K. Novak, *Collection Czechoslov. Chem. Commun.*, 39: 869-882 (1974)). In particular, a 2-CH$_3$-ribono-1,4-lactone was synthesized by hydrolysis from 3,5-p-toluoyl-2-Br, 2-CH$_3$-ribono-1,4-lactone (Id.). However, Novak described difficulty in separating protected lactone products from one another, and resulting syrup-like products when deblocking of the lactones by alkaline alcoholysis was attempted (Id. at 871).

Both Tokyo Tanabe Co., Ltd. (JP 61-212592) and BASF Aktiendgesellschaft (EP 0 288 847) reported epimerization processes for preparing unprotected D-ribose from D-arabinose, a common starting material for ribose production.

Tokyo Tanabe Co., Ltd., teaches the epimerization of aqueous D-arabinose in an organic solvent in the presence of a preferably molybdic (VI) acid and a boric acid compound, collection and passage of the reaction liquid through a 2- or 3-valent metal-type cation exchange material (a polystyrene-sulfonic acid-type strongly acidic ion exchange resin converted to a Ca-type was preferred), elution with water to separate the unprotected ribose, and collection of the ribose compound (JP 61-212592, Abstract).

BASF teaches a continuous process in which an aqueous/alcoholic solution of D-arabinose is heated in a solvent in the presence of a basic anion exchanger loaded with a molybdenum (VI) compound. The eluate is collected and dried, methanol or ethanol added to the dried eluate and the mixture cooled to about 0° C. to crystallize unconverted D-arabinose which then is separated and recycled. The remaining filtrate is concentrated and purified according to methods known to those skilled in the art over a strongly acidic ion exchanger in the Ca$^{2+}$ form, and any by product-free arabinose/ribose recycled into arabinose at the crystallization stage (EP 0288847).

Both the procedures of Tokyo Tanabe Co., Ltd. and BASF require sophisticated and expensive equipment and reagents, and the product compound has yet to have protecting groups added.

Japan Tobacco, Inc., prepared 3-DPA-lactone by protecting the 5-OH group on a gamma-ribonolactone, utilizing an acid chloride or acid anhydride with a tertiary amine to cause beta-elimination of the 3-OH and formation of a double bond between carbons 2 and 3 while simultaneously acylating the 2-OH group, and finally catalytically hydrogenating the double bond between C-2 and C-3 and removing the protective group to regenerate 5-OH. See EP 0 526,655 A1, EP 0 553,358 A1, and EP 0 553,358 B1, as well as their US equivalents U.S. Pat. No. 5,322,955 and U.S. Pat. No. 5,391,769.

Other related work on syntheses of ribonolactones and sugar analogues with protected substituents include the following.

Li et al., *Organic Letters*, 3(7):1025-28 (2001) synthesized 2'-C-β-trifluoromethyl pyrimidine ribonucleoside from 1,3,5-tri-O-benzoyl-α-D-ribofuranose, and then converted it to 3,5-di-O-benzoyl-2-C-β-trifluoromethyl-α-D-1-ribofuranosyl bromide. The latter bromide derivative compound was found to be an effective reaction intermediate in the formation of nucleosides.

Beigelman et al., *Bioorg. Khim.*, 12(10):1359-65 (1986), synthesized 2-C-methyl-D-ribose derivative compounds via benzylation of 1,2:5,6-di-O-isopropylidene-3-C-methyl-α-D-allofuranose to form a first intermediate; hydrolyzed and selectively acylated the first intermediate to form 3-O-benzyl-1,2-O-isopropylidene-3-C-methyl-6-O-toluoyl-α-D-allofuranose; and sequentially deisopropylidenated, oxidized (with periodic acid), deformylated, acetylated, debenzylated and acetylated again to provide 1,2,3-tri-O-acetyl-2-C-methyl-5-O-toluoyl-β-D-ribofuranose as a final product.

Feast et al., *Acta Chemica Scandinavica* 19:1127-34 (1965), reported the preparation of α-D-glucosaccharinic acid, shown to be 2-C-methyl-D-ribo-pentonic acid, by alkaline treatment of D-fructose or 1-O-substituted D-fructose via a 1,4-lactone intermediate.

Kohn et al., *J. Am. Chem. Soc.*, 87(23):5475-80 (1965), described a short route for obtaining a furanose derivative of an aldose, by reducing a tetraacyclohexono-gamma-lactone to its corresponding tetraacylhexofuranose through use of disiamylborane as a reducing agent. The reaction is particularly important for the formation of intermediates in the synthesis of C-1' furanosyl nucleosides.

Kempe et al., *Nucleic Acids Res.*, 10(21):6695-6714 (1982) reported the selective 2'-benzoylation at the cis 2',3'-diols of protected ribonucleosides and isomerization of 2'-benzoates to 3'-benzoates. These protected nucleosides were used to synthesize oligoribonucleotides on solid silica gel supports, and subsequent deprotection resulted in the advantage of minimal internal nucleotide cleavage.

U.S. Pat. No. 4,294,766 to Schmidt et al. detailed the synthesis of pure ribonolactone from a mixture of ribonolactone and arabonolactone. Ribonolactone is an intermediate in the formation of riboflavin (vitamin B$_2$). A mixture of potassium arabonate and potassium ribonate was "lactonized", and the resulting lactone mixture, of which about 70% was ribonolactone, was separated by fractional crystallization using dioxane or ethylene glycol monomethyl ether. Lactonization was performed by methods known in the art, such as, for example, by using ion exchangers, or by concentrating the lactone in the presence of $H_2SO_4$ or $K_2SO_4$ and filtering off the precipitate.

Nucleoside Coupling

Walton described the synthesis of branched-chain nucleosides prepared by reacting 2,3,5-tri-O-acyl-2-(or 3)-C-alkyl-ribofuranosyl halides with chloromercuric purine or pyrimidine compounds (U.S. Pat. No. 3,480,613). 3-Lower alkyl-D-ribofuranosyl halide intermediates were prepared starting from 1,2-O-isopropylidene-5-O-acyl-α-D-erythro-pentofuran-3-ulose by reacting this compound with a Grignard reagent to add a lower alkyl group at C3. Next, one of two pathways was followed: in the first pathway, the 5-O-acyl-1, 2-O-isopropylidene-3-lower alkyl-D-ribofuranose was subjected to acidic alcoholysis to form an alkyl 5-O-acyl-3-lower-alkyl D-ribofuranoside; the latter compound was then acylated to the alkyl 2,3,5-tri-O-acyl-3-lower alkyl-D-ribofuranoside; and the resulting ribofuranoside could then be converted to a free sugar by subjecting it to a basic solvolysis and further hydrolysis in strong acid in aqueous medium, or converted to a halogenose by a halogen replacement reaction in appropriate solvent. In the second pathway, the 5-O-acyl-1,2-O-isopropylidene-3-lower alkyl-D-ribofuranose was acylated under basic conditions (pyridine) in inert solvent to form 3,5-di-O-acyl-1,2-O-isopropylidene-3-lower alkyl-D-ribofuranose, which was then hydrolyzed in strong acid and further acylated to provide the desired intermediates. 2-substituted, 6-substituted or 2,6-disubstituted purine nucleosides having a branched-chain at the 2'-position or 3'-position on the sugar moiety were then prepared by reacting 2,3,5-tri-O-acyl-D-ribofuranosyl halide with a chloromercuric 2,6-disubstituted purine at temperatures of 100° C. to 140° C. in a solvent such as toluene or xylene. Nucleosides having a desired pyrimidinone base were derived from 2,3,5-tri-O-acyl-2 (or 3)-C-lower alkyl-D-ribofuranosyl halide by reaction with a 2,4-dialkoxy-pyrimidine to form 1-(2,3,5-tri-O-acyl-2 (or 3)-C-lower alkyl-D-ribofuranosyl)-4-alkoxy-2 (1H)-pyrimidone, which was then reacted with ammonia, or a primary or secondary amine to afford compounds having an amino substituent at the C-4 on pyrimidinone, or hydrolyzed under acidic or basic conditions to afford a pyrimidinone base having a hydroxy group at the C-4. Unfortunately, Walton's syntheses involve multiple steps, special conditions, and numerous, toxic reagents.

As shown in FIG. 5 the prior art teaches the coupling of 1,2,3,5-tetra-O-benzoyl-2-C-methyl-β-D-ribofuranose (4) with $N^4$-benzoylcytosine using BSA in acetonitrile. The reaction mixture was heated to reflux for approximately 30 minutes, after which the Lewis acid, $SnCl_4$, was added and the solution again heated to reflux for about 3.5 hours, to provide 4-NH-benzoyl-2', 3', 5'-tri-O-benzoyl-β-D-2'-C-methyl-cytidine (5a). Compound (5a) was obtained by dilution with ethyl acetate and aqueous, saturated sodium bicarbonate, and extensive chromatographic purification. Removal of the benzoyl protective groups was accomplished by overnight treatment of (5a) with a solution of methanol presaturated with ammonia to provide β-D-2'-C-methyl-cytidine (6).

Prodrugs

Pharmaceutically active compounds are sometimes administered in an esterified prodrug form. Carboxylic acid esters are used most commonly, while phosphonate and phosphate esters are used less frequently because they fail to hydrolyze in vivo and may produce toxic byproducts (see U.S. Pat. No. 6,312,662 to Erion et al.). Acyloxyalkyl esters are sometimes used as prodrugs for phosphate and phosphonate compounds, as are cyclic phosphonate esters and aryl esters, especially phenyl and benzyl esters (Farquhar et al., J. Pharm. Sci., (1983), 72(3):324; U.S. Pat. No. 6,312,662 to Erion et al.). Like nucleosides, phosphonic acids such as, for example, phosphonoformic acid and PMEA (Adefovir; 9-(2-phosphonylmethoxy-ethyl)adenine) show antiviral activity as do carboxylic acid or ether lipid prodrugs of nucleosides (U.S. Pat. No. 6,458,773 to Gosselin et al.).

Historically, prodrug syntheses and formulations have typically involved the 5'-position of a nucleoside or nucleoside analogue. Gosselin et al., supra, reported nucleosides in which the H of the 5'-OH group is replaced by any of the following: an acyl group including those in which the non-carbonyl moiety of the ester group is selected from straight, branched, or cyclic $C_1$-$C_{20}$ alkyl, phenyl or benzyl; a naturally-occurring or non-naturally-occurring amino acid; a 5'-ether lipid or a 5'-phosphoether lipid; alkoxyalkyl including methoxymethyl; aralkyl including benzyl; aryloxyalkyl such as, for example, phenoxymethyl; aryl including phenyl, optionally substituted with halogen, $C_1$-$C_4$ alkyl or $C_1$-$C_4$ alkoxy; a dicarboxylic acid such as, for example, succinic acid; a sulfonate ester such as, for example, an alkyl or aralkyl sulphonyl including methanesulfonyl; or a mono-, di-, or triphosphate ester.

Matulic-Adamic et al. (U.S. Pat. No. 6,248,878) reported the synthesis of nucleoside analogues that comprise a ribofuranose ring with a phosphorus-containing group attached to the 3'-position via an oxygen atom and a substituted pyrimidine base. The phosphorus-containing group includes dithioates or phosphoramidites, or may be part of an oligonucleotide. These compounds are prodrugs because they are reacted further to provide final, desired nucleosides and nucleoside analogues. The compounds are synthesized in a multi-step process that couples, as starting materials, a ribofuranose having an hydroxy or acetoxy group at C-1 and benzoyl-protecting groups at C-2-, C-3 and C-5, and a 4-OS-iMe$_3$ pyrimidine to produce an 1-(2,3,5-tri-O-benzoyl-ribofuranosyl)-pyrimidin-4-one; then adds ammonia in methanol to the product of the first reaction in order to remove the benzoyl protecting groups; then reacts DMT-Cl/Pyr reacted with the unprotected product compound, which results in the addition of DMT to the 5'-O position of ribofuranose; then reacts TBDMS-Cl, $AgNO_3$, and Pyr/THF with the 5'-O-DMT substituted ribofuranose; and finally performs standard phosphitylation to produce the phosphorus-containing group located at the 3'-O. Each of the syntheses presented include at least 4 to 7 steps.

Chu et al. described prodrugs that are azide derivative compounds and compositions, including nucleoside and phosphorylated nucleoside analogues (U.S. Pat. No. 6,271,212). Such azide prodrugs have as advantages their ability to cross the blood-brain barrier, provide a longer half-life, and afford greater bioavailability and increased stability of the active form of the drug than previously observed. However, Chu et al. reported a lengthy, multi-step synthesis required for preparing their azide prodrugs.

Borretzen et al. described antiviral prodrugs that were nucleosides and nucleoside analogues. They reported certain fatty acid esters of anti-viral nucleosides and nucleoside analogues where the fatty acid in a mono-unsaturated C18 or C20 fatty acid was bonded to the 5'-position of the nucleoside or nucleoside analogue through an acylation process (U.S. Pat. No. 6,153,594). The process was carried out in the presence of a catalyst, and was allowed to proceed for 24-60 hours.

Product isolation was accomplished by extraction with an organic solvent, and purification by chromatography and/or recrystallization from an appropriate solvent. Percent yield of the product varied widely from 15-82%. Borretzen et al., however, did not use the term "prodrug".

In 1999, McCormick et al. described the carbonate formation at the 3'-OH of guanosine, using an unprotected ribose as a starting material (McCormick et al., *J. Am. Chem. Soc.* 1999, 121(24):5661-5). McCormick was able to synthesize the compound by a sequential, stepwise introduction of the O- and N-glycosidic linkages, application of certain protecting groups, sulfonation and final deprotection. As one step in their process, McCormick et al. reacted unprotected guanosine with BOC-anhydride, DMAP, $Et_3N$, and DMSO at room temperature for 4 hours to obtain directly a carbonate at the 3'-OH of guanosine.

Also in 1999, Tang et al. disclosed a process for preparing phosphoramidite prodrugs of 2'-C-β-methyl-cytidine ribonucleosides (Tang et al., *J. Org. Chem.*, 1999, 64:747-754). Like many of their colleagues, Tang et al. reacted 1,2,3,5-tetra-O-benzoyl-2-C-methyl-β-D ribofuranose with persilylated 4-N-benzoylcytosine in the presence of the Lewis acid, $SnCl_4$, as a first step in their synthesis (Id. at 748, Scheme $1^a$).

In 2000, Novirio Pharmaceuticals (now Idenix) discovered that the stability and bioavailability of antiviral nucleoside analogues is enhanced by the administration of amino acid ester forms of antiviral nucleosides (U.S. Ser. No. 09/864,078, pending; U.S. Ser. No. 10/261,327, pending; WO 01/90121; and U.S. Provisional Application Nos. 60/377,983 and 60/392,351). Processes used for preparing these amino acid esters of nucleosides and nucleoside analogues began with appropriately branched β-D or β-L nucleosides that optionally could be protected by an appropriate protecting group such as, for example, a silyl group, and subsequently deprotected, by methods known to those skilled in the art (Zhang et al., *Tetrahedron Letters*, 1992, 33:1177-80; Greene et al., *Protective Groups in Organic Synthesis*, John Wiley & Sons, $2^{nd}$ Edition (1991); Kerr et al., *J. Pharmaceutical Sciences*, 1994, 83:582-6; Tang et al., *J. Org. Chem.*, 1999, 64(3): 747-754; and Cavelier et al., *Tetrahedron Letters*, 1996, 37:5131-4). The optionally protected branched nucleoside was then coupled with a suitable acyl donor, such as an acyl chloride and/or an acyl anhydride or an activated acid, in an appropriate protic or aprotic solvent and at a suitable reaction temperature, to provide the 2' or 3' prodrug of a 1', 2', 3' or 4' branched β-D or β-L nucleoside, optionally in the presence of a suitable coupling agent (see *Synthetic Communications*, 1978, 8(5): 327-33; *J. Am. Chem. Soc.*, 1999, 121 (24):5661-5; Bryant et al., *Antimicrob. Agents Chemother.*, 2001, 45, 229-235; Standring et al., *Antiviral Chem. & Chemother.*, 2001, 12 (*Suppl.* 1), 119-129; Benzaria et al., *Antiviral Res.*, 2001, 50, A79; Pierra et al., *Antiviral Res.*, 2001, 50, A79; and Cretton-Scott et al., *Antiviral Res.*, 2001, 50, A44). Possible coupling reagents are any reagents that enable compounds or moieties to be linked to one another including, but not limited to, various carbodiimides, CDI, BOP and carbonyldiimidazole. For example, for a 3'-prodrug of a 2'-branched nucleoside, the nucleoside preferably was not protected, but was coupled directly to an alkanoic or amino acid residue via a carbodiimide-coupling reagent.

The prior art process shown in FIG. 5 included the following reaction sequence for preparing a 3'-valinyl ester nucleoside prodrug of cytidine: 1,2,3,5-tetra-O-benzoyl-2-C-methyl-β-D-ribofuranose (4) was added to a mixture of BSA and $N^4$-benzoylcytosine in acetonitrile and heated to reflux for approximately 30 minutes, after which the Lewis acid, $5 nCl_4$, was added and the solution again heated to reflux for about 3.5 hours, to provide 4-NH-benzoyl-2', 3', 5'-tri-O-benzoyl-β-D-2'-C-methyl-cytidine (5a). Compound (5a) was obtained by dilution with ethyl acetate and aqueous, saturated sodium bicarbonate, and extensive chromatographic purification. Removal of the benzoyl protective groups was accomplished by overnight treatment of (5a) with a solution of methanol presaturated with ammonia to provide β-D-2'-C-methyl-cytidine (6). Compound (6) in DMF was reacted with N,N-dimethylformamide dimethyl acetal at room temperature for approximately 1.5 hours, to provide cytidine having a protected amino group at $C_4$, $N^4$-[(dimethylamino)methylene]-β-D-2'-C-methyl-cytidine (2); a solution of amino-protected cytidine (7) in dry pyridine next was reacted with imidazole and TBDPSCl at room temperature for approximately 6 hours to afford cytidine whose 5'-O was silyl-protected (8); N—Boc-L-Valine in the presence of DEC, DMAP, and THF/DMF then were added to the 4- and 5'-protected, β-D-2'-C-methyl-cytidine (8) at room temperature for approximately 2 days to produce a 4- and 5'-protected, 3'-O—L—N—BOC-valinyl ester of β-D-2'-C-methyl-cytidine (2); the 4- and 5'-protected, 3'-O—L—N—BOC-valinyl ester of β-D 2'-C-methyl-cytidine (2) was taken up in dry methanol to which was added ammonium fluoride and the mixture brought to reflux in order to remove the 5'-silyl and 4-amino protecting groups, producing 3'-O—L—N-(tert-butoxycarbonyl) valinyl ester of β-D-2'-C-methyl cytidine (10), which was purified by column chromatography; and finally, to a solution of 3'-O—L—N-(tert-butoxycarbonyl) valinyl ester of β-D-2'-C-methyl cytidine (10) in dry ethyl acetate was added a 20% solution of HCl/ethyl acetate and the mixture stirred for about 2 hours to remove the BOC-protecting group, thereby providing the hydrochloride salt of 3'-O-valinyl ester of β-D-2'-C-methyl-cytidine as a final product (11). The prior art synthesis shown in FIG. 6 used uracil in place of the benzoyl cytosine to prepare compound (11), β-D-2'-C-methyl-cytidine.

In view of the above, it would be advantageous to have an efficient process for preparing a nucleoside or a nucleoside analog, such as a 2'-methyl-nucleoside or a 2'-methyl-3'-O-valinyl-nucleoside, their intermediates, including the 2-C-methyl-ribonolactone and 2-C-methyl-D-ribofuranose, and their salts and/or prodrugs thereof.

It is another object of the present invention to provide a process for the selective addition of a group at the 3'-OH of a nucleoside that would render the derivative compound a prodrug.

It is yet another object of the present invention to have an efficient process for preparing protected sugar analogue compounds that involves a minimal number of steps, and utilizes an inexpensive starting material.

It is yet another object of the present invention to decrease significantly the time required for preparing protected sugar intermediates as compared to other processes for synthesizing similar products.

Further, it is another object of the invention to have a process that runs to completion in a matter of hours and provides a final product high in both yield and purity.

It is yet another object of the invention to have a process that employs easy-to-use, non-toxic reagents, and whose final product is easily isolated by techniques commonly known in the art and easily scaleable.

It is still another object of the present invention to obtain the final product compound in high yields and purity exceeding at least 90 or 95%.

It is a further object of the present invention to employ non-toxic, easily handleable reagents.

SUMMARY OF THE INVENTION

The present invention discloses a novel, improved process for preparing nucleosides and nucleoside analogs, such as β-D and β-L 2'-C-methyl-nucleosides and 2'-C-methyl-3'-O-ester nucleosides, and their salts and/or prodrugs thereof, by utilizing one or more of less amounts of reagents in less time with simpler purification steps and with greater product yields than found in the prior art. In addition, the process of the present invention is advantageously scalable to satisfy the requirements of industrial production.

Embodiments of the present invention specifically include processes that include the steps of (a) reacting a D-fructose with CaO to obtain a 2-C-methyl-D-ribonic-γ-lactone; and/or (b) reacting an optionally protected 2-C-methyl-D-ribonic-γ-lactone with a suitable reducing agent, such as Red-Al, optionally in a solvent, such as ethanol, to obtain an optionally protected 2-C-methyl-D-ribofuranose; and/or (c) coupling an optionally protected 2-C-methyl-D-ribofuranose with an unprotected base, such as cytosine, in the presence of an activating agent, such as a silylating agent (e.g. BSA), optionally in the presence of a Lewis acid, such as $SnCl_4$, to obtain an optionally protected 2'-C-methyl-nucleoside, for example a 2'-C-methyl-cytidine; and/or (d) providing a 3'-ester of a 2'-C-methyl-nucleoside, such as 2'-C-methyl-cytidine, using optimized reagents, reaction conditions (solvents, reaction times, etc.), and extraction/purification techniques. In a particular embodiment of the invention, the processes are exemplified in FIGS. 1 and 4.

Also provided are efficient, scalable synthetic methods for preparing a nucleoside prodrug in high yields that has a cleavable moiety at the 3'-position of the nucleoside. Further provided are cost-effective processes that employ non-toxic reagents for preparing a nucleoside, nucleoside analog, its salt or a prodrug thereof. A comparison of FIG. 4, a process of the present invention, with FIG. 5, a prior art process, demonstrates the increased economy of steps in the improved processes.

Also provided are efficient, scalable synthetic methods for preparing a 2-C-methyl sugar intermediate, such as independently 2,3,5-(independently optionally protected) and unprotected 2-C-methyl-D-ribonic-gamma-lactone (also referred to as 2-C-methyl-ribonolactone) and independently 1,2,3,5-(independently optionally protected) and unprotected 2-C-methyl-D-ribofuranose, by utilizing one or more of inexpensive reagents in less time with simpler purification steps and with greater product yields than found in the prior art.

A novel aspect of the present invention resides in the use of specific combinations of reagents that eliminate the need for separation, isolation and/or purification at steps intermediate in the synthesis. Selection of specific reagents that convert a predominant amount of starting material into product, that reduce racemization, and that are easily removable from the final product, provide a synthetic process that is more efficient than heretofore known. The overall result is a decrease in time for final prodrug product formation as well as an increased percent yield of the desired product. Moreover, the need for less time and fewer reagents result in greater overall cost effectiveness and provide an industrially scalable and safe process, if so desired.

In one embodiment, the process of the present invention is directed to the preparation of a nucleoside that is disubstituted at the 2'-C, such as a 2'-methyl-nucleoside or a 2'-methyl-3'-O-valinyl-nucleoside, its intermediates, such as 2,3,5-(independently optionally protected) and unprotected 2-C-methyl-D-ribonic-gamma-lactone (also referred to as 2-C-methyl-ribonolactone) and 1,2,3,5-(independently optionally protected) and unprotected 2-C-methyl-D-ribofuranose, and its salts and/or prodrugs thereof. In one preferred embodiment, the present invention is used to prepare 2,3,5-(independently optionally protected) or unprotected 2-C-methyl-D-ribonic-gamma-lactone. In another preferred embodiment, the present invention is used to prepare 1,2,3,5-(independently optionally protected) or unprotected 2-C-methyl-D-ribofuranose. In yet another preferred embodiment, the present invention is used to prepare β-D-2'-C-methyl-cytidine (4-amino-1-(3,4-dihydroxy-5-hydroxymethyl-3-C-methyl-tetrahydro-furan-2-yl)-1H-pyrimidine-2-one). In another preferred embodiment, the present invention is carried out to prepare the 3'-O-amino acid (including but not limited to a valyl ester) of β-D-2'-C-methyl-cytidine (2-amino-3-methyl-butyric acid 5-(4-amino-2-oxo-2H-pyrimidin-1-yl)-4-hydroxy-4-C-methyl-2-hydroxymethyl-tetrahydro-furan-3-yl ester) or its preferred hydrochloride salt form. Nucleosides, nucleoside analogs, salts or ester prodrugs prepared by the present invention may be used as intermediates in the preparation of a wide variety of other nucleoside analogues, or may be used directly as antiviral and/or antineoplastic agents.

In one embodiment, the improved process of the present invention includes reacting cytosine and an activator, such as BSA, optionally in the presence of a Lewis acid, for example as $SnCl_4$, with 1,2,3,5-(independently optionally protected) or unprotected 2-C-methyl-β-D-ribofuranose to form 4-amino-1-(3,4-(independently optionally protected-hydroxy)-5-O-protected-hydroxymethylene-3-methyl-tetrahydro-furan-2-yl)-1H-pyrimidin-2-one (see FIG. 4)

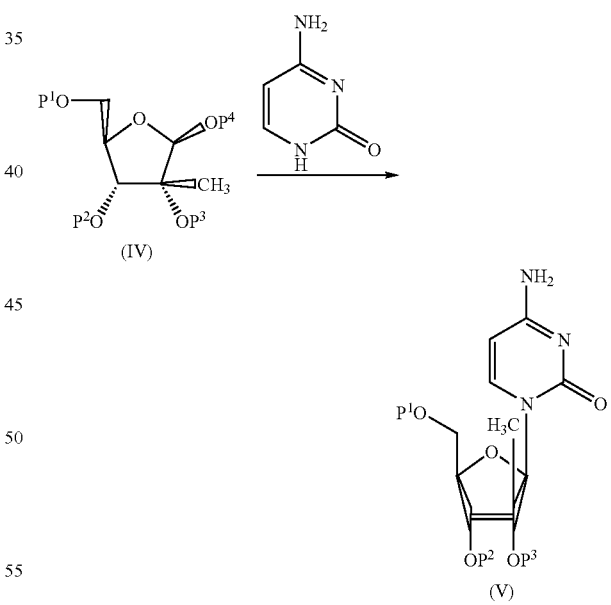

wherein each $P^1$, $P^2$, $P^3$, and $P^4$ is independently hydrogen or a suitable oxygen protecting group, such as an acyl, and preferably a benzoyl;

and then optionally deprotecting the 4-amino-1-(3,4-(independently optionally protected-hydroxy)-5-(optionally O-protected-hydroxymethylene)-3-methyl-tetrahydrofuran-2-yl)-1H-pyrimidin-2-one of the previous step to form 4-amino-1-(3,4- dihydroxy-5-hydroxymethyl-3-methyl-tetrahydro-furan-2-yl)-1H-pyrimidin-2-one (6) if necessary.

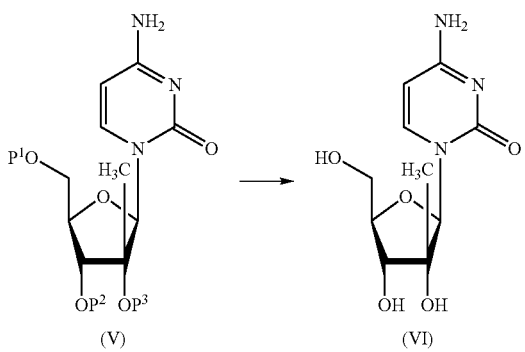

For example, if $P^1$, $P^2$ and $P^3$ of intermediate (V) is benzoyl, then the compound can be reacted with NaOMe/MeOH to provide 4-amino-1-(3,4-dihydroxy-5-hydroxymethyl-3-methyl-tetrahydro-furan-2-yl)-1H-pyrimidin-2-one (VI), also known as β-D-2'-C-methyl-cytidine, which optionally can be recrystallized, for example from ethanol, to obtain the β-D-2'-C-methyl-cytidine in pure form. This compound can if desired be utilized as is as an antiviral or can be further derivatized into a prodrug for delivery.

The intermediate (VI) then can be selectively optionally protected, esterified for example at the 3'-position, and optionally deprotected using any means known in the art to obtain the 3'-ester prodrug of β-D-2'-methyl-cytidine, such as 3'-O-valinyl ester of β-D-2'-C-methyl-cytidine (2-amino-3-methyl-butyric acid 5-(4-amino-2-oxo-2H-pyrimidin-1-yl)-4-hydroxy-4-C-methyl-2-hydroxymethyl-tetrahydro-furan-3-yl ester) or its preferred hydrochloride salt form.

As one nonlimiting example of the invention, if the 3'-valinyl ester is preferred, the esterification process may include the steps depicted in FIG. 4, namely: reacting β-D-2'-C-methyl-cytidine with Me$_2$NCH(OMe)$_2$ in DMF to form (7), N-[1-(3,4-dihydroxy-5-hydroxymethyl-3-methyl-tetrahydro-furan-2-yl)-2-oxo-1,2-dihydro-pyrimidin-4-yl]-N,N-dimethyl-formamidine, which is the amino-protected form of (VI); reacting (7) with TBDPSCl and imidazole in DCM to provide the 5'-silyl-protected form of (7) as N'-{1-[5-(tert-butyl-diphenyl-silanyloxymethyl)-3,4-dihydroxy-3-methyl-tetrahydro-furan-2-yl]-2-oxo-1,2-dihydro-pyrimidin-4-yl}-N,N-dimethyl-formamidine (8); reacting (8) with N—Boc-L-valine, EDC, and DMAP in DCM to form 2-tert-butoxycarbonylamino-3-methyl-butyric acid 2-(tert-butyl-diphenyl-silanyloxymethyl)-5-[4-(dimethylamino-methyleneamino)-2-oxo-2H-pyrimidin-1-yl]-4-hydroxy-4-methyl-tetrahydro-furan-3-yl ester (9); removing the silyl and amino-protecting groups by reacting (9) with NH$_4$F in MeOH with the addition of ethyl acetate (to prevent cleavage of the 3'-O-valinyl ester by liberated ammonia), and refluxing the mixture to provide 2-tert-butoxycarbonylamino-3-methyl-butyric acid 5-(4-amino-2-oxo-2H-pyrimidin-1-yl)-4-hydroxy-2-hydroxymethyl-4-methyl-tetrahydro-furan-3-yl ester (10), which is purified by simple crystallization; and finally, reacting (10) with HCl in EtOH to provide 2-amino-3-methyl-butyric acid 5-(4-amino-2-oxo-2H-pyrimidin-1-yl)-4-hydroxy-2-hydroxymethyl-4-methyl-tetrahydrofuran-3-yl ester, dihydrochloride salt (11) as a final product.

The use of cytosine rather than benzoyl cytosine or other protected cytosine as found in the prior art improves the atom economy and simplifies purification procedures.

The process of the present invention is advantageous in that it utilizes up to approximately 50% less reagents than a similar process found in the prior art. Even with the use of fewer reagents, a comparison with the closest prior art process reveals an increase in overall product yield, in one example, from 12% to 38%. A further advantage is found in the decreased cycle time required for completion of the prodrug synthesis. Compared to the prior art synthesis shown, the improved process of the present invention cuts cycle time by about 80%. This is due primarily to four factors: i) an increase in loading with a consequent decrease in the number of batches required; ii) an increase in percent yield; iii) the use of easily handleable solvents and reagents; and iv) elimination of labor-intensive chromatographic purification steps.

A novel aspect of the present invention resides in the use of specific combinations of reagents that eliminate the need for separation, isolation and/or purification at steps intermediate in the synthesis. Selection of specific reagents that convert a predominant amount of starting material into product, that reduce racemization, and that are easily removable from the final product, provide a synthetic process that is more efficient than heretofore known. The overall result is a decrease in time for final prodrug product formation as well as an increased percent yield of the desired product. Moreover, the need for less time and fewer reagents result in greater overall cost effectiveness and provide an industrially scalable and safe process, if so desired.

In an additional embodiment of the present invention, the 1,2,3,5-(independently optionally protected)-2-C-methyl-β-D-ribofuranose is obtained from the 2,3,5-(independently optionally protected)-2-C-methyl-D-ribonic lactone via reduction with a reducing agent, such as with sodium bis(2-methoxyethoxy)aluminum hydride (Red-Al), optionally in a solvent, such as ethanol;

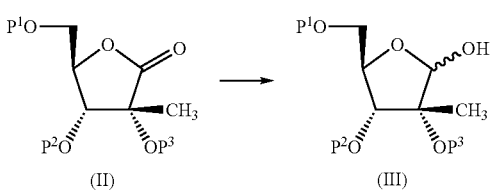

wherein each $P^1$, $P^2$, and $P^3$ is independently hydrogen or a suitable oxygen protecting group, such as an acyl, and preferably a benzoyl;

and then optionally protecting (e.g. benzoylating) the ribofuranose derivative compound of the previous step to form 1,2,3,5-(independently optionally protected)-2-C-methyl-β-D-ribofuranose if necessary,

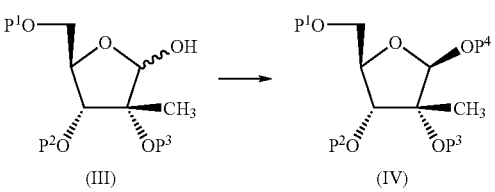

wherein $P^4$ is independently hydrogen or a suitable oxygen protecting group, such as an acyl, and preferably a benzoyl.

The use of Red-Al as a reducing agent of the present invention unexpectedly affords products having specific stereochemistry that allows for their efficient separation. This simplifies isolation of the desired, final product.

In a further embodiment of the present invention, the 2,3,5-(independently optionally protected)-2-C-methyl-D-ribonic lactone is obtained by reacting D-fructose with CaO;

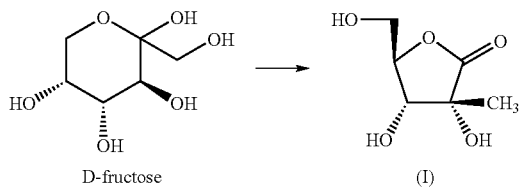

D-fructose                 (I)

and then, optionally protecting the lactone, for example with benzoyl chloride (or another suitable acyl chloride), to form 2,3,5-(independently optionally protected)-2-C-methyl-D-ribonic lactone, if necessary;

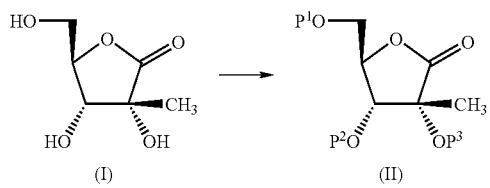

(I)                        (II)

wherein each $P^1$, $P^2$, and $P^3$ is independently hydrogen or a suitable oxygen protecting group, such as an acyl, and preferably a benzoyl.

In addition, to isolate a pure, single anomer product (i.e., in substantially pure form, which refers to at least 95%), purification step(s) may be added as needed.

The process of the present invention utilizes inexpensive D-fructose as a starting material, thereby providing significant cost savings for the producer. This is especially important where scale-up for industrial applications is required or envisioned.

In addition to the significant economic advantage of using D-fructose as a starting material, the present invention enjoys the novel aspect of using calcium oxide (CaO) as a reagent in the first step of the process. CaO is added to D-fructose in water to prepare 2-C-methyl-D-ribonic-gamma-lactone. This step alone runs to completion faster and accounts for increases in yield of 30-40% over similar processes in the prior art. Moreover, CaO is non-toxic, easy to use and mixes well with fructose and water.

A precipitant is used to remove calcium from the solution. In one embodiment, $CO_2$ and an acid that is stronger than ribonic acid, and in a preferred embodiment, an organic acid, is added to the reaction mixture to form calcium carbonate. Suitable organic acids include, but are not limited to: oxalic acid, malonic acid, succinic acid, glutaric acid, adipic acid, suberic acid, sebacic acid, azelaic acid, maleic acid, acetic acid, propionic acid, isobutyric acid, acrylic acid, methacrylic acid, butyric acid, pentanoic acid, hexanoic acid or hexanoic acid.

Moreover, the overall process provided by combining FIGS. 1 and 4 is advantageous in that it utilizes up to 50% less reagents than a similar process found in the prior art. Even with the use of fewer reagents, a comparison with the closest prior art process reveals an increase in overall product yield from, for example, 12% to 38%. A further advantage is found in the decreased cycle time required for completion of the prodrug synthesis. Compared to the prior art synthesis shown, the improved process of the present invention cuts cycle time by about 80%. This is due primarily to four factors: i) an increase in loading with a consequent decrease in the number of batches required; ii) an increase in percent yield; iii) the use of easily handleable solvents and reagents; and iv) elimination of labor-intensive chromatographic purification steps.

Therefore, in one embodiment of the invention, a process for the preparation of 2'-C-methyl-D-cytidine from D-fructose is provided, comprising the steps of:

(a) reacting D-fructose with CaO to obtain a 2-C-methyl-D-ribonic-γ-lactone;

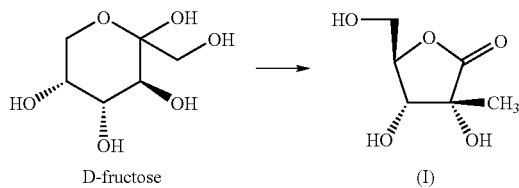

D-fructose                 (I)

(b) optionally protecting the lactone, for example with benzoyl chloride (or another suitable acyl chloride), to form 2,3,5-(independently optionally protected)-2-C-methyl-D-ribonic lactone, if necessary;

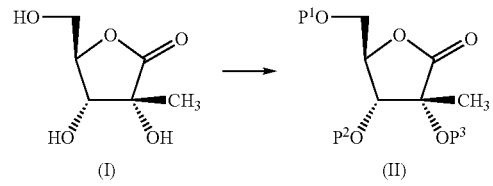

(I)                        (II)

wherein each $P^1$, $P^2$, and $P^3$ is independently hydrogen or a suitable oxygen protecting group, such as an acyl, and preferably a benzoyl;

(c) reacting the 2,3,5-(independently optionally protected)-2-C-methyl-D-ribonic lactone with a reducing agent, such as with sodium bis-(2-methoxyethoxy)aluminum hydride (Red-Al), optionally in a solvent, such as ethanol;

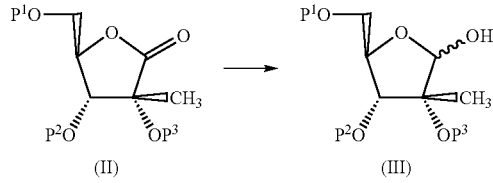

(II)                       (III)

wherein each $P^1$, $P^2$, and $P^3$ is independently hydrogen or a suitable oxygen protecting group, such as an acyl, and preferably a benzoyl;

(d) optionally protecting (e.g. benzoylating) the ribofuranose derivative compound of the previous step to form 1,2,3,5-(independently optionally protected)-2-C-methyl-β-D-ribofuranose if necessary,

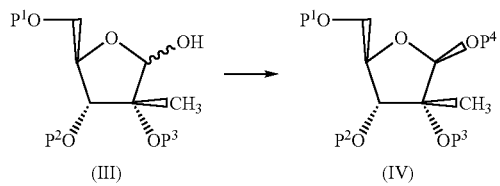

(III) → (IV)

wherein P⁴ is independently hydrogen or a suitable oxygen protecting group, such as an acyl, and preferably a benzoyl, (e) reacting the 1,2,3,5-(independently optionally protected)-2-C-methyl-β-D-ribofuranose with cytosine and an activator, such as BSA, optionally in the presence of a Lewis acid, such as $SnCl_4$, to form 4-amino-1-(3,4-(independently optionally-protected-hydroxy)-5-O-protected-hydroxymethylene-3-methyl-tetrahydrofuran-2-yl)-1H-pyrimidin-2-one

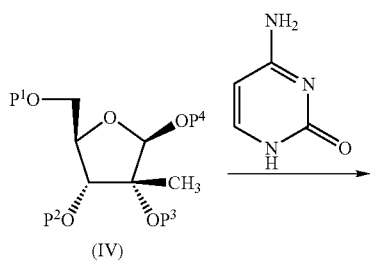

(IV) →

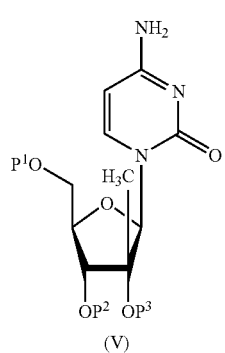

(V)

wherein each $P^1$, $P^2$, $P^3$, and $P^4$ is independently hydrogen or a suitable oxygen protecting group, such as an acyl, and preferably a benzoyl; and then (f) optionally deprotecting the 4-amino-1-(3,4-(independently optionally protected-hydroxy)-5-O-protected-hydroxymethylene-3-methyl-tetrahydro-furan-2-yl)-1H-pyrimidin-2-one of the previous step to form 4-amino-1-(3,4-dihydroxy-5-hydroxymethyl-3-methyl-tetrahydro-furan-2-yl)-1H-pyrimidin-2-one (VI) if necessary,

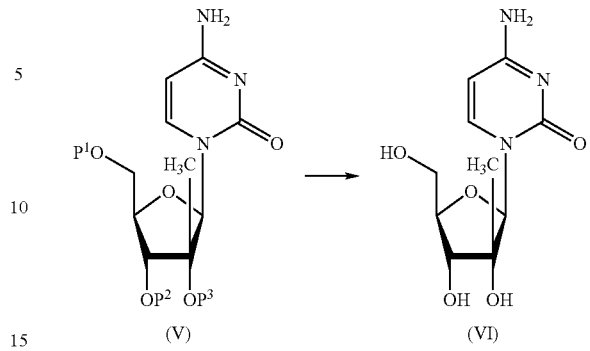

(V) → (VI)

(g) optionally protecting/deprotecting and then esterifying the 3'-positions of the 4-amino-1-(3,4-dihydroxy-5-hydroxymethyl-3-methyl-tetrahydro-furan-2-yl)-1H-pyrimidin-2-one (VI), for example with L-valine, to obtain the 3'-ester prodrug of β-D-2'-methyl-cytidine, for example the 3'-O-valinyl ester of β-D-2'-C-methyl-cytidine (2-amino-3-methyl-butyric acid 5-(4-amino-2-oxo-2H-pyrimidin-1-yl)-4-hydroxy-4-C-methyl-2-hydroxymethyl-tetrahydro-furan-3-yl ester), optionally in salt form, if desired.

DETAILED DESCRIPTION OF THE INVENTION

Figure 1:
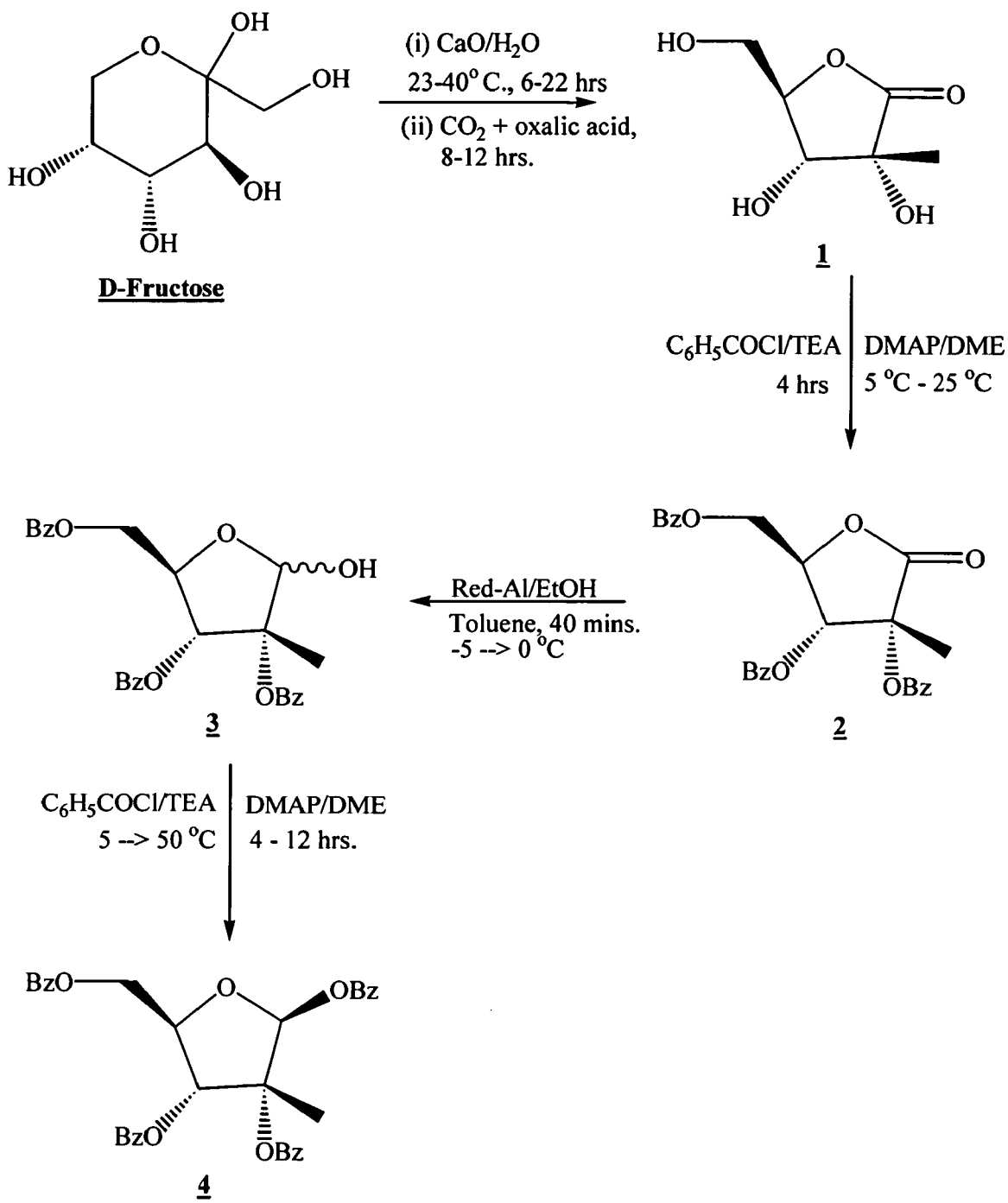
FIG. 1 is a schematic of a preferred process for preparing 1,2,3,5-tetra-O-benzoyl-2-C-methyl-β-D-ribofuranose and 2,3,5-tri-O-protected-2-C-methyl-D-ribonic-γ-lactone.

Processes are provided for preparing nucleosides and nucleoside analogs, such as 2'-C-methyl-nucleosides and 2'-C-methyl-3'-O-valinyl nucleosides, and their salts and/or prodrugs thereof, in all its stereochemical and tautomeric forms, by utilizing fewer reagents in less time and with greater product yields than found in the prior art. Furthermore, it eliminates the need for time-consuming and labor-intensive chromatographic purification steps, and keeps undesired racemization at acceptable levels. The improved process includes the formation of the nucleoside of interest as an intermediate in the prodrug synthesis, and advantageously may be scaled to meet the requirements of industrial production.

Also provided are efficient, scalable synthetic methods for preparing a 2-C-methyl sugar intermediate, such as 2,3,5-(independently optionally protected) and unprotected 2-C-methyl-D-ribonic-gamma-lactone (also referred to as 2-C-methyl-ribonolactone) and 1,2,3,5-(independently optionally protected) and unprotected 2-C-methyl-D-ribofuranose, by utilizing inexpensive reagents, such as D-fructose, in less time with simpler purification steps and with greater product yields than found in the prior art.

In one embodiment, the process of the present invention is directed to the preparation of a nucleoside that is disubstituted at the 2'-C position, such as a 2'-methyl-nucleoside or a 2'-methyl-3'-O-valinyl-nucleoside, its intermediates, such as 2,3,5-(independently optionally protected) and unprotected 2-C-methyl-D-ribonic-gamma-lactone (also referred to as 2-C-methyl-ribonolactone) and 1,2,3,5-(independently optionally protected) and unprotected 2-C-methyl-D-ribofuranose, and its salts and/or prodrugs thereof. In one preferred embodiment, the invention is used to prepare 2,3,5-(independently optionally protected) or unprotected 2-C-methyl-D-ribonic-gamma-lactone. In another preferred embodiment, the invention is used to prepare 1,2,3,5-(independently optionally protected) or unprotected 2-C-methyl-D-ribofuranose. In yet another preferred embodiment, the present invention is used to prepare β-D-2'-C-methyl-cytidine (4-amino-1-(3,4-dihydroxy-5-hydroxymethyl-3-C-methyl-tetrahydro-furan-2-yl)-1H-pyrimidine-2-one). In another embodiment, the present invention is carried out to prepare 3'-O-valinyl ester of β-D-2'-C-methyl-cytidine (2-amino-3-methyl-butyric acid 5-(4-amino-2-oxo-2H-pyrimidin-1-yl)-4-hydroxy-4-C-methyl-2-hydroxymethyl-tetrahydro-furan-3-yl ester) or its preferred hydrochloride salt form. Nucleosides, nucleoside analogs, salts or ester prodrugs prepared by the present invention may be used as intermediates in the preparation of a wide variety of other nucleoside analogues, or may be used directly as antiviral and/or antineoplastic agents.

In a first embodiment, the process of the present invention utilizes D-fructose as a starting material in a short synthesis to prepare 1,2,3,5-(independently optionally protected)-2-C-methyl-β-D-ribofuranose.

In a second embodiment, the process of the present invention is directed to the preparation of a nucleoside, nucleoside analog, or a salt or prodrug thereof, that is disubstituted at the 2'-C position.

In a third embodiment, the present invention is used to prepare β-D-2'-C-methyl-cytidine (4-amino-1-(3,4-dihydroxy-5-hydroxymethyl-3-C-methyl-tetrahydrofuran-2-yl)-1H-pyrimidin-2-one).

In a fourth embodiment, the present invention is carried out to prepare 3'-O-valinyl ester of β-D-2'-C-methyl-cytidine (2-amino-3-methyl-butyric acid 5-(4-amino-2-oxo-2H-pyrimidin-1-yl)-4-hydroxy-4-C-methyl-2-hydroxymethyl-tetrahydrofuran-3-yl ester) or its preferred hydrochloride salt form.

Nucleosides, nucleoside analogues, salts or ester prodrugs prepared by the present invention may be used as intermediates in the preparation of a wide variety of other nucleoside analogues, or may be used directly as antiviral and/or antineoplastic agents.

The process of the present invention is advantageous in that it utilizes less than 50% of the quantities of reagents than a similar process found in the closest prior art. Even so, a comparison with the prior art reveals an increase in overall product yield from 12% to 38%. A further advantage of the present invention is an approximate 80% decrease in the cycle time of the prodrug synthesis. Yet another advantage lies in the safety and easy scalability of this novel process to meet the requirements of production at industrial levels.

One novel aspect of the present invention resides in the use of specific combinations of reagents that eliminate the need for separation, isolation and/or purification of intermediates in the synthesis. Selection of certain reagents that convert a predominant amount of starting material into the final product, that reduce racemization of the amino acid prodrug moiety, and that are easily separated and removed from the final product, provide greater process efficiency than heretofore known. The overall result is a decrease in preparation time for the final product and an increase in its percent yield. Moreover, because less time and fewer reagents are needed, there is an overall benefit in terms of cost savings.

Figure 4:
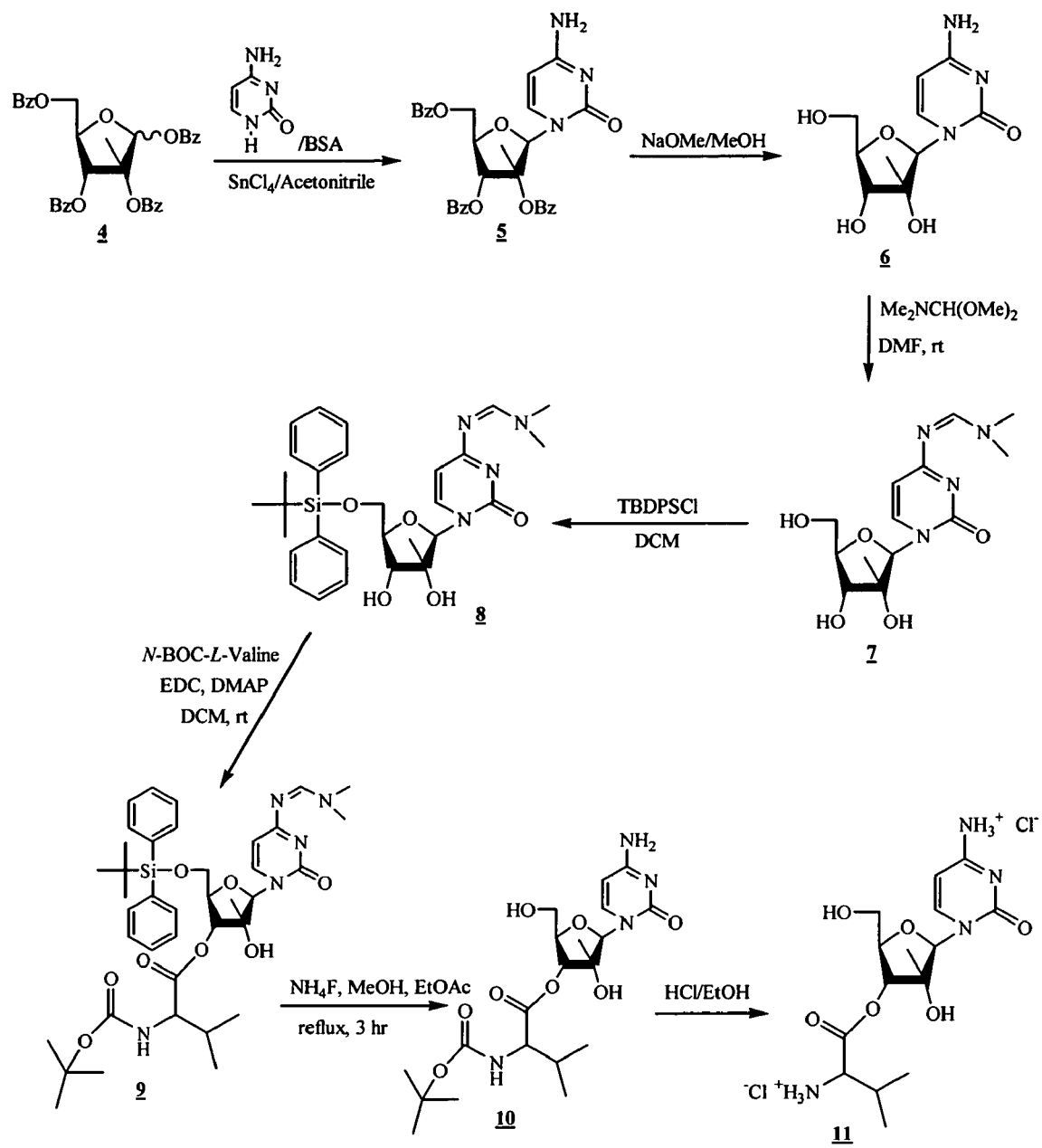
FIG. 4 is a schematic of a preferred process of the present invention for preparing a nucleoside, nucleoside analog, or a salt or prodrug thereof.

Advantages found in the improved process of the present invention include, in FIG. 1, the use of D-fructose as an inexpensive starting material and CaO, which decreased the reaction time and increased the percent yield of lactone production; reduction with Red-Al/ethanol that provided a regioselective mix of anomeric product compounds from which the final 1,2,3,5-tetra-O-benzoyl-2-C-methyl-β-D-ribofuranose can easily be separated by methods known to one of skill in the art; in FIG. 4, the use of cytosine as a starting material rather than benzoyl-cytosine (FIG. 5) or uracil (FIG. 6) as found in the prior art which improves the "atom economy" of the process by employing a less complex and less expensive compound of lower molecular weight; the requirement of fewer equivalents of cytosine, $SnCl_4$ and BSA in the present invention compared to similar steps in the prior art processes; the combination of reactants and reagents in lesser equivalent amounts than used heretofore that produces the dual benefits of a reaction that runs to completion within 3 to 4 hours and the production of intermediate (2) in FIG. 4 of such purity that additional chromatographic isolation and purification steps are rendered unnecessary.

FIG. 1 is a schematic of one embodiment of the present invention. In this improved process, the time required to form the ribonolactone (compound 1) from D-fructose is approximately 40 hours or less than 2 days, and results in about a 13.6% product yield, which is 30-40% greater than found in the closest prior art. By comparison, the ribonolactone syntheses of Kiliani and Scheibler each took 2 or more months to complete and resulted in an approximate 10% product yield (Lopez-Herrera et al., *J. Carbohydrate Chemistry* 1994, 13(5):767-775 at 768).

It was discovered unexpectedly that calcium oxide (CaO) and water can be reacted with the inexpensive starting material, D-fructose, to prepare 1,2,3,5-tetra-O-protected-2-C-methyl-β-D-ribofuranose in yields 30-40% greater than previously obtained. This process allows for the preparation of large quantities of 2-C-methyl-β-D-ribofuranose having protected hydroxy groups, an important intermediate in the synthesis of biologically active nucleosides and certain vitamin compounds. An advantage ancillary to this discovery is meaningful cost-savings in making the product, an especially important consideration where large-scale, industrial synthesis is anticipated. For example, 1,2,3,5-tetra-O-benzoyl-2-C-methyl-β-D-ribofuranose is commonly prepared from D-ribose by using D-arabinose as a starting material. The synthesis from D-arabinose requires at least 5 steps and chromatographic purification. In addition, the cost per kilogram of D-arabinose is approximately 250 times that of D-fructose! By using the improved process of the present invention, only 4 steps and inexpensive reagents are needed to prepare 2-C-methyl-ribose with protecting groups at positions 1, 2, 3, and 5. Thus, the desired product is made efficiently and cost effectively without the need for chromatographic purifications.

Also surprising was the finding that CaO, when used as the initial reagent in the process, significantly decreased the time required for formation of the 2-C-methyl-β-D-ribonolactone. This significantly lessened the overall time required for synthesis as compared to the earlier work of Kiliani and Scheibler in which $Ca(OH)_2$ was used as a reagent.

It also was discovered that Red-Al, optionally in ethanol, as a reducing agent, produced 2,3,5-tri-O-benzoyl-1-hydroxy-2-C-methyl-β-D-ribofuranose that, when acylated, gave substantially a single anomer product, resulting a more efficient separation. This simplifies isolation of the desired, final product.

Aspects of the advantages of the present invention include the following: the selection of D-fructose as an inexpensive starting material is economically favorable for preparing the final, protected sugar analogue; the use of CaO results in increased product yield and decreased reaction time for lactone production; and reduction with Red-Al provides a regioselective mix of anomeric product compounds from which the final product is easily isolated by ordinary methods and equipment. Other advantages include the use of inexpensive reagents in addition to the economical starting reagent, a minimal number of steps for handling intermediary compounds in the overall process, and the requirement for only ordinary methods and equipment well known to those skilled in the art rather than complicated steps and expensive apparatus.

FIG. 4 is a schematic of another embodiment of the present invention. Advantages found in this improved process include the following. The use of cytosine as a starting material rather than benzoyl-cytosine (FIG. 5) or uracil (FIG. 6) as found in the prior art improves the "atom economy" of the process by employing a less complex and less expensive compound of lower molecular weight. In addition, the present invention requires the use of fewer equivalents of cytosine, $SnCl_4$ and BSA compared to similar steps in the prior art processes. This combination of reactants and reagents in lesser equivalent amounts than used heretofore produces the dual benefits of a reaction that runs to completion within 3 to 4 hours, and the production of intermediate (2) of such purity that additional chromatographic isolation and purification steps are rendered unnecessary.

Figure 5:
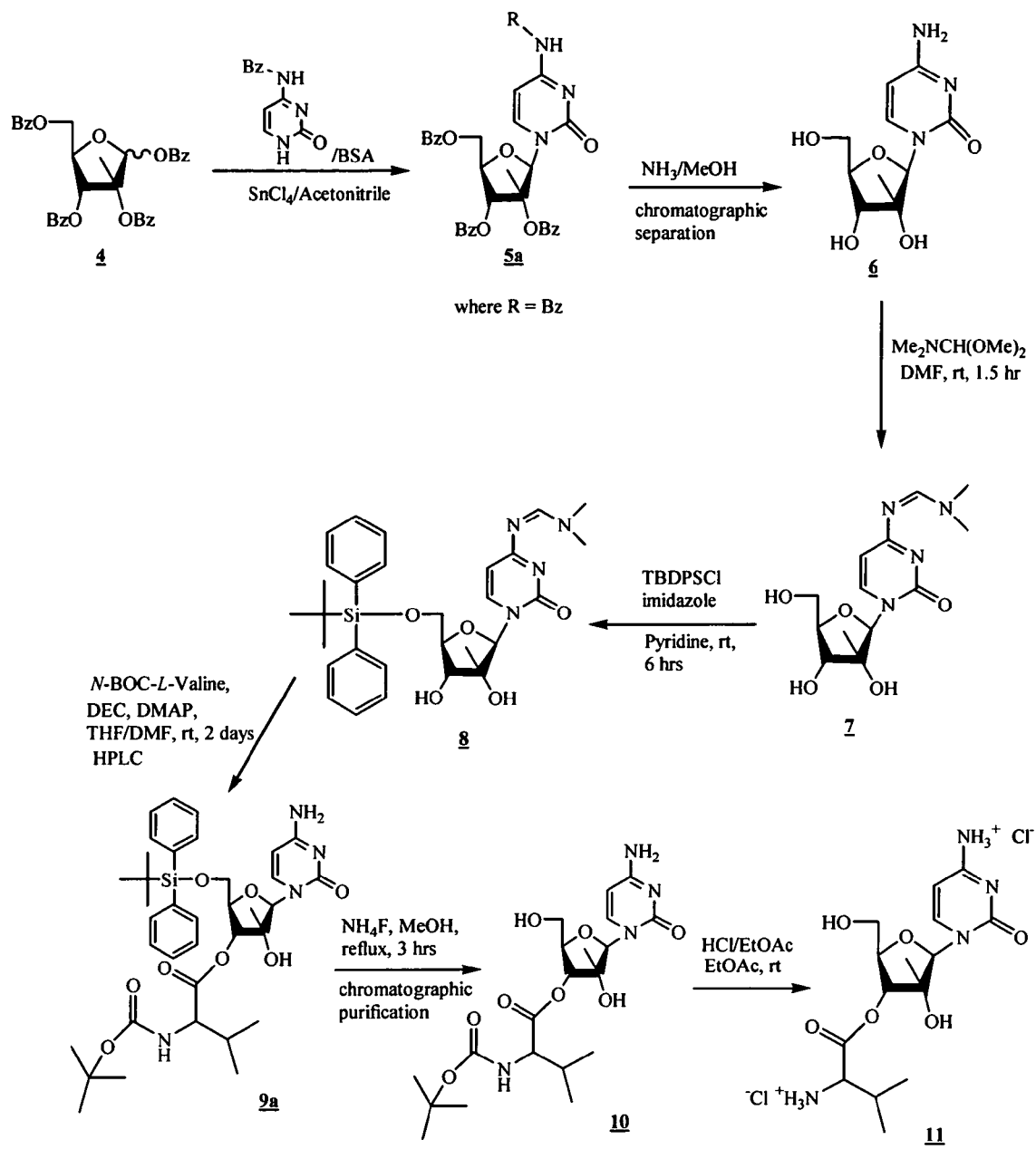
FIG. 5 is a schematic of a alternative process for preparing a pharmaceutically acceptable salt of the 3'-O-valinyl ester of β-D-2'-C-methyl-cytidine.

It was surprisingly found that the use of NaOMe in MeOH in the deprotection step of the present invention (FIG. 4, (5)→(6), removal of benzoyl-protecting groups) offers the advantages of being less expensive, safer, and easier to use in an industrially scalable synthesis compared to the use of ammonia in the prior art process (FIG. 5, (5a)→(6)). An added benefit results from a faster reaction time: the reaction using sodium methoxide runs to completion in about 1 hour compared to 1-2 days for the same reaction using ammonia. Moreover, a simple methanol or ethanol, preferably ethanol, treatment provides (6) in high purity in the present invention, thereby eliminating a laborious and time-consuming chromatographic purification step that is essential to the prior art process (see FIG. 5, (5a)→(6)).

Despite the greater simplicity, lesser amounts and cost, and increased safety of the reactants and reagents used, the first two steps in the process of the present invention have a combined 85% product yield compared to a 24% product yield observed in the prior art process shown in FIG. 5. The product yield was maintained at about 80+% even while reaction loading was increased from about 5% in the prior art to about 13% in the present invention for the sensitive formamidine-protection step that provides (7) (FIG. 4, (6)→(7)).

A single improvement over the prior art positively affects the next two process steps, silylation-protection and BOC-ester coupling, that provide, for example, (8) and (9). First, the more expensive and difficult to remove pyridine that was used as the reaction solvent in the prior art (FIG. 5, (7)→(8)) is replaced by dichloromethane (FIG. 4, (7)→(8)). Silylation in dichloromethane produces less undesired 3',5'-disilyl derivative, thereby allowing for greater control over disilyl by-product formation and the conversion of more than 99% of (7) into (8). And because dichloromethane also is used as the solvent for coupling with BOC-Val-OH, there is no need for isolation of (8) prior to its coupling with BOC-Val-OH to provide (9). A simple extraction procedure allows for the collection of (8) before it is coupled with BOC-Val-OH (compare FIG. 4, (8)→(9) with the same step in the prior art FIG. 5).

Further, the prior art process employed N,N-dimethylformamide and acetonitrile as the BOC-Val-OH coupling reaction solvents (FIG. 5, (8)→(9a)). Both these reagents are expensive, provide a low loading ratio of about 3% in this reaction, and N,N-dimethylformamide in particular is difficult to remove from the reaction mixture due to its high boiling point. Moreover, approximately 2 days and excess amounts of BOC-Val-OH, EDC and dimethylaminopyridine (DMAP) are required for the reaction to run to completion. These excess reagents are needed to drive the reaction to completion, but their presence complicates product purification in later steps of the process. In addition, the use of excess DMAP triggers racemization of the amino acid moiety of the L-valine derivative.

In contrast to the prior art processes, the use of dichloromethane as a solvent for the coupling reaction in the present invention (FIG. 4, (8)→(9)) allows for a loading ratio of approximately 11% while utilizing approximately half the amount of reagents as employed in the prior art and producing a reaction that runs to completion in about 4-6 hours. The decrease in reaction time and controlled amount of DMAP used in the present invention reduces racemization of the amino acid moiety of the L-valine derivative to less than 0.2% compared to about 6% racemization found in the prior art. Such low racemic levels as 0.2% are within a more pharmaceutically acceptable range for drugs, because they are associated with the greater activity associated with one enantiomer as compared to its counterpart.

The subsequent deprotection of the esterified β-D-2'-C-methyl-cytidine can utilize ammonium fluoride ($NH_4F$) in methanol. Ammonium fluoride ($NH_4F$) in methanol is the reagent of choice for compound deprotection (i.e., removal of the silyl and dimethylformamidine groups) in the reaction of (9) to form (10) (FIG. 4). The prior art process (FIG. 5, (9a)→(10)) employs the same reagents, but uses 10 equivalents of ammonium fluoride, an approximate 3% loading ratio, and requires chromatographic separation to obtain (10) as compared to the use of 4 equivalents of ammonium fluoride, an approximate 10% loading ratio, and no chromatographic separation needed in the present invention. One benefit using less ammonium fluoride with approximately 10 mole equivalents of ethyl acetate in this step of the improved process is that hydrolysis of the BOC-ester (10) to β-D-2'-C-methyl-cytidine, also identified as 4-amino-1-(3,4-dihydroxy-5-hydroxymethyl-3-methyl-tetrahydrofuran-2-yl)-1H-pyrimidin-2-one (6), is held to a minimum. Thus, the process of the present invention is advantageous in its efficient use of reagents and increased loading ratios.

Moreover, (10) is purified using a simple EtOAc/TBME/$H_2O$ treatment, again eliminating the need for chromatographic separation and purification, and thereby eliminating yet another labor-intensive and time-consuming chromatographic purification step. The percent yield of pure (10) following the three steps of silylation, coupling and deprotection, is approximately 60%-99%.

In the final step of the improved process (FIG. 4, (10)→(11)), ethyl alcohol is used as a solvent for deprotecting the 3'-valinyl ester derivative of β-D-2'-C-methyl-cytidine by removal of the BOC-protective group, and the loading ratio is increased from 2% in the prior art to 12% in the present process. Ethyl alcohol in the improved process replaces ethyl acetate used in the prior art as the solvent of choice (FIG. 5, (10)→(11)), and this change results in the observed increase in loading. Selection of ethyl alcohol as a solvent and increased loading ratios result in an increased reaction yield from about 80% in the prior art process to about 95% in the present invention, and in avoidance of contamination due to generation of acetic acid from ethyl acetate. The final product, (11), is obtained in >98% pure form, and L-valine racemization is held to less than 0.2%.

Thus, the overall improved synthesis of the present invention for preparing a prototype compound 3'-O-valinyl ester of β-D-2'-C-methyl-cytidine (2-amino-3-methyl-butyric acid 5-(4-amino-2-oxo-2H-pyrimidin-1-yl)-4-hydroxy-2-hydroxymethyl-4-methyl-tetrahydro-furan-3-yl ester), or a dihydrochloride salt thereof, results in an overall improvement in percent yield of about 26% and a decrease in cycle time of about 80%. The decrease in cycle time is due mainly to the elimination of labor-intensive, time-consuming and costly chromatographic separation and purification procedures. Other important factors include an increase in loading that results in the need to run fewer batches, and the use of easily handleable solvents and reagents. Use of solvents and reagents that are safer and less costly afford additional benefits for using the present process. However, these benefits might be overlooked if the percent yield of product was less than provided by the prior art process. That the process of the present invention affords an approximate 26% increase in yield provides the culminating rationale for its use.

DEFINITIONS AND ALTERNATIVE REAGENTS

As used herein, the term "substantially free of enantiomer" or "substantially in the absence of enantiomer" refers to a nucleoside composition that includes at least 95% to 98% by weight, and even more preferably 99% to 100% by weight, of the designated enantiomer of that nucleoside. In a preferred embodiment, in the methods and compounds of this invention, the compounds are substantially free of enantiomers.

Similarly, the term "isolated" refers to a nucleoside composition that includes at least 85% or 90% by weight, preferably 95% to 98% by weight, and even more preferably 99% to 100% by weight, of the nucleoside, the remainder comprising other chemical species or enantiomers.

The terms "ribonic-gamma-lactone" and "ribonolactone" are used interchangeably throughout, and refer to the compound designated as compound 1 in FIG. 1, or an oxygen-protected derivative thereof.

The term "protected", as used herein and unless specified otherwise, refers to a group that is added to an oxygen, nitrogen or phosphorus atom to prevent its further reaction or for other purposes. A wide variety of oxygen, nitrogen and phosphorus protecting groups are known to those skilled in the art of organic synthesis.

Examples of suitable protecting groups include, but not limited to, benzoyl; substituted or unsubstituted alkyl groups, substituted or unsubstituted aryl groups, substituted or unsubstituted silyl groups; substituted or unsubstituted aromatic or aliphatic esters, such as, for example, aromatic groups like benzoyl, toluoyls (e.g. p-toluoyl), nitrobenzoyl, chlorobenzoyl; ether groups such as, for example, —C—O-aralkyl, —C—O-alkyl, or —C—O-aryl; and aliphatic groups like acyl or acetyl groups, including any substituted or unsubstituted aromatic or aliphatic acyl, —(C=O)-aralkyl, —(C=O)-alkyl, or —(C=O)-aryl; wherein the aromatic or aliphatic moiety of the acyl group can be straight-chained or branched; all of which may be further optionally substituted by groups not affected by the reactions comprising the improved synthesis (see Greene et al., *Protective Groups in Organic Synthesis*, John Wiley and Sons, $2^{nd}$ Edition (1991)). For example, in one embodiment of the invention, the protecting groups are substituted by groups not affected by the reducing agent of choice, preferably Red-Al. For the use of ethers as protective groups, attention is directed to U.S. Pat. No. 6,229,008 to Saischek et al., herein incorporated by reference, wherein it is reported that the use of an ether as a protective group may offer significant advantages, particularly at the 5' position of a pentofuranoside, for stability toward reagents and process conditions. This affords an ultimate advantage for separation, isolation, and purification of the desired product and thus, on the product's percent yield.

The sugar hydroxyl protecting groups can be as nonlimiting examples, silyl, benzoyl, p-toluoyl, p-nitrobenzoyl, p-chlorobenzoyl, acyl, acetyl, —(C=O)-alkyl, and —(C=O)-aryl, all of which may be unsubstituted or substituted by one or more groups not affected by the selected reducing agent. In one embodiment, the sugar hydroxyl protecting group is benzoyl. The amino acid protecting groups are preferably BOC (butoxycarbonyl), —(C=O)-aralkyl, —(C=O)-alkyl or —(C=O)-aryl. In one embodiment of the invention, the amino acid protecting group is BOC (butoxycarbonyl).

Throughout this application, the term "substituted" means single or multiple degrees of substitution by one or more named substituents. Where a single substituent is disclosed or claimed, the compound can be substituted once or more than once by that substituent. Where multiple substituents are disclosed or claimed, the substituted compound can be substituted independently by one or more of the disclosed or claimed substituent moieties, singly or plurally.

The term "alkyl", as used herein and unless specified otherwise, refers to a saturated, straight, branched, or cyclic, primary, secondary or tertiary hydrocarbon of typically $C_1$ to $C_{10}$, and specifically includes methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, methylpentyl and dimethylbutyl. The term includes both substituted and unsubstituted alkyl groups. Moieties with which the alkyl group can be substituted in one or more positions are selected from the group consisting of halo (including fluorine, chlorine, bromine or iodine), hydroxyl (eg. $CH_2OH$), amino (eg., $CH_2NH_2$, $CH_2NHCH_3$ or $CH_2N(CH_3)_2$), alkylamino, arylamino, alkoxy, aryloxy, nitro, azido (eg., $CH_2N_3$), cyano ($CH_2CN$), sulfonic acid, sulfate, phosphonic acid, phosphate or phosphonate, any or all of which may be unprotected or further protected as necessary, as known to those skilled in the art and as taught, for example, in Greene et al., *Protective Groups in Organic Synthesis*, John Wiley and Sons, $2^{nd}$ Edition (1991).

The terms "alkylamino" and "arylamino" include an amino group that has one or more alkyl or aryl substituents, respectively.

The terms "alkaryl" and "alkylaryl" include an alkyl group with an aryl substituent. The terms "aralkyl" and "arylalkyl" refer to an aryl group with an alkyl substituent.

The term "halo" includes chloro, bromo, iodo, and fluoro.

The term "aryl", as used herein, and unless specified otherwise, refers to phenyl, biphenyl or naphthyl. The term includes both substituted and unsubstituted moieties. The aryl group can be substituted with one or more moieties including but not limited to hydroxyl, amino, alkylamino, arylamino, alkoxy, aryloxy, nitro, cyano, sulfonic acid, sulfate, phosphonic acid, phosphate, or phosphonate, any or all of which may be unprotected or further protected as necessary, as known to those skilled in the art and as taught, for example, in Greene et al., *Protective Groups in Organic Synthesis*, John Wiley and Sons, 2$^{nd}$ Edition (1991).

The term "acyl" includes a —C(=O)—R in which the non-carbonyl moiety R is for example, straight, branched, or cyclic alkyl or lower alkyl, alkoxyalkyl including methoxymethyl, aralkyl including benzyl, aryloxyalkyl such as phenoxymethyl, aryl including phenyl optionally substituted with halogen, $C_1$ to $C_4$ alkyl or $C_1$ to $C_4$ alkoxy, sulfonate esters such as alkyl or aralkyl sulphonyl including methanesulfonyl, the mono-, di- or tri-phosphate ester, trityl or monomethoxytrityl, substituted benzyl, trialkylsilyl such as, for example, dimethyl-t-butylsilyl), or diphenylmethylsilyl. Aryl groups in the esters optimally comprise a phenyl group. The term "lower acyl" refers to an acyl group in which the non-carbonyl moiety is lower alkyl.

The terms "carboxylic acid" and "carboxylic acid ester" include the structures RC(=O)OH and RC(=O)O—R', respectively. Here the non-carbonyl moiety, whether R or R', is for example, straight, branched, or cyclic alkyl or lower alkyl, alkoxyalkyl including methoxymethyl, aralkyl including benzyl, aryloxyalkyl such as phenoxymethyl, aryl including phenyl optionally substituted with halogen, $C_1$ to $C_4$ alkyl or $C_1$ to $C_4$ alkoxy. Also intending for inclusion here are sulfonate esters such as alkyl or aralkyl sulphonyl including methanesulfonyl, the mono-, di- or tri-phosphate ester, trityl or monomethoxytrityl, substituted benzyl, trialkylsilyl such as, for example, dimethyl-t-butylsilyl), or diphenylmethylsilyl. Aryl groups in the esters optimally comprise a phenyl group. In all occurrences, R and R' may be the same or may be different substituents.

The term amino acid includes naturally occurring and synthetic α, β, γ, or δ amino acids, and includes but is not limited to, amino acids found in proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In a preferred embodiment, the amino acid is in the L-configuration. In another preferred embodiment, the amino acid is L-valinyl. Alternatively, the amino acid can be a derivative of alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, -βglycinyl, β-serinyl, β-threoninyl, β-cysteinyl, β-tyrosinyl, β-asparaginyl, β-glutaminyl, β-aspartoyl, β-glutaroyl, β-lysinyl, β-argininyl or β-histidinyl.

The term "non-natural amino acid" refers to a carboxylic acid having an amino group terminus but that is not found in nature. The term is intended to embrace both D- and L-amino acids, and any tautomeric or stereoisomeric forms thereof.

The term nucleoside base, includes purine or pyrimidine base. Examples of purine or pyrimidine base include, but are not limited to, adenine, $N^6$-alkylpurines, $N^6$-acylpurines (wherein acyl is C(O)(alkyl, aryl, alkylaryl, or arylalkyl), $N^6$-benzylpurine, $N^6$-halopurine, $N^6$-vinylpurine, $N^6$-acetylenic purine, $N^6$-acyl purine, $N^6$-hydroxyalkyl purine, $N^6$-thioalkyl purine, $N^2$-alkylpurines, $N^2$-alkyl-6-thiopurines, thymine, cytosine, 5-fluorocytosine, 5-methylcytosine, 6-azapyrimidine, including 6-azacytosine, 2- and/or 4-mercaptopyrmidine, uracil, 5-halouracil, including 5-fluorouracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-nitropyrimidine, $C^5$-aminopyrimidine, $N^2$-alkylpurines, $N^2$-alkyl-6-thiopurines, 5-azacytidinyl, 5-azauracilyl, triazolopyridinyl, imidazolopyridinyl, pyrrolopyrimidinyl, and pyrazolo-pyrimidinyl. Purine bases include, but are not limited to, guanine, adenine, hypoxanthine, 2,6-diaminopurine, and 6-chloropurine. Functional oxygen and nitrogen groups on the base can be protected as necessary or desired. Suitable protecting groups are well known to those skilled in the art, and include trimethylsilyl, dimethylhexylsilyl, t-butyldimethylsilyl and t-butyldiphenylsilyl, trityl, alkyl groups, and acyl groups such as acetyl and propionyl, methanesulfonyl, and p-toluenesulfonyl. Alternatively, the purine or pyrimidine base can optionally substituted such that it forms a viable prodrug, which can be cleaved in vivo. Examples of appropriate substituents include acyl moiety, an amine or cyclopropyl (e.g., 2-amino, 2,6-diamino or cyclopropyl guanosine).

Other reagents used in the process of the present invention or the prior art are defined as: BSA (bis(trimethylsilyl)acetamide), TMSCl is chlorotrimethylsilane; TFAA is trifluoroacetic anhydride; TBDPSCl is tert-butyldiphenylsilyl chloride; TBDMSCl is tert-butyldimethylsilyl chloride; and DCM is dichloromethane.

The process of the present invention is not limited to the use of the nucleoside, protected amino acid ester, and reagents exemplified. Suitable alternative reagents for the present invention may be used in place of those given above. For example, TEA (triethylamine) may be replaced by any other suitable amine, including but not limited to diisopropylethylamine, N-ethylmorpholine, or any tertiary aliphatic amine; DME (1,2-dimethoxyethane) may be replaced by any suitable polar aprotic solvent, such as THF (tetrahydrofuran) or any ether; and Red-Al/EtOH (sodium bis[2-methoxyethoxy]-aluminum hydride/ethyl alcohol) in toluene can be replaced by NaHTe, $SmI_2$, $H_2$+Pd-phosphine catalyst, or LiAl (O$^t$Bu)$_3$H (lithium tri-tertiary butyoxy aluminum hydride), all of which produce chemoselective and regioselective reductions, but not by LiAlH$_4$, which results in an open-chain diol. Washes of the product slurry with THF just before and after the addition of MgSO$_4$ may be replaced by washes in acetone. Indeed, for scaled-up procedures, acetone is the preferred solvent.

In addition, DMF (dimethyl formamide) may be replaced by any polar solvent such as, for example, DMSO (dimethyl sulfoxide), although DMF is preferred based upon ease of handling and removability from the reaction mix. EDC (1-[3-(dimethylamino)propyl]-3-ethyl-carbodiimide hydrochloride); also referred to as DEC) may be replaced by any reagent that enables coupling including, but not limited to, CDI (carbonyl diimidazole), BOP reagent (benzotriazol-1-yloxy-tris (dimethylamino)-phosphonium hexafluorophosphate), or similar coupling reagents as known to those skilled in the art. While SnCl$_4$ is preferred, any Lewis acid may be used in its place. The Lewis acid includes, but is not limited to SnCl$_4$, BF$_3$, AlCl$_3$, TiCl$_2$, TiCl$_4$, FeCl$_3$, SnCl$_2$ and any mixture thereof. In one embodiment, the Lewis acid is SnCl$_4$. Any organic solvents such as, for example, toluene may replace acetonitrile. Any activating agent, for example a silylating agent can be used to activate the nucleoside base for coupling. HMDS (hexamethyldisilazane), TMSCl, or TBDPSCl, for example, may be used in place of BSA (bis(trimethylsilyl) acetamide). Ammonia is an alternative reagent for use in place of sodium methoxide in methanol, and any polar solvent such as DMSO may replace DMF. Any number of other silylating reagents may replace TBDPSCl, any fluoride salt can replace NH$_4$F, and other acids such as TFA may be used to replace HCl.

Detailed Description of Process Steps

Preparation of the Ribonolactone

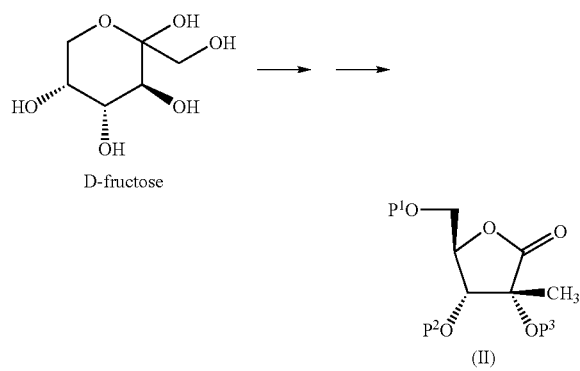

D-fructose

The ribonolactone can be prepared by any published or unpublished means including standard oxidation and substitution techniques. One embodiment of the process for the synthesis of the ribonolactone is synthesized via D-fructose by the following protocol.

The ribonolactone can be prepared by reaction of D-fructose with calcium oxide (CaO). The D-fructose can be reacted with CaO at any molar ratio that allows the reaction to proceed at an acceptable rate without excessive side products, preferably at a 5:1 molar ratio, and even more preferably at a 3:1 molar ratio, and most preferably at a 2.3:1.3 molar ratio to D-fructose. The CaO can be added at any rate that allows for the reaction to proceed at an acceptable rate and without the generation of excess heat or excessive side products. In one embodiment, the CaO is added incrementally over a 5-minute period at room temperature. The reaction can be allowed to proceed until a substantial amount of the D-fructose is consumed, e.g. for 6-22 hours, in which the reaction progression can be monitored, for example by taking aliquots periodically for TLC analysis.

This reaction can be accomplished at any temperature that allows the reaction to proceed at an acceptable rate without promoting decomposition or excessive side products. The preferred temperature is from room temperature to about 23-40° C.

A precipitant can be used to remove calcium from the solution. In one embodiment, $CO_2$ and an acid that is stronger than ribonic acid, and in a preferred embodiment, an organic acid, are added to the reaction mixture to form calcium carbonate. Suitable organic acids include, but are not limited to: oxalic acid, malonic acid, succinic acid, glutaric acid, adipic acid, suberic acid, sebacic acid, azelaic acid, maleic acid, acetic acid, propionic acid, isobutyric acid, acrylic acid, methacrylic acid, butyric acid, pentanoic acid, hexanoic acid or hexanoic acid.

Therefore, in one embodiment of the present invention, $CO_2$ can be bubbled through the mixture at the conclusion of the reaction period for a suitable amount of time to lower the pH from basic to neutral levels, e.g. about 2-3 hours. Any $CaCO_3$ that forms as a result of the neutralization step can be removed, for example by vacuum filtration.

The aqueous layers then can be treated with an acid, such as an organic acid, that is stronger than ribonic acid, for example oxalic acid, at any molar ratio that allows the reaction to proceed at an acceptable rate without excessive side products. In one embodiment, the acid, such as oxalic acid, is added in a 1:2 molar ratio with D-fructose.

The reaction can be allowed to proceed until a substantial amount of calcium is precipitated at any temperature that allows the calcium to precipitate out of solution at an acceptable rate without promoting decomposition or the formation of excessive side products. For example, the solution can be stirred until a white slurry appears, for example around 30 minutes, at about room temperature or around 25° C. Then, this slurry can then be stirred overnight, for example at 45-50° C.

Upon completion, the solution can be evaporated, for example under reduced pressure, to remove most of the water while still leaving an aqueous mix. The product can be isolated from the aqueous mix by any means known in the art. For example, NaCl and an organic solvent, such as THF, can be added into the slurry at room temperature and stirred, for example for approximately 30 minutes. The resulting layers can be separated, and the aqueous layer is added to fresh solvent, such as THF, and stirred, for example for an additional 10 minutes. The process of adding solvent, stirring, and separating the resulting aqueous layer can be repeated as many times as necessary, for example repeated around 3 times. Finally, the organic solutions can be combined and stirred with a drying agent, such as anhydrous $MgSO_4$, for example for 30 minutes, then filtered, and washed with more solvent, such as THF. The filtrate can be evaporated, for example under reduced pressure, at about 40° C., and the crude product can be collected, for example as a dark orange semisolid.

Optionally, to purify the product, a second solvent, such as acetone is added to the crude product, and the mixture is stirred for example at 20° C. for 3 hours. A white crystalline ribonolactone product can be collected for example by vacuum filtration, washed with the second solvent, such as acetone, and vacuum dried (see FIG. 1, compound 1).

Product yield from this reaction can be approximately 13.6%, nearly 4% increase over the product yields found in the prior art.

The free hydroxyl groups of the ribonolactone then can be selectively protected with a suitable protecting group, preferably with an acyl or silyl group, by methods well known to those skilled in the art, as taught in Greene, et al., *Protective Groups in Organic Synthesis*, John Wiley and Sons, Second Edition, 1991. For example, chloro-t-butyl diphenylsilane may be reacted with the ribonolactone at room temperature in anhydrous pyridine. Alternatively, an acyl chloride, such as benzoyl chloride, may be reacted with the ribonolactone, optionally in the presence of a base, under refluxing conditions in DME.

For example, the ribonolactone product can be mixed with a base, for example DMAP in any molar ratio that allows the reaction to proceed at an acceptable rate without excessive side products. In one embodiment, the molar ratio of ribonolactone:base (such as DMAP) is about 5:1. The reaction optionally can be promoted with the use of an additional base, such as TEA in any molar ratio that allows the reaction to proceed at an acceptable rate without excessive side products. In one embodiment of the invention, the additional base (such as TEA) is used in excess. After a sufficient period, an acyl chloride, such as benzoyl chloride, is added in any molar ratio that allows the reaction to proceed at an acceptable rate without excessive side products, for example in approximately a 5:1 ratio with ribonolactone.

The ribonolactone can be prepared in any solvent that is suitable for the temperature and the solubility of the reagents. Solvents can consist of any aprotic solvent including, but not limiting to, alkyl solvents such as hexane and cyclohexane, toluene, acetone, ethyl acetate, dithianes, THF, dioxane, acetonitrile, dichloromethane, dichloroethane, diethyl ether, pyridine, dimethylformamide (DMF), DME, dimethylsulfoxide (DMSO), dimethylacetamide, or any combination thereof, though preferably DME.

This reaction can be accomplished at any temperature that allows the reaction to proceed at an acceptable rate without promoting decomposition or excessive side products. The preferred temperature is from room temperature to about 5° C.

Ice water then can be added to the reaction mixture, after which the crude product is collected, stirred with a suitable solvent, such as tert-butyl methyl ether, filtered, washed, and dried, for example via vacuum.

Figure 2:
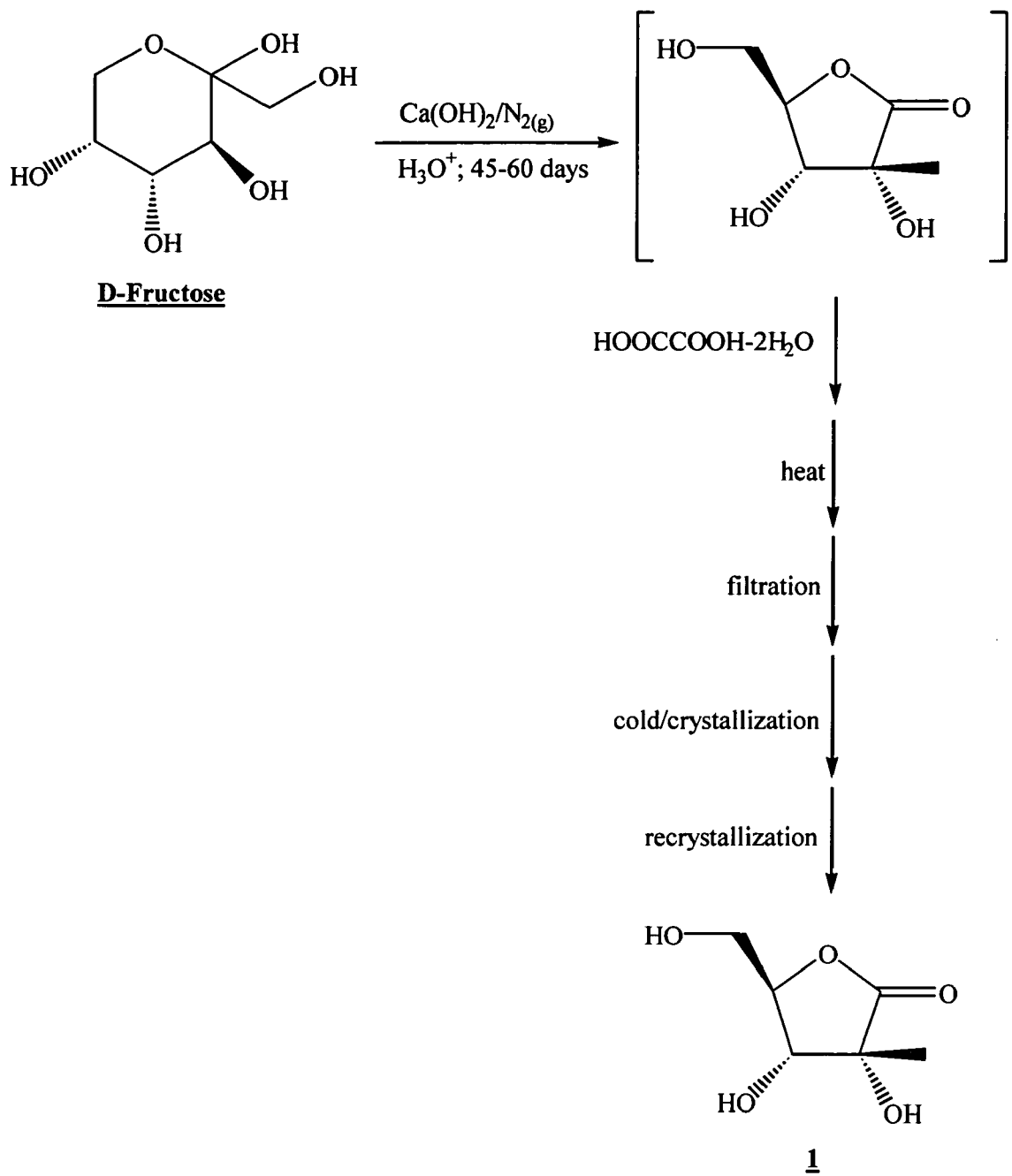
FIG. 2 is a schematic of a alternative process for preparing 2-C-methyl-β-D-ribonolactone.

For comparative purposes, the prior art process of Kiliani for preparing ribonolactone is given in FIG. 2. A detailed account of Kiliani's process as given by Sowden in *Adv. In Carbohydrate Chem.* 1957, 12:43 indicates that $Ca(OH)_2$ is added once and then again 14 days later, after which the mixture is allowed to sit with occasional shaking for 1-2 months. The mixture is then filtered, and the filtrate is saturated with $CO_2$. Next, calcium ions are precipitated by the addition of an exact equivalent amount of oxalic acid, the solution filtered, concentrated to a syrup, and the syrup allowed to crystallize under cold conditions over another few days. Finally, the mother liquors are separated from the crystals, and the crystals dissolved and recrystallized from water.

Reduction of the Protected Ribonolactone

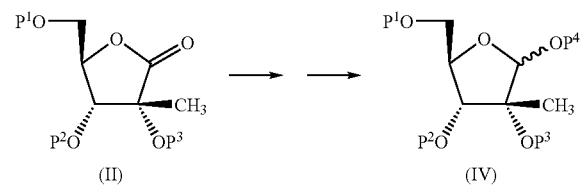

The optionally protected 2-C-methyl-D-ribono-gamma lactone obtained from the previous step can be reduced using any suitable reducing agent at any molar ratio that allows the reaction to proceed at an acceptable rate without excessive side products. Suitable reducing agents include, but are not limited to, Red-Al/EtOH (sodium bis[2-methoxyethoxy]-aluminum hydride/ethyl alcohol), NaHTe, $SmI_2$, $H_2$+Pd-phosphine catalyst, or $LiAl(O^tBu)_3H$ (lithium tri-tertiary butyoxy aluminum hydride), all of which produce chemoselective and regioselective reductions. In one embodiment of the invention, the reducing agent is Red-Al/ethanol. For example, a solution of Red-Al can be added to a solution of optionally protected 2-C-methyl-D-ribono-gamma lactone at a molar ratio of Red-Al to 2,3,5-tri-O-benzoyl-2-C-methyl-D-ribonic-gamma lactone of approximately 2:1.

Interestingly, it is found that certain reagents work less well or result in a mixture of desired and undesired product species when used in the process of the present invention. For example, when Red-Al in ethanol is replaced by $LiAl(O^t—Bu)_3H$, the latter reducing agent slows reaction time and results in the formation of several undesired products. Likewise, 9-borabicyclo-[3.3.1]-nonane, 9-BBN, and diisobutylaluminium hydride, DIBALH, produce no reaction or only trace amounts of the desired product.

This reaction can be accomplished at any temperature that allows the reaction to proceed at an acceptable rate without promoting decomposition or excessive side products. The preferred temperature is from about 0° C. to −5° C.

The ribofuranose can be prepared in any solvent that is suitable for the temperature and the solubility of the reagents. Solvents can consist of any organic solvent including, but not limited to, alkyl solvents such as pentane, hexane and cyclohexane, toluene, acetone, ethyl acetate, dithianes, THF, dioxane, acetonitrile, dichloromethane, dichloroethane, diethyl ether, pyridine, dimethylformamide (DMF), DME, dimethylsulfoxide (DMSO), dimethylacetamide, alcohol solvents such as methanol, ethanol, propanol, isopropanol, butanol, pentanol, and octanol, or any combination thereof, though preferably in a solution of anhydrous toluene and anhydrous ethanol.

The reaction can be quenched with a suitable proton source, such as acetone, water, and 1 N HCl. The mixture can be extracted with organic solvent, such as ethyl acetate, washed with brine, dried, and the solvent removed, for example under pressure at about 40° C.

The free hydroxyl group of the ribofuranose then can be selectively protected with a suitable protecting group, preferably with an acyl or silyl group, by methods well known to those skilled in the art, as taught in Greene, et al., *Protective Groups in Organic Synthesis*, John Wiley and Sons, Second Edition, 1991. For example, chloro-t-butyl diphenylsilane may be reacted with the ribofuranose at room temperature in anhydrous pyridine. Alternatively, an acyl chloride, such as benzoyl chloride, may be reacted with the ribofuranose, optionally in the presence of a base, under refluxing conditions in DME.

Figure 3:
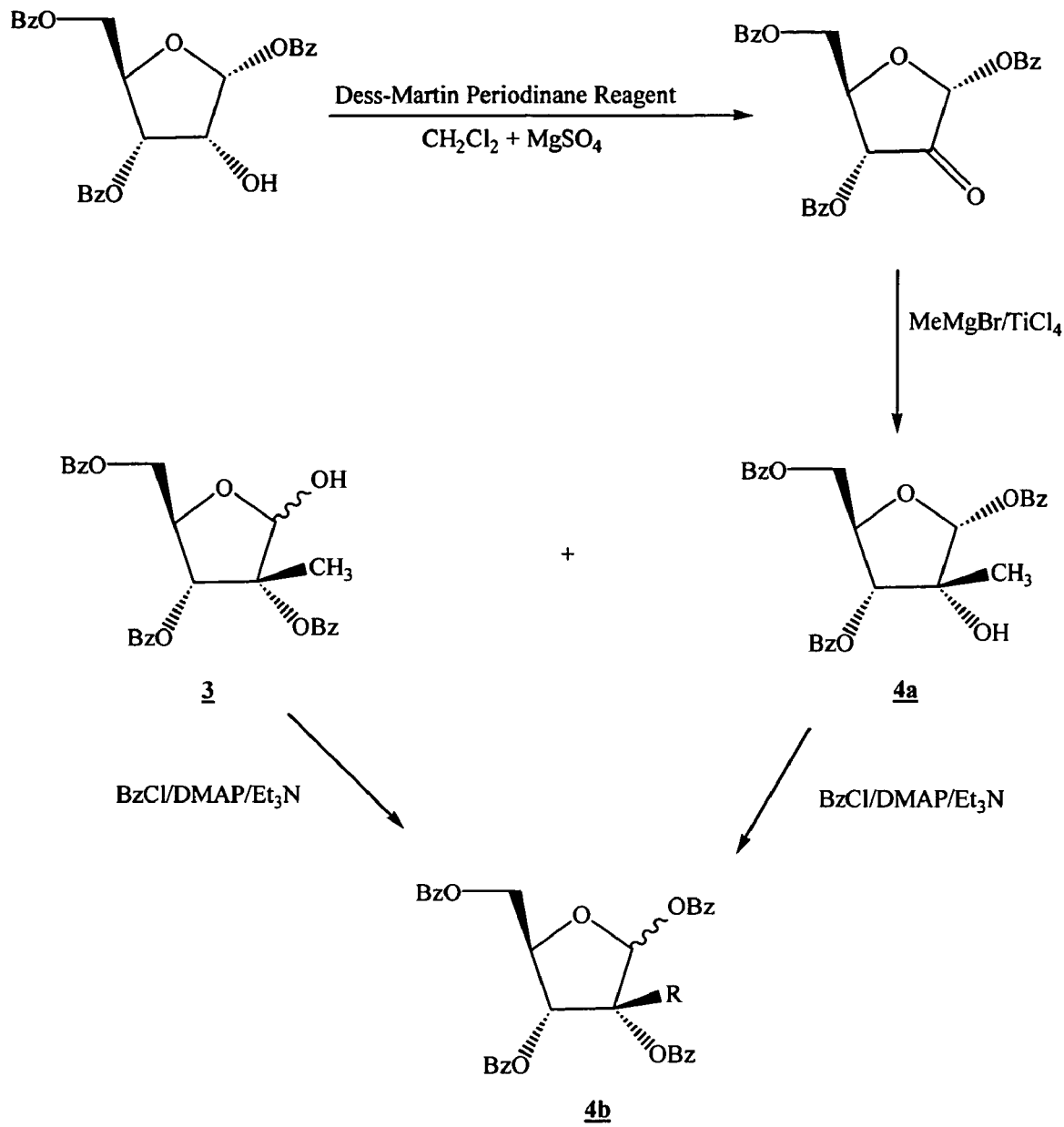
FIG. 3 is a schematic of a alternative process for preparing 1,2,3,5-tetra-O-benzoyl-2-C-methyl-β-D-ribofuranose.

FIG. 3, is an example of an alternative process by Harry-O'kuru et al, *J. Org. Chem.*, (1997), 62(6):1754-59. This process lacks a lactone intermediate but is used to obtain a product identical to that of the present invention. The process of Harry-O'kuru utilized D-arabinose or D-ribose that had all its hydroxy groups except for that at C2 protected prior to ketone formation (FIG. 3). The protected sugar was reacted with Dess-Martin periodinane reagent in $CH_2Cl_2$ and $MgSO_4$ to provide 2,4-di-O-benzoyl-5-methyl-O-benzoyl-dihydrofuran-3-one, which was subsequently reduced with $MeTiCl_3$, $MeMgBr/TiCl_4$ (or $RCeCl_2$ where R is the desired substituent on the ribose C2). Reaction of compounds (3) and (4a) with $BzCl/DMAP/Et_3N$ provides the final product (4b), 1,2,3,5-tetra-O-benzoyl-2-R-ribofuranoside. It is noted that in the first step, a significant amount of a hydrate of the desired product is formed and requires overnight reaction with excess $MgSO_4$ to prepare an essentially dry ketone product. Further, it will be appreciated that a mixture of desired 1,3,5-benzoyl-protected-2-alkyl ribofuranoside, and its transesterified α- and β isomers of 2,3,5-benzoyl-protected ribofuranosides, result from reacting the key intermediate 2-ketone with an organotitanium reagent in this process. While immaterial to the authors because all three products were useful for their purposes, this aspect of the synthesis would require an additional separation step for anyone with an interest in only a single isomer (*J. Org. Chem.*, 1997, 62(6):1754-9, at 1755). Either D-ribose or D-arabinose may be used as the starting material for this process, but economics play a large role when using D-arabinose since its cost is approximately 250 times that of D-fructose!

The prior art process of FIG. 3 differs from the present invention in that all hydroxy groups on the D-arabinose or D-ribose except for that on C2 are protected prior to ketone formation. A ketone then is formed at C2 on the starting compound by reaction with Dess-Martin periodinane reagent (see FIG. 3, compound 3), and is subsequently reduced with $MeTiCl_3$ or $RCeCl_2$, where R is the desired, second substituent on the ribose C2 (see FIG. 3, compounds 3 and 4). The final product, 1,2,3,5-tetra-O-benzoyl-2-alkyl-ribofuranoside, is produced in approximately a 70% yield.

By comparison, the more efficient process of the present invention provides for lactone formation at ribofuranose C1, protection of available hydroxy groups at ribofuranose C2, C3 and C5, and lactone reduction with Red-Al, optionally in ethanol, that produces regioselective, easily separable, anomeric products, followed by protection of the single, remaining free hydroxy group at ribofuranose C1.

Condensation of the Ribofuranose with Activated Cytosine

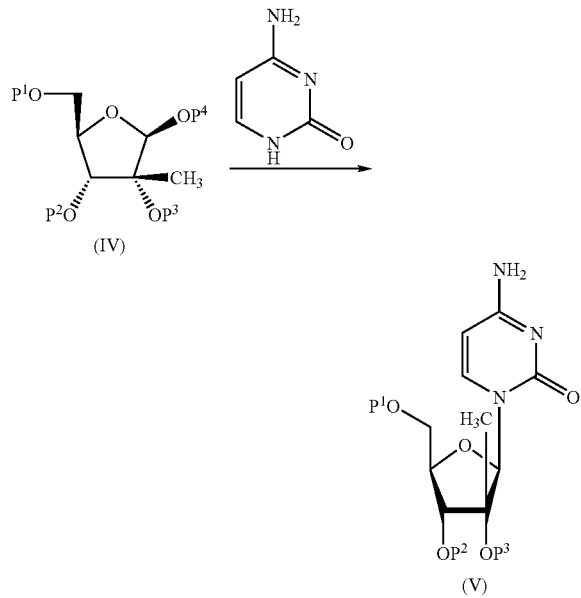

The optionally protected 2-C-methyl-D-ribonofuranose, obtained either from the previous steps or from any other means known in the art, can be coupled with a nucleoside base using any method known in the art, including standard coupling techniques using activated bases.

One embodiment of the present invention includes the process for the synthesis of the β-D-2'-C-methyl-cytidine by the following protocol.

β-D-2'-C-Methyl-cytidine can be prepared by reaction of 2-C-methyl-D-ribonofuranose with an activated cytosine that is unprotected (i.e. not benzoylated), such as an cytosine activated with an activating agent, such as a silylating agent, including, but not limited to BSA ((N,O-bis(trimethylsilyl) acetamide), HMDS, TMSCl, or TBDPSCl. In one embodiment, the silylating agent is BSA.

The reaction can be carried out optionally in the presence of a Lewis acid, such as $SnCl_4$, in any molar ratio that allows the reaction to proceed at an acceptable rate without excessive side products. Suitable Lewis acids includes, but are not limited to $SnCl_4$, $BF_3$, $AlCl_3$, $TiCl_2$, $TiCl_4$, $FeCl_3$, $SnCl_2$ and any mixture thereof. In one embodiment, the Lewis acid is $SnCl_4$.

β-D-2'-C-Methyl-cytidine can be prepared in any solvent that is suitable for the temperature and the solubility of the reagents. Solvents can consist of any aprotic solvent including, but not limiting to, alkyl solvents such as hexane and cyclohexane, toluene, acetone, ethyl acetate, dithianes, THF, dioxane, acetonitrile, dichloromethane, dichloroethane, diethyl ether, pyridine, dimethylformamide (DMF), dimethylsulfoxide (DMSO), dimethylacetamide, or any combination thereof, though preferably acetonitrile.

This reaction can be accomplished at any temperature that allows the reaction to proceed at an acceptable rate without promoting decomposition or excessive side products. The preferred temperature is from about 20° C. to about 80° C.

Subsequently the nucleoside can be deprotected by methods well known to those skilled in the art, as taught in Greene, et al., *Protective Groups in Organic Synthesis*, John Wiley and Sons, Second Edition, 1991. For example, an benzoyl protected hydroxyl moieties can be deprotected with NaOMe in MeOH at around room temperature.

The prior art process shown in FIG. 5 comprised reacting benzoylcytosine, BSA and $SnCl_4$/acetonitrile with 1,2,3,5-tetra-O-benzoyl-2-C-methyl-β-D-ribofuranose (4) to form 4-benzoylamino-1-(3,4-dibenzoyloxy-5-benzoyloxymethyl-3-methyl-tetrahydrofuran-2-yl)-1H-pyrimidin-2-one (5a); reacting (5a) with $NH_3$ in methanol and chromatographically separating the product, 4-amino-1-(3,4-dihydroxy-5-hydroxymethyl-3-methyl-tetrahydro-furan-2-yl)-1H-pyrimidin-2-one (6), also known as β-D-2'-C-methyl-cytidine; reacting (6) with $Me_2NCH(OMe)_2$ in DMF at room temperature for 1.5 hours to form N-[1-(3,4-dihydroxy-5-hydroxymethyl-3-methyl-tetrahydro-furan-2-yl)-2-oxo-1,2-dihydro-pyrimidin-4-yl]-N,N-dimethyl-formamidine (7); reacting (7) with TBDPSCl and pyridine at room temperature for 6 hours to provide N'-{1-[5-(tert-butyl-diphenyl-silanyloxymethyl)-3,4-dihydroxy-3-methyl-tetrahydro-furan-2-yl]-2-oxo-1,2-dihydro-pyrimidin-4-yl}-N,N-dimethyl-formamidine (8); reacting (8) with N-Boc-L-valine, DEC and DMAP in THF/DMF at room temperature for 2 days and subjecting the product formed from this reaction to HPLC in order to provide 2-tert-butoxycarbonylamino-3-methyl-butyric acid 2-(tert-butyl-diphenyl-silanyloxy-methyl)-5-[4-(dimethylaminomethyleneamino)-2-oxo-2H-pyrimidin-1-yl]-4-hydroxy-4-methyl-tetrahydro-furan-3-yl ester (9a); refluxing (9a) with $NH_4F$ in MeOH for about 3 hours to remove the silyl and amino-protecting groups, and subjecting the product to chromatographic purification to provide 2-tert-butoxycarbonylamino-3-methyl-butyric acid-5-(4-amino-2-oxo-2H-pyrimidin-1-yl)-4-hydroxy-2-hydroxymethyl-4-methyl-tetrahydro-furan-3-yl ester (10); and finally reacting (10) with HCl in EtOAc at room temperature to provide 2-amino-3-methyl-butyric acid 5-(4-amino-2-oxo-2H-pyrimidin-1-yl)-4-hydroxy-2-hydroxymethyl-4-methyl-tetrahydro-furan-3-yl ester, dihydrochloride salt (11) as a final product.

Figure 6:
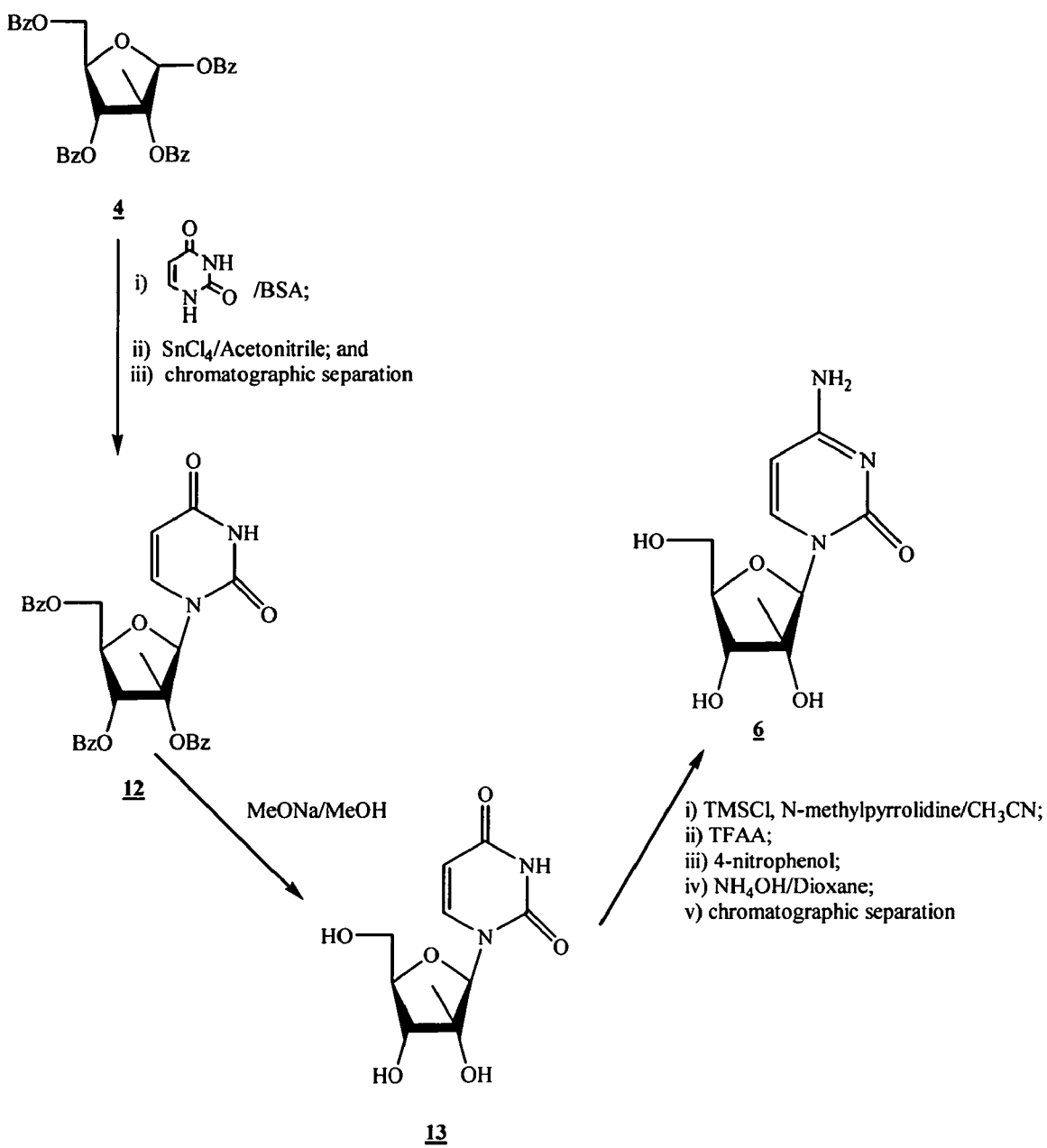
FIG. 6 illustrates an alternative pathway known in the prior art for preparing β-D-2'-C methyl-cytidine.

FIG. 6 is included here as an illustration of an alternative pathway known in the prior art for preparing β-D-2'-C-methyl-cytidine (6). This prior art process employed uracil as a starting material and comprised reacting uracil and BSA in acetonitrile with 1,2,3,5-tetra-O-benzoyl-2-C-methyl-β-D-ribofuranose (4) for about 30 minutes, adding the Lewis acid $SnCl_4$ in acetonitrile, refluxing the resultant solution for about 4 hours, and chromatographically separating the product, 1-(3,4-dibenzoyloxy-5-benzoyloxy-methyl-3-methyl-tetrahydro-furan-2-yl)-1H-pyrimidin-2,4-dione (2); reacting (12) with NaOMe in methanol for approximately 4.5 hours to remove the benzoyl protecting groups, then isolating and crystallizing the product, 1-(3,4-dihydroxy-5-hydroxymethyl-3-methyl-tetrahydro-furan-2-yl)-1H-pyrimidin-2,4-dione (13), also known as β-D-2'-C-methyl-uridine; and finally reacting (13) sequentially with TMSCl and N-methyl pyrrolidine in $CH_3CN$ for about 3.5 hours, cooling and adding trifluoroacetic anhydride (TFAA) for about 30 minutes, adding 4-nitrophenol at 0° C. and stirring for about 3 hours, adding $NH_4OH$ in dioxane with heating to 50° C. overnight, and separating the final product β-D-2'-C-methyl-cytidine (6) by chromatographic procedures and crystallization.

Esterification of the β-D-2'-C-methyl-cytidine

The optionally protected β-D-2'-C-methyl-cytidine, obtained either from the previous steps or from any other means known in the art, can be esterified by any means known in the art.

One embodiment of the present invention includes the process for the synthesis of the 3'-ester of β-D-2'-C-methyl-cytidine, and in particular the 3'-valinyl ester of β-D-2'-C-methyl-cytidine, by the following protocol.

The 3'-ester of β-D-2'-C-methyl-cytidine can be prepared by optionally protecting the amine of β-D-2'-C-methyl-cytidine by any means known in the art., for example as taught in Greene, et al., *Protective Groups in Organic Synthesis*, John Wiley and Sons, Second Edition, 1991. In one embodiment of the present invention, β-D-2'-C-methyl-cytidine can be reacted with $Me_2NCH(OMe)_2$ in DMF to form N-[1-(3,4-dihydroxy-5-hydroxymethyl-3-methyl-tetrahydro-furan-2-yl)-2-oxo-1,2-dihydro-pyrimidin-4-yl]-N,N-dimethylformamidine.

In a particular embodiment, the compound can then be further protected with TBDPSCl and imidazole to provide the 5'-silyl-protected compound, N'-{1-[5-(tert-butyl-diphenyl-silanyloxymethyl)-3,4-dihydroxy-3-methyl-tetrahydrofuran-2-yl]-2-oxo-1,2-dihydro-pyrimidin-4-yl}-N,N-dimethyl-formamidine in any solvent that is suitable for the temperature and the solubility of the reagents. Solvents can consist of any aprotic solvent including, but not limiting to, alkyl solvents such as hexane and cyclohexane, toluene, acetone, ethyl acetate, dithianes, THF, dioxane, acetonitrile, dichloromethane (DCM), dichloroethane, diethyl ether, pyridine, dimethylformamide (DMF), dimethylsulfoxide (DMSO), dimethylacetamide, or any combination thereof, though preferably DCM.

The optionally protected β-D-2'-C-methyl-cytidine then can be coupled with any suitable moiety to obtain a pharmaceutically acceptable 3'-prodrug of β-D-2'-C-methyl-cytidine using any means known in the art, including standard condensation reactions. The moiety can be a phosphate (including mono-, di- or triphosphate and a stabilized phosphate); straight chained, branched or cyclic alkyl (including lower alkyl); acyl (including lower acyl); CO-alkyl, CO-aryl, CO-alkoxyalkyl, CO-aryloxyalkyl, CO-substituted aryl, sulfonate ester (including alkyl or arylalkyl sulfonyl including methanesulfonyl); benzyl, wherein the phenyl group is optionally substituted with one or more substituents as described in the definition of aryl given herein; alkylsulfonyl, arylsulfonyl, aralkylsulfonyl, lipid (including a phospholipid); amino acid; carbohydrate; peptide; cholesterol; or a pharmaceutically acceptable leaving group that provides a free hydroxyl (or phosphate) when administered in vivo.

In one embodiment of the present invention, the desired 3'-prodrug is the 3'-valinyl ester of β-D-2'-C-methyl-cytidine and is prepared according to the following protocol.

The 3'-valinyl ester of β-D-2'-C-methyl-cytidine can be prepared by reacting an optionally protected β-D-2'-C-methyl-cytidine (for example a 5'- and N-protected β-D-2'-C-methyl-cytidine) with N—Boc-L-valine, optionally in the presence of a coupling agent, such as EDC, in the presence of a base, such as DMAP to form 2-tert-butoxycarbonylamino-3-methyl-butyric acid 2-(tert-butyl-diphenyl-silanyloxy-methyl)-5-[4-(dimethylamino-methyleneamino)-2-oxo-2H-pyrimidin-1-yl]-4-hydroxy-4-methyl-tetrahydro-furan-3-yl ester.

The 3'-valinyl ester of β-D-2'-C-methyl-cytidine can be prepared in any solvent that is suitable for the temperature and the solubility of the reagents. Solvents can consist of any aprotic solvent including, but not limiting to, alkyl solvents such as hexane and cyclohexane, toluene, acetone, ethyl acetate, dithianes, THF, dioxane, acetonitrile, dichloromethane (DCM), dichloroethane, diethyl ether, pyridine, dimethylformamide (DMF), dimethylsulfoxide (DMSO), dimethylacetamide, or any combination thereof, though preferably DCM.

This reaction can be accomplished at any temperature that allows the reaction to proceed at an acceptable rate without promoting decomposition or excessive side products. The preferred temperature is around room temperature.

Subsequently the 3'-valinyl ester of β-D-2'-C-methyl-cytidine can be deprotected by methods well known to those skilled in the art, as taught in Greene, et al., *Protective Groups in Organic Synthesis*, John Wiley and Sons, Second Edition, 1991. In one particular embodiment of the invention, the t-butyldiphenylsilyl protected 5'-OH and N—Boc protected L-valine can be deprotected with $NH_4F$ in MeOH in the presence of approximately 10 mole equivalents of ethyl acetate (to prevent cleavage of the 3'-O-valinyl ester by liberated ammonia), and refluxing the mixture to provide 2-tert-butoxycarbonylamino-3-methyl-butyric acid 5-(4-amino-2-oxo-2H-pyrimidin-1-yl)-4-hydroxy-2-hydroxymethyl-4-methyl-tetrahydro-furan-3-yl ester.

The 3'-valinyl ester can be made into a salt by any means known in the art, including, reacting the 3'-valanyl ester of β-D-2'-C-methyl-cytidine with HCl in EtOH to provide 2-amino-3-methyl-butyric acid 5-(4-amino-2-oxo-2H-pyrimidin-1-yl)-4-hydroxy-2-hydroxymethyl-4-methyl-tetrahydro-furan-3-yl ester, dihydrochloride salt as a final product.

Preferred Embodiments

One preferred embodiment of the present invention is exemplified in FIG. 1 and comprises reacting D-fructose in the presence of CaO/water at 23-40° C. for 6-22 hours, and then adding $CO_2$ and oxalic acid to the reaction mixture and allowing the reaction to proceed for 8-12 hours to form 2-C-methyl-D-ribonic-γ-lactone (1); reacting 2-C-methyl-D-ribonic-γ-lactone (1) with 4-dimethylaminopyridine (DMAP) and triethylamine (TEA) in 1,2-dimethoxyethane (DME) at temperature of from about 5° C. to 25° C. for about 30 minutes, and then cooling the mixture to about 5° C. and adding benzoyl chloride to provide 2,3,5-tri-O-benzoyl-2-C-methyl-D-ribonic-γ-lactone (2); reacting 2,3,5-tri-O-benzoyl-2-C-methyl-D-ribonic-γ-lactone (2) with Red-Al/ethanol in toluene at a temperature of from about −5 to 0° C. for about 40 minutes to provide 2,3,5-tri-O-benzoyl-2-C-methyl-β-D-ribofuranose (3); and finally adding benzoyl chloride/TEA to a cold solution of 2,3,5-tri-O-benzoyl-2-C-methyl-β-D-ribofuranose (3) in the presence of DMAP and DME and allowing the reaction to proceed for from about 4 hours to about 12 hours at a temperature of from about 5 to about 50° C., thereby providing the final product (4), 2,3,5-tri-O-benzoyl-2-C-methyl-β-D-ribofuranose.

Specifically, an aqueous solution of D-fructose is prepared at room temperature, and CaO at preferably a 5:1 molar ratio, and even more preferably at a 3:1 molar ratio, and most preferably at a 2.3:1.3 molar ratio to D-fructose, is added incrementally over a 5-minute period. The reaction is allowed to proceed for 6-22 hours at 23-40° C. with aliquots periodically withdrawn for TLC analysis.

At the conclusion of the reaction period, $CO_2$ is bubbled through the mixture for about 2-3 hours in order to lower the pH from basic to neutral levels. Any $CaCO_3$ that forms as a result of the neutralization step is removed by vacuum filtration. The aqueous layers are combined, treated with oxalic acid (or other organic acid) in a 1:2 molar ratio with D-fructose, and stirred at 25° C. for about 30 minutes until a white slurry appears. This slurry then is stirred overnight at 45-50° C., and evaporated under reduced pressure to remove most of the water while still leaving an aqueous mix. Next, NaCl and THF are added into the slurry at room temperature and stirred for approximately 30 minutes. The resulting layers are separated, and the aqueous layer is added to fresh THF and stirred for an additional 10 minutes. The process of adding THF, stirring, and separating the resulting aqueous layer is repeated 3 times. Finally, all THF solutions are combined and stirred with anhydrous MgSO$_4$ for 30 minutes, the mixture is filtered, and the MgSO$_4$ filter cake washed with THF. The filtrate is evaporated under reduced pressure, at about 40° C., and the crude product is collected as a dark orange semisolid.

Next, acetone is added to the crude product, and the mixture is stirred at 20° C. for 3 hours. The white crystalline ribonolactone product is collected by vacuum filtration, washed with acetone, and vacuum dried (see FIG. 1, compound 1, Scheme 1). Product yield from this reaction is approximately 13.6%, a nearly 4% increase over the product yields found in the prior art.

The ribonolactone product obtained then is mixed with DMAP in a molar ratio of about 5:1 (ribonolactone:DMAP), excess TEA, and DME, and stirred for about 30 minutes at room temperature. The resulting suspension is cooled to 5° C., and benzoyl chloride is added in an approximate 5:1 ratio with ribonolactone. The mixture is stirred at room temperature for about 4 hours, when complete consumption of the starting material is confirmed by TLC. Ice water is then added to the reaction mixture and stirred for approximately 30 minutes, after which the crude product is collected, stirred with tert-butyl methyl ether, filtered, washed, and vacuum dried. The white solid product collected is 2,3,5-tri-O-benzoyl-2-C-methyl-D-ribonic-gamma lactone in an 83.4% yield and nearly 98% purity (see FIG. 1, compound 2).

The 2,3,5-tri-O-benzoyl-2-C-methyl-D-ribono-gamma lactone obtained from the previous step is chilled to about −5° C., and has added to it a solution of Red-Al in anhydrous toluene and anhydrous ethanol previously mixed at about 0° C. The molar ratio of Red-Al to 2,3,5-tri-O-benzoyl-2-C-methyl-D-ribonic-gamma lactone is approximately 2:1. The mixture is stirred for about 40 minutes while held at a steady temperature of about −5° C. Aliquots of the mixture are removed and tested by TLC and/or HPLC to confirm consumption of the starting material, after which the reaction is quenched with acetone, water and 1 N HCl, and brought to room temperature. Finally the mixture is extracted with ethyl acetate, washed with brine, dried, and the solvent removed under pressure at about 40° C. The resulting product, 2,3,5-tri-O-benzoyl-2-C-methyl-D-ribofuranose, is obtained in quantitative yield from the amount of 2,3,5-tri-O-benzoyl-2-C-methyl-D-ribono-gamma-lactone used at the start of this step (see FIG. 1, compound 3).

The protective group at C-1 of the ribofuranose is made in the immediately preceding step. Benzoyl chloride is added to a 5° C. solution of 2,3,5-tri-O-benzoyl-2-C-methyl-D-ribofuranose in approximately a 2:1 molar ratio, along with DMAP and TEA in anhydrous DME. The reaction is stirred and allowed to run overnight, after which it is quenched with ice water and aqueous sodium carbonate solution. THF is then removed, and the mixture is extracted with ethyl acetate. Washing, drying and solvent removal produces a thick, oily product. The latter has added to it tert-butyl methyl ether, heptane and water, and is stirred for approximately 2 hours at about 20° C. The final product, 1,2,3,5-tetra-O-benzoyl-2-C-methyl-β-D-ribofuranose, is obtained in 52% yield and greater than 98% purity, after washing and vacuum drying (see FIG. 1, compound 4, Scheme 1).

Another preferred embodiment of the present invention is exemplified in FIG. 4, and comprises reacting cytosine, BSA and SnCl$_4$/acetonitrile with 1,2,3,5-tetra-O-benzoyl-2-C-methyl-β-D-ribofuranose (4) from the first embodiment of the invention to provide 4-amino-1-(3,4-dibenzoyloxy-5-benzoyloxymethyl-3-methyl-tetrahydrofuran-2-yl)-1H-pyrimidin-2-one (5); and reacting (5) with NaOMe/MeOH to provide (4-amino-1-(3,4-dihydroxy-5-hydroxymethyl-3-C-methyl-tetrahydrofuran-2-yl)-1H-pyrimidin-2-one) (6), also known as β-D-2'-C-methyl-cytidine. The use of cytosine as a starting material rather than benzoyl-cytosine improves the "atom economy" of the process and simplifies purification at later steps.

The synthesis may be terminated with the formation of (6), and the product isolated by steps known to those of skill in the art. Alternatively, the synthesis may be carried further to prepare the 3'-O-valinyl ester of β-D-2'-C-methyl-cytidine (2-amino-3-methyl-butyric acid 5-(4-amino-2-oxo-2H-pyrimidin-1-yl)-4-hydroxy-4-C-methyl-2-hydroxymethyl-tetrahydrofuran-3-yl ester) or its preferred hydrochloride salt form, the fourth preferred embodiment of the invention.

In another preferred embodiment of the present invention, compound (6) is reacted with Me$_2$NCH(OMe)$_2$ in DMF to form (7), N-[1-(3,4-dihydroxy-5-hydroxymethyl-3-methyl-tetrahydro-furan-2-yl)-2-oxo-1,2-dihydro-pyrimidin-4-yl]-N,N-dimethylformamidine, which is the amino-protected form of (i); reacting (2) with TBDPSCl and imidazole in DCM to provide the 5'-silyl-protected form of (6) as N'-{1-[5-(tert-butyl-diphenyl-silanyloxymethyl)-3,4-dihydroxy-3-methyl-tetrahydro-furan-2-yl]-2-oxo-1,2-dihydro-pyrimidin-4-yl}-N,N-dimethyl-formamidine (8), where the use of DCM provides the advantage of having greater control over disilyl by-product formation; reacting (8) with N—Boc-L-valine, EDC and DMAP in DCM at room temperature to form 2-tert-butoxycarbonylamino-3-methyl-butyric acid 2-(tert-butyl-diphenyl-silanyloxy-methyl)-5-[4-(dimethylamino-methyleneamino)-2-oxo-2H-pyrimidin-1-yl]-4-hydroxy-4-methyl-tetrahydro-furan-3-yl ester (2); removing the silyl and amino-protecting groups by reacting (9) with NH$_4$F in MeOH in the presence of approximately 10 mole equivalents of ethyl acetate to prevent cleavage of the 3'-O-valinyl ester by liberated ammonia, and refluxing the mixture to provide 2-tert-butoxycarbonylamino-3-methyl-butyric acid 5-(4-amino-2-oxo-2H-pyrimidin-1-yl)-4-hydroxy-2-hydroxymethyl-4-methyl-tetrahydro-furan-3-yl ester (10); and finally, reacting (10) with HCl in EtOH to provide 2-amino-3-methyl-butyric acid 5-(4-amino-2-oxo-2H-pyrimidin-1-yl)-4-hydroxy-2-hydroxymethyl-4-methyl-tetrahydro-furan-3-yl ester, dihydrochloride salt (11) as a final product.

This invention is further illustrated in the following non-limiting examples. The working examples contained herein are set forth to aid in understanding the invention. They are illustrative of the process(es) and product(s) of the invention, but are not intended to and should not be interpreted to in any way limit the invention set forth in the claims that follow thereafter. Equivalent, similar or suitable solvents, reagents, or reaction conditions may be substituted for those particular solvents, reagents, and/or reaction conditions described herein without departing from the spirit and scope of the invention.

EXAMPLES

Example 1

2-C-Methyl-D-ribonic-γ-lactone

De-ionized water (100 mL) was stirred in a 250 mL 3-necked round bottom flask, equipped with an overhead stirrer, a stirring shaft, a digital temperature read-out device and an argon line. Argon was bubbled into water for thirty minutes and D-fructose (20.0 g, 0.111 mole) was added and the solution became clear in a few minutes. Calcium oxide (12.5 g, 0.223 mole) was added in portions over a period of five minutes and the mixture was vigorously stirred. An exotherm was observed and reaction temperature reached 39.6° C. after 10 minutes from the start of the calcium oxide addition. After about fifteen minutes, the reaction mixture developed a yellow color that deepened with time. After three hours, an aliquot was withdrawn for TLC analysis. The aliquot was acidified to pH 2 using saturated aqueous solution of oxalic acid. The resulting white suspension was evaporated under reduced pressure to remove the water. Toluene (2 mL) was added to the residue and the mixture was evaporated under reduced pressure (at 45-50° C.) to remove any trace of water. The residual solid was re-constituted in 2 mL of 1:1 tetrahydrofuran:methanol mixture. After thorough mixing, the suspension was allowed to settle and the supernatant clear solution was spotted for TLC (silica plate was developed in 2% methanol in ethyl acetate and stained in 1% alkaline potassium permanganate dip. The plate was then heated, using a heat gun, until the appearance of yellowish spots on the pink background). The desired lactone typically appears at an $R_f$ value of 0.33 under the above conditions. More polar by-products and unreacted material are detected in the $R_f$ value range of 0.0 to 0.2.

Although product formation was observed after 3 hours, the reaction was allowed to continue for 22 hours during which time the reaction mixture was stirred at 25° C. At the end of this period, pH of the mixture was 13.06. Carbon dioxide gas was bubbled into the reaction mixture for about 2.5 hours (pH was 7.25). The formed calcium carbonate solid was removed by vacuum filtration, filter cake washed with 50 mL of de-ionized water. The aqueous layers were combined and treated with oxalic acid (5.0 g, 0.056 mole) and the mixture was vigorously stirred at 25° C. for 30 minutes (The initial dark color largely disappeared and the mixture turned into a milky white slurry). The pH of the mixture at this stage is typically 2-3. The slurry mixture was stirred at 45-50° C. overnight. The mixture was then evaporated under reduced pressure and at 45-50° C. to remove 75 mL of water. Sodium chloride (30 g) and tetrahydrofuran (100 mL) were added to the aqueous slurry (about 75 mL) and the mixture was vigorously stirred at 25° C. for 30 minutes. The layers were separated and the aqueous layer was stirred for 10 minutes with 75 mL of fresh tetrahydrofuran. This process was repeated for three times and the tetrahydrofuran solutions were combined and stirred with 10 g of anhydrous magnesium sulfate for 30 minutes. The mixture was filtered and the magnesium sulfate filter cake was washed with 60 mL of tetrahydrofuran. The filtrate was evaporated under reduced pressure and at 40° C. to give 10.86 g of crude product as a dark orange semisolid. (For scale up runs tetrahydrofuran will be replaced with acetone instead of evaporation of crude product to dryness). Crude product was stirred with acetone (20 mL) at 20° C. for 3 hours. Product was collected by vacuum filtration and the filter cake washed with 12 mL of acetone to give the desired product 1 as white crystalline solid. Product was dried in vacuum to give 2.45 g (13.6% yield). Melting point of compound 1: 158-162° C. (literature melting point: 160-161° C.). $^1$H NMR (DMSO-$d_6$) δ ppm 5.69 (s, 1H, exch. with $D_2O$), 5.41 (d, 1H, exch. with $D_2O$), 5.00 (t, 1H, exch. with $D_2O$), 4.15 (m, 1H), 3.73 (m, 2H), 3.52 (m, 1H), 1.22 (s, 3H). $^{13}$C NMR (DMSO-$d_6$) δ ppm 176.44, 82.95, 72.17, 72.02, 59.63, 20.95. ($C_6H_{10}O_5$: calcd C, 44.45; H, 6.22. Found: C, 44.34; H, 6.30).

Example 2

2,3,5-Tri-O-benzoyl-2-C-methyl-D-ribonic-γ-lactone

A mixture of lactone 1 (3.0 g, 18.50 mmol.), 4-dimethylaminopyridine (0.45 g, 3.72 mmol.) and triethylamine (25.27 g, 249.72 mmol.) in 1,2-dimethoxy ethane (50 mL) was stirred at 25° C. under argon atmosphere for thirty minutes. This white suspension was cooled to 5° C. and benzoyl chloride (11.7 g, 83.23 mmol.) was added over a period of fifteen minutes. The mixture was stirred at 25° C. for two hours. TLC analysis (silica, 2% methanol in ethyl acetate) indicated complete consumption of starting material. Ice cold water (100 g) was added to the reaction mixture and stirring was continued for thirty minutes. The formed white solids were collected by vacuum filtration and filter cake washed with cold water (50 mL). This crude product was stirred with tert-butyl methyl ether (60 mL) at 20° C. for thirty minutes, then filtered, filter cake washed with tert-butyl methyl ether (25 mL) and dried in vacuum to give 7.33 g (83.4% yield) of compound 2 as a white solid in 97.74% purity (HPLC/AUC). Melting point of compound 2: 137-140° C. (literature melting point: 141-142° C.). $^1$H NMR (CDCl$_3$) δ ppm 8.04 (d, 2H), 7.92 (d, 2H), 7.73 (d, 2H), 7.59 (t, 1H), 7.45 (m, 4H), 7.32 (t, 2H), 7.17 (t, 2H), 5.51 (d, 1H), 5.17 (m, 1H), 4.82-4.66 (d of an AB quartet, 2H) 1.95, (s, 3H). $^{13}$C NMR (CDCl$_3$) δ ppm 172.87, 166.17, 166.08, 165.58, 134.06, 133.91, 133.72, 130.09, 129.85, 129.80, 129.37, 128.78, 128.60, 128.49, 127.96, 127.89, 79.67, 75.49, 72.60, 63.29, 23.80. TOF MS ES+ (M+1: 475).

Example 3

2,3,5-Tri-O-benzoyl-2-C-methyl-βD-ribofuranose

A solution of Red-Al (65 wt. % in toluene, 2.0 mL, 6.56 mmol.) in anhydrous toluene (2.0 mL) was stirred at 0° C. under argon atmosphere. A solution of anhydrous ethanol (0.38 mL, 6.56 mmol.) in anhydrous toluene (1.6 mL) was added to the toluene solution over a period of five minutes. The resulting mixture was stirred at 0° C. for fifteen minutes and 2 mL (2.18 mmol.) of this Red-Al/ethanol reagent was added to a cold (−5° C.) solution of 2,3,5-tri-O-benzoyl-2-C-methyl-D-ribonolactone 2 (475 mg, 1.0 mmol.) in anhydrous toluene (10 mL) over a period of 10 minutes. The reaction mixture was stirred at −5° C. for forty minutes. TLC analysis (silica plates, 35% ethyl acetate in heptane) indicated complete consumption of starting material. HPLC analysis indicated only 0.1% of starting material remaining. The reaction was quenched with acetone (0.2 mL), water (15 mL) and 1 N HCl (15 mL) at 0° C. and allowed to warm to room temperature. 1 N HCl (5 mL) was added to dissolve the inorganic salts (pH: 2-3). The mixture was extracted with ethyl acetate (3×25 mL) and the organic solution washed with brine (25 mL), dried (anhydrous sodium sulfate, 10 g) and solvent removed under reduced pressure and at temperature of 40° C. to give the desired product 3 in quantitative yield (480 mg). This material was used as is for the subsequent step.

Example 4

1,2,3,5-tetra-O-benzoyl-2-C-methyl-βD-ribofuranose

Benzoyl chloride (283 mg, 2.0 mmol.) was added, over a period of five minutes, to a cold solution (5° C.) of compound 3 (480 mg, 1.0 mmol.), 4-dimethylaminopyridine (12.3 mg, 0.1 mmol.) and triethylamine (506 mg, 5.0 mmol.) in anhydrous tetrahydrofuran (5 mL). The reaction mixture was stirred at room temperature and under argon atmosphere overnight. HPLC analysis indicated 0.25% of un-reacted starting material. The reaction was quenched by adding ice-cold water (10 g) and saturated aqueous solution of sodium bicarbonate. Tetrahydrofuran was removed under reduced pressure and the mixture was extracted with ethyl acetate (50 mL). The organic solution was washed with water (25 mL), brine (25 mL), dried (anhydrous sodium sulfate, 12 g) and solvent removed under reduced pressure to give 650 mg of thick oily product. This crude product was stirred with 5 mL of tert-butyl methyl ether for 5 minutes and heptane (5 mL) and water (0.1 mL) were added and stirring was continued for an additional period of two hours at 20° C. Solids were collected by vacuum filtration and filter caked washed with 1:1 heptane:tert-butyl methyl ether solution (6 mL) and tert-butyl methyl ether (2 mL). Drying the solid in vacuum gave 300 mg (52%) of desired product 4 (98.43% pure by HPLC/AUC) as a white solid that melted at 154-156.3° C. (literature melting point: 155-156° C.). $^1$H NMR (CDCl$_3$) δ ppm 8.13 (m, 4H), 8.07 (d, 2H), 7.89 (d, 2H), 7.63 (m, 3H), 7.48 (m, 6H), 7.15 (m, 3H), 7.06 (s, 1H), 5.86 (dd, 1H), 4.79 (m, 1H), 4.70-4.52 (d of an AB quartet, 2H), 1.95, (s, 3H). $^{13}$C NMR (CDCl$_3$) δ ppm 166.31, 165.83, 165.01, 164.77, 134.01, 133.86, 133.70, 133.17, 130.44, 130.13, 129.97, 129.81, 129.59, 129.39, 129.07, 128.84, 128.76, 128.37, 98.01, 86.87, 78.77, 76.35, 64.05, 17.07. (C$_{34}$H$_{28}$O$_9$: calcd C, 70.34; H, 4.86. Found: C, 70.20; H, 4.95).

Example 5

4-Amino-1-(3,4-dibenzoyloxy-5-benzyloxymethyl-3-methyl-tetrahydro-furan-2-yl)-1H-pyrimidine-2-one: (Compound 2, FIG. 4)

Cytosine (89 g, 0.80 mol) was suspended in acetonitrile (900 ml) in a 12 L round bottomed flask equipped with a reflux condenser, overhead stirrer and an argon inlet adapter. The suspension was stirred at 20° C. under argon atmosphere and N,O-bis(trimethylsilyl)acetamide (537 ml, 2.2 mol) was added in one portion. The resulting solution was heated to 80° C. and stirred for an additional hour at the same temperature. 1,2,3,5-tetra-O-benzoyl-2-C-methyl-β-D-ribofuranose (425.0 g, 0.73 mol) was suspended in acetonitrile (4000 ml) and added to the reaction mixture. The reaction mixture became clear after a few minutes and the temperature dropped to ca. 50° C. Tin(IV) chloride (154 ml, 1.31 mol) was added over a period of 15 minutes and stirring was continued at 80°. After one hour, an aliquot of reaction mixture was quenched by adding aqueous sodium bicarbonate solution and extracting the aqueous layer with ethyl acetate. The ethyl acetate layer was examined by TLC (silica gel, 20% ethyl acetate in heptane, R$_f$ for sugar derivative: 0.40). TLC analysis indicated the complete consumption of the sugar derivative. Desired product was detected by TLC using 10% methanol in dichloromethane (R$_f$: 0.37). The reaction was also monitored by HPLC (Method # 2). The reaction mixture was cooled to 20° C. and quenched by adding saturated aqueous sodium bicarbonate solution (3000 mL) over a period of 30 minutes (observed an exotherm when added the first few milliliters of the sodium bicarbonate solution). Solid sodium bicarbonate (1350 g) was added in portions to avoid foaming. The mixture was checked to make sure that its pH is ≧7. Agitation was stopped and layers were allowed to separate for 20 minutes. The aqueous layer was drained and stirred with ethyl acetate (1500 ml) and the mixture was allowed to separate (30 minutes). The organic layer was isolated and combined with the acetonitrile solution. The organic solution was washed with brine (500 ml) and then solvent stripped to a volume of ca. 750 ml. Product can be used as is in the subsequent reaction. It may also be further stripped to white foamy solid, in quantitative yield. Structure of compound (2) was confirmed by $^1$H NMR analysis.

Example 6

4-Amino-1-(3,4-dihydroxy-5-hydroxymethyl-3-methyl-tetrahydro-furan-2-yl)-1H-pyrimidine-2-one: (Compound 3)

Sodium methoxide (13.8 g, 0.26 mol) was added to a solution of compound (2) (416 g, 0.73 mol) in methanol (2000 ml). The reaction mixture was stirred at room temperature and monitored by TLC (silica gel, 10% methanol in dichloromethane, R$_f$ of compound 1: 0.53) and (silica gel, 30% methanol in dichloromethane, R$_f$ of compound 3: 0.21). Product started to precipitate after 30 minutes and TLC indicated reaction completion after two hours. The reaction was also monitored by HPLC (Method # 2). Methanol was removed under reduced pressure to a volume of ca. 500 ml chased with ethanol (2×500 ml) to a volume of ca. 500 ml. The residual thick slurry was diluted with 750 ml of ethanol and the mixture was stirred at 20° C. for one hour. Product was collected by filtration, filter cake washed with ethanol (100 ml) and tert-butyl-methyl ether (100 ml) and dried to give 168 g (90% yield for the two steps) of product (2) in purity of >97% (HPLC/AUC). Product was also analyzed by $^1$H and $^{13}$C NMR.

Example 7

N-[1-(3,4-dihydroxy-5-hydroxymethyl-3-methyl-tetrahydro-furan-2-yl)-2-oxo-1,2-dihydro-pyrimidine-4-yl]-N,N-dimethyl-formamidine: (Compound 4)

To a suspension of compound 3 (19 g, 0.0738 mol) in anhydrous N,N-dimethylformamide (150 ml) was added N,N-dimethylformamide dimethyl acetal (98 ml, 0.7385 mol) and the mixture was stirred at 20-22° C. After one hour TLC (silica gel, 30% methanol in dichloromethane, R$_f$ for compound 3: 0.21 and for product 4: 0.55) indicated that reaction was complete. Solvent and reagent were removed under reduced pressure (temperature was kept below 40° C.). Ethanol (50 ml) was added to the obtained oily residue and the solvent was removed under reduced pressure. This process was repeated twice and crude product solidified. The crude product was stirred with 190 ml of ethanol at 20° C. for one hour and kept at 5° C. for 12 hours. Solids were collected by filtration and filter cake washed with 30 ml of cold ethanol and 30 ml of cold tert-butyl-methyl ether. Drying the solid under vacuum gave 14.7 g (64%) of compound (4) as a first crop. TLC (silica gel, 30% methanol in dichloromethane, R$_f$ for product (4): 0.55) and (silica gel, 10% methanol in dichloromethane, R$_f$ for product (4): 0.1) showed only a single spot for compound (4) Mother liquor from the ethanol purification was evaporated to dryness and the residue was stirred with ethanol (80 ml) at 20° C. for one hour and kept at 5° C. for 12 hours. Solids were collected by filtration and filter cake washed with 15 ml of cold ethanol and 15 ml of cold tert-butyl-methyl ether. After drying the solid under vacuum, 3.5 g (15%) was obtained as a second crop. TLC (silica gel, 30% methanol in dichloromethane, $R_f$ for product (4): 0.55) and (silica gel, 10% methanol in dichloromethane, $R_f$ for product (4): 0.1) showed only a single spot for compound (4); m.p. 201-209° C.; $^1$H NMR (DMSO-$d_6$) δ ppm 8.62 (s, 1H, N=CH), 8.17 (d, 1H, H-6, $J_{5-6}$=7.3 Hz), 5.91 (m, 2H, H-1', H-5), 5.16 (t, 1H, OH-5', $D_2O$ exchangeable), 5.06 (s, 1H, OH-2', $D_2O$ exchangeable), 3.8-3.5 (m, 4H, H-3', H-4', H-5' and H-5"), 3.15 and 3.02 (2s, 6H, N(CH$_3$)$_2$), 0.92 (s, 3H, CH$_3$); FAB>0 (GT) 625 (2M+H)$^+$, 313 (M+H)$^+$, 167 (B+2H)$^+$; FAB<0, (GT) m/z 419 (M+T−H)$^-$, 403 (M+G−H)$^-$, 311 (M−H)$^-$, 165 (B)$^-$.

Example 8

N'-{1-[5-(tert-Butyl-diphenyl-silanyloxymethyl)-3,4-dihydroxy-3-methyl-tetrahydro-furan-2-yl]-2-oxo-1,2-dihydro-pyrimidin-4-yl}-N,N-dimethyl-formamidine: (Compound 5)

Compound (4) (42.9 g, 0.137 mol) was dispersed in anhydrous dichloromethane (200 ml) using an overhead stirrer for 30 min. The mixture was then evaporated to dryness (at ca. 30° C.) using the rotary evaporator. This dried compound (4), imidazole (37.4 g, 0.55 mol) and anhydrous dichloromethane (800 ml) were charged into a 2 L 4-necked RB flask under argon and tert-butyldiphenylchlorosilane (43.1 g, 0.156 mol, the total amount added in several portions) was transferred to an addition funnel attached to the reaction flak. The reaction mixture was cooled to 10° C. and tert-butyldiphenylchlorosilane (13.74 g, 0.05 mol) added from the addition funnel over a period of 20 min maintaining the reaction temperature between 10 to 12° C. while stirring. The reaction was monitored by HPLC (Method #2). After 1.5 hours, a second portion of tert-butyldiphenylchlorosilane (14.76 g, 0.053 mol) was added over a period of 20 min maintaining the reaction temperature between 10 to 12° C. After additional 1 hour, the remaining tert-butyldiphenylchlorosilane (14.8 g, 0.053 mol) was added over a period of 20 min maintaining the reaction temperature between 10 to 12° C. It was then stirred at 12-15° C. for further 1.5 hours. HPLC indicated 95.40% of product, 3.00% of bi-silyl derivative, and no un-reacted starting material. The reaction was quenched by adding saturated aqueous sodium bicarbonate solution (150 ml) with stirring for 15 min at about.15° C. (pH was around 8). The aqueous and dichloromethane layers were separated. The dichloromethane layer was washed with water (2×150 ml) and brine (1×200 ml), and dried over anhydrous sodium sulfate (60.0 g, 30 min). It was then filtered and solvent removed under reduced pressure. The residual foamy solid was used as is in the subsequent reaction.

Example 9

2-tert-Butoxycarbonylamino-3-methyl-butyric acid 2-(tert-butyl-diphenyl-silanyloxymethyl)-5-[4-(dimethylamino-methyleneamino)-2-oxo-2H-pyrimidin-1-yl]-4-hydroxy-4-methyl-tetrahydro-furan-3-yl ester: (Compound 6)

A solution of compound (5) (58 g, 0.1053 mol) in dichloromethane (500 ml) was stirred at 25° C. under argon atmosphere. N-(tert-butoxycarbonyl)-L-valine (29.7 g, 0.1367 mol), 1-[3-(dimethylamino)propyl]-3-ethylcarbodiimide hydrochloride (26.2 g, 0.1367 mol) and 4-(dimethylamino) pyridine (1.3 g, 0.0106 mol) were added and the reaction mixture was stirred at 25° C. and monitored by HPLC (method #2). After 4 hours, HPLC showed 7.9% of starting material. N-(tert-butoxycarbonyl)-L-valine (4.57 g, 0.0210 mol) and 1-[3-(dimethylamino)propyl]-3-ethylcarbodiimide hydrochloride (4.03 g, 0.0210 mol) were added and stirring was continued at 25° C. for an additional period of 2 hours, after which, HPLC detected 0.7% of starting material. Methanol (60 ml) was added to the reaction mixture and solvents were evaporated under reduced pressure (temperature kept below 40° C.) to give compound (6) as thick oil. This material (93% pure by HPLC/AUC) was used as is for the subsequent reaction.

Example 10

2-tert-Butoxycarbonylamino-3-methyl-butyric acid 5-(4-amino-2-oxo-2H-pyrimidin-1-yl)-4-hydroxy-2-hydroxymethyl-4-methyl-tetrahydro-furan-3-yl ester: (Compound 7)

Compound (6) (0.3 mol), MeOH (1650 ml) and EtOAc (265 g, 3.0 mol) were charged into a 3 L 5-necked RB flask and the mixture was stirred to dissolve compound (6). Ammonium fluoride (45.0 g, 1.21 mol) was added and the mixture was stirred under reflux up to 64.5° C. for 4 hours. The reaction was complete after four hours as indicated by HPLC (Method # 2). Solvents were then removed under reduced pressure at 40-45° C. and chased with EtOAc (300 ml). The residual foam was combined with EtOAc (400 ml), water (600 ml), and tert-butyl methyl ether (300 ml), and the mixture was triturated at ambient temperature for 2.5 hours. White solids that separated were collected by filtration, and washed with water (200 ml), 1:1 EtOAc/tert-butyl methyl ether (120 ml) and tert-butyl methyl ether (120 ml). The solid was then dried in vacuum for more than 20 hours to afford compound (7) as white solid. Yield 71.54 g, 52% for three steps. Compound (7) was obtained in 99.08% purity (HPLC, method #3). $^1$H NMR (DMSOd$_6$) δ ppm 7.99 (d, 1H, H-6, $J_{6-5}$=7.42 Hz), 7.3-7.1 (m, 3H, CH and NH$_2$, $D_2O$ exchangeable), 5.9 (s, 1H, H-1'), 5.75 (d, 1H, H-5, $J_{6-5}$=7.43 Hz), 5.43 (s, 1H, OH-2', $D_2O$ exchangeable), 5.24 (t, 1H, OH-5'), 5.04 (d, 1H, H-3', $J_{3'-4'}$=9.1 Hz), 4.1-4.0 (m, 2H, H-4', CH), 3.8-3.4 (2 m, 2H, H-5', H-5"), 2.2-2.0 (m, 1H, CH), 1.40 (s, 9H, (CH$_3$)$_3$C), 1.0 (s, 3H, CH$_3$), 0.9-0.8 (m, 6H, (CH$_3$)$_2$CH); FAB<0, (GT) m/e 911 (2M−H)$^-$, 455 (M−H)$^-$, 256 (M−BocVal)$^-$, 216 (BocValOH)$^-$, 110 (B)$^-$; FAB>0 (GT) 913 (2M+H)$^+$, 457 (M+H)$^+$, 112 (B+2H)$^+$, 57 (CH$_3$)$_3$C)$^+$; FAB<0 (GT) 911 (2M−H)$^-$, 455 (M−H)$^-$, 256 (M−BocVal)$^-$, 216 (BocVal)$^-$, 110 (B)$^-$.

Example 11

2-Amino-3-methyl-butyric acid 5-(4-amino-2-oxo-2H-pyrimidine-1-yl)-4-hydroxy-2-hydroxymethyl-4-methyl-tetrahydro-furan-3-yl ester (dihydrochloride salt): (Compound 8)

A solution of compound (7) (21.0 g, 0.046 mol) in ethanol (168 ml) was stirred in a round bottomed flask equipped with an overhead stirrer, temperature probe, argon line and hydrogen chloride gas bubbler. Hydrogen chloride gas (22 g) was bubbled into the clear solution over a period of one hour. The reaction temperature was kept below 30° C. using an ice-water bath. Solid formation started after a few minutes of introducing the hydrogen chloride gas. After 4 hours, HPLC (method # 3) showed only 0.8% of starting material. Solids were collected by filtration and filter cake washed with ethanol (20 ml) and di-ethyl ether (100 ml). After drying product under vacuum for 16 hours, 19.06 g (96.5%) of product (8) was obtained in 97.26% purity (HPLC, method # 3); m.p. 210° C. (brown), 248-250° C. (melted); $^1$H NMR (DMSO-d$_6$) δ ppm 10.0 (s, 1H, ½NH$_2$, D$_2$O exchangeable), 8.9-8.6 (2 br s, 4H, ½NH$_2$, NH$_3$, D$_2$O exchangeable), 8.42 (d, 1H, H-6, J$_{5-6}$=7.9 Hz), 6.24 (d, 1H, H-5, J$_{5-6}$=7.9 Hz), 5.84 (s, 1H, H-1'), 5.12 (d, 1H, H-3', J$_{3'-4'}$=8.8 Hz), 4.22 (d, 1H, H-4, J$_{3'-4'}$=8.7 Hz), 4.0-3.9 (m, 1H, CH), 3.8-3.5 (m, 2H, H-5', H-5"), 2.3-2.1 (m, 1H, CH), 1.16 (s, 3H, CH$_3$), 1.0 (m, 6H, (CH$_3$)$_2$CH); FAB>0 (GT) 713 (2M+H)$^+$, 449 (M+G+H)$^+$, 357 (M+H)$^+$, 246 (S)$^+$, 112 (B+2H)$^+$; FAB<0 (GT) 747 (2M+Cl)$^-$, 483 (M+G+Cl)$^-$, 391 (M+Cl)$^-$, 355 (M−H)$^-$, 116 (Val)$^-$, 110 (B)$^-$, 35 (Cl).

Example 12

HPLC Test Methods

All the described methods use reverse phase column; Waters® part number #WAT086344; Nova-Pak® C18, 60 Å pore size, 4 μm particle size, 3.9×150 mm. All chromatograms were generated using a Waters® 2695 HPLC and 996 PDA detector. Mobile Phase: HPLC grade acetonitrile and water were bought from JT Baker and 1M solution of triethylammonium acetate from Fluka®.

Method #1: Test for Compound 4, FIG. 4:

Flow rate: 1.00 ml/min. of acetonitrile/water linear gradient as described below.

System is equilibrated for five minutes equilibration between runs.

Wave length: 254 nm.

Retention time for Compound 4=12.8 minutes.

| Time | % Acetonitrile | % Water |
|---|---|---|
| 0.00 | 40.0 | 60.0 |
| 1.00 | 40.0 | 60.0 |
| 13.0 | 95.0 | 5.0 |
| 15.0 | 95.0 | 5.0 |

Method #2: Test for Compounds 2, 4, 5, 6 and 7, FIG. 4:

Flow rate: 1.00 ml/min. of an acetonitrile/20 mM aqueous triethylammonium acetate buffer gradient as described below.

System is equilibrated for five minutes between runs.

Wave length: 320 and 272 nm

| Time | % Acetonitrile | % Buffer |
|---|---|---|
| 0.00 | 0.00 | 100.0 |
| 15.00 | 80.0 | 20.0 |
| 30.00 | 80.0 | 20.0 |

Comparative Table: Compounds vs. Retention Times, Method #2:

| Compound | Retention Time (In Minutes) Wavelength |
|---|---|
| 1 | 18.2, 272 nm |
| 2 | 13.4, 272 nm |
| 3 | 2.9, 272 nm |
| Methyl benzoate | 11, 272 nm |
| Partially protected Compound 3 | 7.2, 272 nm |
| Partially protected Compound 3 | 10.0, 272 nm |
| 4 | 4.0, 320 nm |
| 5 | 13.2, 320 nm |
| Di-silylated Compound 5 | 16.6, 320 nm |
| 6 | 17.8, 320 nm |
| DMAP | 3.7 (Broad Peak), 272 nm |
| 7 | 8.3, 272 nm |
| Partially Deprotected 6 | 16.3, 272 nm |

Method #3: Test for Compounds 3, 7, and 8, FIG. 4:

Flow rate: 1.00 ml/min. of an acetonitrile/20 mM aqueous triethylammonium acetate buffer gradient as described below.

System is equilibrated for five minutes equilibration between runs.

Wave length: 272 nm

| Time | % Acetonitrile | % Buffer |
|---|---|---|
| 0.00 | 0.00 | 100.0 |
| 30.0 | 50.0 | 50.0 |

Comparative Table: Compounds vs. Retention Times, Method #3:

| Compound | Retention Time (In Minutes) |
|---|---|
| 7 | 18.4 |
| 8 | 8.5 |
| 3 | 3.6 |

Prior Art Processes

Example 13

Preparation of N$^4$-[(dimethylamino)methylene]-β-D 2'-C-methyl-cytidine (4)

A solution of β-D-2'-C-Methyl-Cytidine (3) (1.65 g, 6.43 mmol) in DMF (32 ml) was treated with N,N-dimethylformamide dimethylacetal (8.2 ml, 61.73 mmol), and stirred for about 1.5 hours at room temperature. The solution was evaporated under reduced pressure, and coevaporated with ethanol. Crystallization from ethanol/ether yielded a hitherto unknown compound, Compound (4) (first crop of 1.21 g, 60% yield, and second, slightly impure crop of 0.46 g, 23% yield) as crystals. The following physico-chemical characteristics have been determined on the crystals that issued from the first crop crystallization. F=201-209° C.; $^1$H NMR (DMSO-d$_6$) δ ppm 8.62 (s, 1H, N=CH), 8.17 (d, 1H, H-6, J$_{5-6}$=7.3 Hz), 5.91 (m, 2H, H-1', H-5), 5.16 (t, 1H, OH-5', D$_2$O exchangeable), 5.06 (s, 1H, OH-2', D$_2$O exchangeable), 3.8-3.5 (m, 4H, H-3', H-4', H-5' and H-5"), 3.15 and 3.02 (2s, 6H, N(CH$_3$)$_2$), 0.92 (s, 3H, CH$_3$); FAB>0 (GT) 625 (2M+H)$^+$, 313 (M+H)$^+$, 167 (B+2H)$^+$; FAB<0, (GT) m/z 419 (M+T-H)$^-$, 403 (M+G-H)$^-$, 311 (M-H)$^-$, 165 (B)$^-$; HPLC at room temperature for 5.96 min (gradient from 0 to 50% CH$_3$N in 20 mM triethyl ammonium acetate buffer programmed over a 30 min period with a flow rate of 1 ml/min), λ$_{max}$=316.1 nm.

Example 14

Preparation of N$^4$-[(dimethylamino)methylene]-5'-O-tert-butyldiphenylsilyl-β-D 2'-C-methyl-cytidine (5)

To a solution of compound (4) (1.167 g, 3.73 mmol) in dry pyridine (15 ml) were added successively imidazole (760 mg, 11.19 mmol) and tert-butyldiphenylchlorosilane (0.66 ml, 2.53 mmol). The solution was stirred at room temperature. After 4 hours, the reaction mixture was recharged with tert-butyldiphenylchlorosilane (0.40 ml, 2.28 mmol) and stirred at room temperature for 2 hours. Following extraction with sodium bicarbonate, the organic layer was washed with water, dried over sodium sulfate, and evaporated under reduced pressure. The crude mixture was taken up in a mixture of dry acetonitrile (30 ml) and dry dimethylformamide (15 ml).

Example 15

Preparation of 3'-O-L-N-(tert-butoxycarbonyl) valinyl ester of N$^4$-[((dimethylamino)methylene]-5'-O-tert-butyldiphenylsilyl-β-D 2'-C-methyl-cytidine (6)

To a solution of Compound (5) from the previous step were successively added N-(tert-butoxycarbonyl)-L-valine (Boc-Val-OH, 400 mg, 1.87 mmol), N'-(3-dimethylaminopropyl)-N-ethylcarbodiimide hydrochloride (DEC, 715 mg, 3.73 mmol), and 4-dimethylaminopyridine (DMAP, 68 mg, 0.56 mmol), and the solution was stirred at room temperature. The reaction profile was followed by HPLC. The reaction mixture was recharged three times with Boc-Val-OH (400 mg×3), DEC (715 mg×3), and DMAP (68 mg×3), and finally recharged one time with Boc-Val-OH (200 mg), DEC (357 mg), and DMAP (34 mg). After two days the starting material was totally consumed and the DMF was removed under reduced pressure. The residue, Compound (6), was taken up in dry methanol (70 ml).

Example 16

Preparation of 3'-O-L-N-(tert-butoxycarbonyl) Valinyl Ester of β-D 2'-C-methyl-cytidine (7)

Ammonium fluoride (1.38 g, 37.30 mmol) was added to the residue of Compound (6) in dry methanol, and the reaction mixture was refluxed for 3 hours. The mixture was filtered and the solvent removed from the filtrate under reduced pressure. The residue was taken up in ethyl acetate and extracted several times with water. The organic phase was evaporated under vacuum and purified on a silica gel chromatography column (eluant: MeOH (20%) in EtOAc (80%)). The desired compound (7) was isolated (1.37 g, 78% for the 3 steps) as a white foam.

Physico-chemical data included: $^1$H NMR (DMSO-d$_6$) δ ppm 7.99 (d, 1H, H-6, J$_{6-5}$=7.42 Hz), 7.3-7.1 (m, 3H, CH and NH$_2$, D$_2$O exchangeable), 5.9 (s, 1H, H-1'), 5.75 (d, 1H, H-5, J$_{6-5}$=7.43 Hz), 5.43 (s, 1H, OH-2', D$_2$O exchangeable), 5.24 (t, 1H, OH-5'), 5.04 (d, 1H, H-3', J$_{3'-4'}$=9.1 Hz), 4.1-4.0 (m, 2H, H-4', CH), 3.8-3.4 (2 m, 2H, H-5', H-5"), 2.2-2.0 (m, 1H, CH), 1.40 (s, 9H, (CH$_3$)$_3$C), 1.0 (s, 3H, CH$_3$), 0.9-0.8 (m, 6H, (CH$_3$)$_2$CH); FAB<0, (GT) m/e 911 (2M-H)$^-$, 455 (M-H)$^-$, 256 (M-BocVal)$^-$, 216 (BocValOH)$^-$, 110 (B)$^-$; FAB>0 (GT) 913 (2M+H)$^+$, 457 (M+H)$^+$, 112 (B+2H)$^+$, 57 (CH$_3$)$_3$C)$^+$; FAB<0 (GT) 911 (2M-H)$^-$, 455 (M-H)$^-$, 256 (M-BocVal)$^-$, 216 (BocVal)$^-$, 110 (B)$^-$.

Example 17

Preparation of 3'-O-L-valinyl ester of β-D 2'-C-methyl-cytidine (dihydrochloride salt, (8)

A solution of compound (7) (1.32 g, 2.9 mmol) in dry ethyl acetate (75 ml) was treated with a 20% HCl/ethyl acetate solution (75 ml). The reaction mixture was stirred at room temperature for 2 hours. The title compound, (8), precipitated in the reaction mixture, and was filtered and washed with Et$_2$O (1.01 g, 81% yield).

Physico-chemical characteristics included: F=210° C. (brown), 234-241° C. (melted); $^1$H NMR (DMSO-d$_6$) δ ppm 10.0 (s, 1H, ½NH$_2$, D$_2$O exchangeable), 8.9-8.6 (2 br s, 4H, ½NH$_2$, NH$_3$, D$_2$O exchangeable), 8.42 (d, 1H, H-6, J$_{5-6}$=7.9 Hz), 6.24 (d, 1H, H-5, J$_{5-6}$=7.9 Hz), 5.84 (s, 1H, H-1'), 5.12 (d, 1H, H-3', J$_{3'-4'}$=8.8 Hz), 4.22 (d, 1H, H-4, J$_{3'-4'}$=8.7 Hz), 4.0-3.9 (m, 1H, CH), 3.8-3.5 (m, 2H, H-5', H-5"), 2.3-2.1 (m, 1H, CH), 1.16 (s, 3H, CH$_3$), 1.0 (m, 6H, (CH$_3$)$_2$CH); FAB>0 (GT) 713 (2M+H)$^+$, 449 (M+G+H)$^+$, 357 (M+H)$^+$, 246 (S)$^+$, 112 (B+2H)$^+$; FAB<0 (GT) 747 (2M+Cl)$^-$, 483 (M+G+Cl)$^-$, 391 (M+Cl)$^-$, 355 (M-H)$^-$, 116 (Val)$^-$, 110 (B)$^-$, 35 (Cl)$^-$; HPLC rt=7.26 min (gradient from 0 to 50% CH$_3$N in 20 mM triethyl ammonium acetate buffer programmed over a 30 min period with a flow rate of 1 ml/min), λ$_{max}$=273.5 nm; UV (H$_2$O): λ$_{max}$=271 nm (ε7500), λ$_{min}$=249 nm (ε5200), λ$_s$=234 nm (ε6200).

Example 18

Synthesis of β-D-2'-C-Methyl-Cytidine (FIG. 6)

An alternative synthetic pathway for preparing β-D-2'-C-methyl-cytidine is referenced in FIG. 3. In this process, a mixture of uracil (2.1 eq.) and BSA (1.1 mL/mmol) in acetonitrile (7 mL/mmol) was heated to reflux for approximately 30 minutes. The resulting solution was treated with a solution of 1,2,3,5-tetra-O-benzoyl-2-C-methyl-β-D-ribofuranose (1) in acetonitrile (7 mL/mmol), and with SnCl$_4$ (3.5 eq.). The solution was heated to reflux for about 4 hours. The resultant dark mixture was diluted with ethyl acetate (2.5 the volume of toluene), and treated with cold, aqueous, saturated NaHCO$_3$ at a volume equal to that of ethyl acetate. The whole mixture was filtered through celite and the solid material washed with ethyl acetate. The organic layer was separated from the filtrate, washed with water, washed with brine, dried using Na$_2$SO$_4$, and evaporated under reduced pressure. Column chromatography on silica gel using 50% ethyl acetate in hexane produced a 65% yield of the Compound (9), β-D-2'-, 3'-, 5'-benzoyl-2'-C-methyl-uridine, as a white solid.

The benzoyl-protecting groups were removed from β-D-2'-, 3'-, 5'-benzoyl-2'-C-methyl-uridine (9) by solubilizing (9) in methanol (12.5 ml/mmol) treated with MeONa (3.3 eq.) and stirring the resultant yellow solution at room temperature for approximately 4.5 hours. The solution was neutralized by adding Dowex H$^+$ 50wX4 that was prewashed with methanol.

The mixture was filtered, and the resin was extracted several times with hot methanol. The filtrates were combined and evaporated under reduced pressure. The residue was taken up in water, and washed 3 times with dichloromethane. The aqueous layer was evaporated under reduced pressure. Crystallization from water provided (10), β-D-2'-C-methyl-uridine, in an 87% yield.

Next, a solution of β-D-2'-C-methyl-uridine (10), 1-methylpyrrolidine (1 ml/mmol), and chlorotrimethylsilane (3 eq.) in acetonitrile (10 ml/mmol) was stirred at room temperature for approximately 3.5 hours. The solution was cooled to 0° C., treated with trifluoroacetic anhydride (3 eq.), and stirred at the same temperature for 30 minutes. 4-nitrophenol (3 eq.) was added, and the solution was stirred for approximately 3 hours. The reaction was quenched by adding water to the solution, and the solvents were evaporated under reduced pressure. The residue was taken up in dichloromethane, and washed with aqueous, saturated $NaHCO_3$ and water. The organic layer was evaporated under reduced pressure. The crude residue taken up in dioxane (25 ml/mmol), and treated with a 28% aqueous solution of $NH_4OH$ (5 ml/mmol). The solution was heated to 50° C. overnight. Next, the solvents were evaporated under reduced pressure, and chromatographic separation was done using a gradient of methanol (5-20%) in dichloromethane. This produced β-D-2'-C-methyl-cytidine (U) as the desired product in 75% yield. The product was crystallized further in EtOH.

Sources for reagents in both Examples 5 and 6 included:
N,N-dimethylformamide dimethyl acetal from Fluka®, Reference No. 40271;
N,N-dimethylformamide over molecular sieve from Fluka®, Reference No. 40248;
Ethyl alcohol absolute from Carlo Erba ACS for analysis, Reference No. 414607;
Diethylether from Merck®, Reference No. 1.00921.5000;
tert-butyldiphenylchlorosilane from Avocado®, Reference No. 12721;
imidazole from Fluka®, Reference No. 56750;
pyridine over molecular sieve from Fluka®, Reference No. 82704;
sodium hydrogen carbonate from Fluka®, Reference No. 71628;
sodium sulfate, anhydrous, from Fluka®, Reference No. 71960;
acetonitrile over molecular sieve from Fluka®, Reference No. 00695;
N,N-dimethylformamide over molecular sieve from Fluka®, Reference No. 40248;
N-(tert-butoxycarbonyl)-L-valine from Aldrich®, Reference No. 35,972-6;
4-dimethylaminopyridine from Aldrich®, Reference No. 10,770-0;
N'-(3-dimethylaminopropyl)-N-ethylcarbodiimid hydrochloride from Aldrich®, Reference No. 16,146-2;
ammonium fluoride from Fluka®, Reference No. 09742;
methanol distilled over sodium;
ethyl acetate distilled over diphosphorus pentoxide
hydrogen chloride, anhydrous, from Praxair, Reference No. 1741100; and
diethylether from Merck®, Reference No. 1.00921.5000.

The foregoing is merely illustrative of the invention and is not intended to limit the invention to the disclosed processes and reaction conditions. Variations that are obvious to one of ordinary skill in the art are intended to be included with the scope and nature of the invention as defined in the appended claims.

What is claimed is:

1. A process for preparing 2-C-methyl-D-ribonolactone comprising:
   adding CaO to a solution of D-fructose at a molar ratio of CaO to D-fructose of from about 5 to 1 to about 1.8 to 1, wherein the reaction temperature is from about 23° C. to about 40° C.

2. The process of claim 1, further comprising:
   addition of $CO_2$ until the mixture is about pH 7; addition of oxalic acid until the mixture is about pH 2 to 3;
   separation of any resulting solid and aqueous phases;
   addition of an organic solvent to the aqueous phase;
   separation of the organic and aqueous phases;
   evaporation of the organic solvent of the organic phase, thereby isolating 2-C-methyl-D-ribono-lactone; and
   optionally precipitating the 2-C-methyl-D-ribono-lactone from acetone.

3. The process of claim 2, wherein the reaction time is from about 5 to about 25 hours.

4. The process of claim 1 wherein the 2-C-methyl-D-ribono-lactone is protected with a protecting group.

5. The process of claim 4 wherein the protected 2-C-methyl-D-ribono-lactone is 2,3,5-tri-O-benzoyl-2-C-methyl-D-ribono-lactone.

6. The process of claim 1 further comprising reducing the 2-C-methyl-D-ribono-lactone with sodium bis(2-methoxyethoxy)aluminum hydride/ethanol.

7. The process of claim 4 further comprising reducing the 2,3,5-tri-O-benzoyl-2-C-methyl-D-ribono-lactone with sodium bis(2-methoxyethoxy)aluminum hydride/ethanol to form 2,3,5-tri-O-benzoyl-2-C-methyl-D-ribofuranose.

8. The process of claim 7 further comprising protecting the 2,3,5-tri-O-benzoyl-2-C-methyl-D-ribofuranose with a protecting group to form a protected 2,3,5-tri-O-benzoyl-2-C-methyl-D-ribofuranose.

9. The process of claim 8, wherein the protected 2,3,5-tri-O-benzoyl-2-C-methyl-D-ribofuranose is 1,2,3,5-tetra-O-benzoyl-2-C-methyl-β-D-ribofuranose.

10. The process of claim 4, wherein the protecting group is selected from the group consisting of silyl, benzoyl, p-toluoyl, p-nitrobenzoyl, p-chlorobenzoyl, acyl, acetyl, —(C═O)-alkyl, and —(C═O)-aryl.

11. The process of claim 8, wherein the protecting group is selected from the group consisting of silyl, benzoyl, p-toluoyl, p-nitrobenzoyl, p-chlorobenzoyl, acyl, acetyl, —(C═O)-alkyl, and —(C═O)-aryl.

12. The process of claim 4, wherein the protecting group is —(C═O)-alkyl.

13. The process of claim 8, wherein the protecting group is —(C═O)-alkyl.

14. The process of claim 8, wherein the reactions are carried out in a solvent selected from the group consisting of water, toluene, tetrahydrofuran, dioxane, acetonitrile, dimethylformamide, dimethylsulfoxide and ethanol.

15. The process of claim 1 wherein the total time for synthesis is about 60 hours.

16. The process of claim 1 wherein the total time for synthesis is less than 60 hours.

17. The process of claim 8 wherein the total time for synthesis is from about 5 days to about 14 days.

18. The process of claim 8 wherein the total time for synthesis is from about 5 days to 10 days.

19. The process of claim 8 further comprising
    reacting the protected 2,3,5-tri-O-benzoyl-2-C-methyl-D-ribofuranose with an optionally protected activated nucleoside base, optionally in the presence of a Lewis acid, to form a D-2',3',5'-tri-O-benzoyl-2'-C-methyl-D-ribonucleoside product; and optionally deprotecting the D-2',3',5'-tri-O-benzoyl-2'-C-methyl-D-ribonucleoside product.

20. The process of claim 19, wherein the nucleoside base has been activated by reaction with a silylating agent.

21. The process of claim 20, wherein the silylating agent is selected from the group consisting of N,O-bis(trimethylsilyl)acetamide, hexamethyldisilazane, chlorotrimethylsilane, or tert-butyldiphenylsilyl chloride.

22. The process of claim 21, wherein the silylating agent is N,O-bis(trimethylsilyl)acetamide.

23. The process of claim 19, wherein the Lewis acid is selected from the group consisting of $SnCl_4$, $BF_3$, $AlCl_3$, $TiCl_2$, $TiCl_4$, $FeCl_3$, $SnCl_2$ and any mixture thereof.

24. The process of claim 23, wherein the Lewis acid is $SnCl_4$.

25. The process of claim 19, wherein the protected 2,3,5-tri-O-benzoyl-2-C-methyl-D-ribofuranose is 1,2,3,5-tetra-O-benzoyl-2-C-methyl-β-D-ribofuranose and the optionally protected nucleoside base is benzoylcytosine.

26. The process of claim 19, wherein the D-2',3',5'-tri-O-benzoyl-2'-C-methyl-D-ribonucleoside product is deprotected with sodium methoxide in methanol.

27. The process of claim 1, wherein the molar ratio of CaO to D-fructose is about 3 to 1.

28. The process of claim 1, wherein the molar ratio of CaO to D-fructose is about 2 to 1.

29. The process of claim 1, wherein the molar ratio of CaO to D-fructose is about 1.8 to 1.

30. The process of claim 2, wherein the total reaction time is about 22 hours.

* * * * *

UNITED STATES PATENT AND TRADEMARK OFFICE
CERTIFICATE OF CORRECTION

PATENT NO. : 7,598,373 B2 Page 1 of 1
APPLICATION NO. : 10/735408
DATED : October 6, 2009
INVENTOR(S) : Storer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 409 days.

Signed and Sealed this

Twenty-eighth Day of September, 2010

David J. Kappos
*Director of the United States Patent and Trademark Office*